United States Patent
Stierli et al.

(10) Patent No.: US 8,618,023 B2
(45) Date of Patent: Dec. 31, 2013

(54) MICROBIOCIDES

(75) Inventors: Daniel Stierli, Stein (CH); John J. Taylor, Bracknell (GB); Harald Walter, Stein (CH); Paul Anthony Worthington, Bracknell (GB)

(73) Assignee: Syngenta Crop Protection, LLC, Greensboro, NC (US)

( * ) Notice: Subject to any disclaimer, the term of this patent is extended or adjusted under 35 U.S.C. 154(b) by 905 days.

(21) Appl. No.: 12/301,080

(22) PCT Filed: May 16, 2007

(86) PCT No.: PCT/EP2007/004425
§ 371 (c)(1),
(2), (4) Date: Mar. 19, 2009

(87) PCT Pub. No.: WO2007/134799
PCT Pub. Date: Nov. 29, 2007

(65) Prior Publication Data
US 2010/0022570 A1    Jan. 28, 2010

(30) Foreign Application Priority Data

May 18, 2006   (EP) .................................. 06010224

(51) Int. Cl.
*A01N 43/00* (2006.01)
*C07D 231/10* (2006.01)
*C07D 231/00* (2006.01)

(52) U.S. Cl.
USPC ...................... 504/139; 548/374.1; 548/373.1

(58) Field of Classification Search
USPC .............................. 548/374.1, 373.1; 504/139
See application file for complete search history.

(56) References Cited

U.S. PATENT DOCUMENTS 5,849,769 A    12/1998 Lind et al.
2004/0082628 A1*   4/2004 Strobel et al. ................. 514/365

FOREIGN PATENT DOCUMENTS

| EP | 0994102 | 4/2000 |
|---|---|---|
| EP | 1134214 | 9/2001 |
| JP | 09165374 | 6/1997 |
| WO | 2006122952 | 11/2006 |
| WO | 2006122955 | 11/2006 |

OTHER PUBLICATIONS

L. Arvidsson et al: "N,N-Dialkylated Monophenolic trans-2-Phenylcyclopropylamines: Novel Central 5-Hydroxytryptamine Receptor Agonists"; Journal of Medicinal Chemistry, vol. 31, No. 1988, pp. 92-99, XP0024515111, p. 92.
David E. Nichols et al: "Synthesis and Evaluation of Substituted 2-Phenylcyclobutylamines as Analogues of Hallucinogenic Phenethylamines: Lack of LSD-like Biological Activity"; Journal of Medicinal Chemistry, vol. 27, No. 9, 1984, pp. 1108-1111, XP002451512, p. 1108.

* cited by examiner

*Primary Examiner* — Shengjun Wang
(74) *Attorney, Agent, or Firm* — R. Kody Jones

(57) ABSTRACT

Compounds of the formula (I) in which the substituents are as defined in claim 1 are suitable for use as microbiocides. Formula (I), wherein X is oxygen or sulfur; A is a 5- or 6-membered heterocyclic ring containing one to three heteroatoms, each independently selected from oxygen, nitrogen and sulphur, or a phenyl ring; the heterocyclic ring or the phenyl being substituted by the groups $R_6$, $R_7$ and $R_8$; $R_6$, $R_7$ and $R_8$ are each, independently, hydrogen, halogen, cyano, nitro, $C_{1-4}$ alkyl, $C_{1-4}$ halogenalkyl, $C_{1-4}$ halogenalkoxy, $C_{1-4}$ alkoxy($C_{1-4}$)alkyl or $C_{1-4}$halogenalkoxy($C_{1-4}$)alkyl, provided that at least one of $R_6$, $R_7$ and $R_8$ is not hydrogen; B is a phenyl, naphthyl or quinolinyl group, which is substituted by one or more substituents $R_9$.

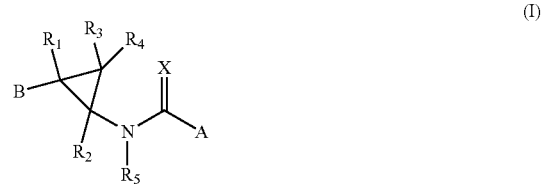

(I)

9 Claims, No Drawings

MICROBIOCIDES

This application is a 371 of International Application No. PCT/EP2007/004425 filed May 16, 2007, which claims priority to EP 06010224.1 filed May 18, 2006, the contents of which are incorporated herein by reference.

The present invention relates to novel microbiocidally active, in particular fungicidally active, cyclopropyl amides. It further relates to intermediates used in the preparation of these compounds, to compositions which comprise these compounds and to their use in agriculture or horticulture for controlling or preventing infestation of plants by phytopathogenic microorganisms, preferably fungi.

N-[2-(2-pyridinyl)cycloalkyl]-carboxamide derivatives and their use as fungicides are described in WO 05/103006 and WO 05/103004. 2,6-Di-chloro-isonicotinic acid phenethyl-amide derivatives and their use as pesticides are described in JP-09-165-374.

It has been found that novel cyclopropyl amides have microbiocidal activity.

The present invention thus provides compounds of the formula I

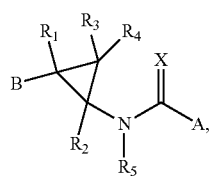

wherein
X is oxygen or sulfur;
A is a 5- or 6-membered heterocyclic ring containing one to three heteroatoms, each independently selected from oxygen, nitrogen and sulphur, or a phenyl ring; the heterocyclic ring or the phenyl being substituted by the groups $R_6$, $R_7$ and $R_8$;
$R_6$, $R_7$ and $R_8$ are each, independently, hydrogen, halogen, cyano, nitro, $C_{1-4}$alkyl, $C_{1-4}$ halogenalkyl, $C_{1-4}$ halogenalkoxy, $C_{1-4}$ alkoxy($C_{1-4}$)alkyl or $C_{1-4}$ halogenalkoxy($C_{1-4}$) alkyl, provided that at least one of $R_6$, $R_7$ and $R_8$ is not hydrogen;
$R_1$, $R_2$, $R_3$ and $R_4$ independently of each other stand for hydrogen, halogen, cyano, nitro, $C_1$-$C_6$alkyl, which is unsubstituted or substituted by one or more substituents $R^a$, $C_3$-$C_6$cycloalkyl, which is unsubstituted or substituted by one or more substituents $R^a$, $C_2$-$C_6$alkenyl, which is unsubstituted or substituted by one or more substituents $R^a$ or $C_2$-$C_6$alkynyl, which is unsubstituted or substituted by one or more substituents $R^a$;
each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio or —C($R^b$)=N (O$R^c$);
$R^b$ is hydrogen or $C_1$-$C_6$alkyl;
$R^c$ is $C_1$-$C_6$alkyl;
$R_5$ is hydrogen, $C_{1-4}$ alkyl, $CH_2CH=CHR_{5a}$, $CH_2C\equiv CR_{5b}$ or $COR_{5c}$;
$R_{5a}$ and $R_{5b}$ are each, independently, hydrogen, $C_1$-$C_6$alkyl, $C_1$-$C_6$halogenalkyl, $C_2$-$C_6$alkenyl, $C_2$-$C_6$alkynyl, $C_3$-$C_7$cycloalkyl, COO$C_1$-$C_4$alkyl, COO$C_3$-$C_6$alkenyl, COO$C_3$-$C_6$alkynyl or CN;
$R_{5c}$ is hydrogen, $C_1$-$C_6$alkyl, $C_1$-$C_6$halogenalkyl, $C_1$-$C_6$alkoxy-$C_1$-$C_6$alkyl, $C_1$-$C_6$halogenalkoxy-$C_1$-$C_6$alkyl, $C_1$-$C_6$alkylthio, $C_1$-$C_6$halogenalkylthio, $C_1$-$C_6$alkoxy, $C_1$-$C_6$halogenalkoxy, $C_3$-$C_6$alkenyloxy, $C_3$-$C_6$halogenalkenyloxy, $C_3$-$C_6$alkynyloxy or $C_3$-$C_6$halogenalkynyloxy;
B is a phenyl, naphthyl or quinolinyl group, which is substituted by one or more substituents $R_9$;
each substituent $R_9$ independently of each other stands for halogen, cyano, nitro, —C($R^d$)=N(O$R^e$) or a group -L-$R^f$;
each $R^d$ is independently of each other hydrogen or $C_1$-$C_6$alkyl;
each $R^e$ is independently of each other $C_1$-$C_6$alkyl;
each L is independently of each other a bond, —O— or —S—;
each $R^f$ is independently of each other $C_1$-$C_6$alkyl, which is unsubstituted or substituted by one or more substituents $R^h$, $C_3$-$C_6$cycloalkyl, which is unsubstituted or substituted by one or more substituents $R^h$, $C_6$-$C_{14}$bicycloalkyl, which is unsubstituted or substituted by one or more substituents $R^h$, $C_2$-$C_6$alkenyl, which is unsubstituted or substituted by one or more substituents $R^h$, $C_2$-$C_6$alkynyl, which is unsubstituted or substituted by one or more substituents $R^h$, phenyl, which is unsubstituted or substituted by one or more substituents $R^h$, phenyl, which is unsubstituted or substituted by one or more substituents $R^h$ or heteroaryl, which is unsubstituted or substituted by one or more substituents $R^h$;
each $R^h$ is independently of each other halogen, cyano, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy or —C($R^i$)=N(O$R^k$);
each $R^i$ is independently of each other hydrogen or $C_1$-$C_6$alkyl;
each $R^k$ is independently of each other $C_1$-$C_6$alkyl;
and tautomers/isomers/enantiomers of these compounds.

The alkyl groups occurring in the definitions of the substituents can be straight-chain or branched and are, for example, methyl, ethyl, n-propyl, n-butyl, n-pentyl, n-hexyl, isopropyl, n-butyl, sec-butyl, isobutyl or tert-butyl. Alkoxy, alkenyl and alkynyl radicals are derived from the alkyl radicals mentioned. The alkenyl and alkynyl groups can be mono- or di-unsaturated.

The cycloalkyl groups occurring in the definitions of the substituents are, for example, cyclopropyl, cyclobutyl, cyclopentyl or cyclohexyl.

The bicycloalkyl groups occurring in the definitions of the substituents are, depending on the ring size, bicyclo[2.1.1] hexane, bicyclo[2.2.1]heptane, bicyclo[2.2.2]octane, bicyclo [3.2.1]octane, bicyclo[3.2.2]nonane, bicyclo[4.2.2]decane, bicyclo[4.3.2]undecane, adamantane and the like.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable halogenalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3, 3-trifluoropropenyl, 2,3,3-trichloropropenyl and 4,4,4-trifluorobut-2-en-1-yl.

Suitable halogenalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In the context of the present invention "substituted by one or more substituents" in the definition of substituents $R_1$, $R_2$, $R_3$, $R_4$ and $R^f$, means typically, depending on the chemical structure of substituents $R_1$, $R_2$, $R_3$, $R_4$ and $R^f$, monosubstituted to nine-times substituted, preferably monosubstituted to five-times substituted, more preferably mono-, double- or triple-substituted.

In the context of the present invention "substituted by one or more substituents" in the definition of substituent B, means typically, depending on the chemical structure of substituent B, monosubstituted to seven-times substituted, preferably monosubstituted to five-times substituted, more preferably mono-, double- or triple-substituted.

In the context of the present invention a "5- or 6-membered heterocyclic ring containing one to three heteroatoms, each independently selected from oxygen, nitrogen and sulphur" preferably means pyrazolyl (especially pyrazol-4-yl), thiazolyl (especially thiazol-5-yl), pyrrolyl (especially pyrrol-3-yl), 1,2,3 triazolyl, oxazolyl (especially oxazol-5-yl), pyridyl (especially pyrid-3-yl) or 2,3 dihydro-[1,4]oxathiinyl (especially 2,3 dihydro-[1,4]oxathiin-5-yl).

In the context of the present invention "heteroaryl" is preferably understood to be an aromatic 5- or 6-membered heteroaryl group bonded via a carbon atom or an nitrogen atom, which group may be interrupted once by oxygen, once by sulfur and/or once, twice or three times by nitrogen. Said groups bonded via a carbon atom are, for example, pyrazol-3-yl, pyrazol-4-yl, 3-isoxazolyl, pyrrol-2-yl, pyrrol-3-yl, 2-furyl, 3-furyl, 2-thienyl, 3-thienyl, imidazol-2-yl, imidazol-4-yl, imidazol-5-yl, 2-oxazolyl, 5-oxazolyl, 4-oxazolyl, 2-thiazolyl, 5-thiazolyl, 4-thiazolyl, 4-isothiazolyl, 5-isothiazolyl, 3-isothiazolyl, 1,2,3-triazol-4-yl, 1,2,3-triazol-2-yl, 1,2,4-triazol-3-yl, 1,2,3-oxadiazol-4-yl, 1,2,4-oxadiazol-5-yl, 1,2,4-oxadiazol-3-yl, 1,2,3-thiadiazol-4-yl, 1,2,4-thiadiazol-5-yl, 1,2,4-thiadiazol-3-yl, 1,2,5-thiadiazol-3-yl, 1,3,4-thiadiazol-2-yl, 2-pyridyl, 4-pyridyl, 3-pyridyl, 3-pyridazinyl, 3-pyridazinyl, 2-pyrimidinyl, 4-pyrimidinyl, 5-pyrimidinyl, 2-pyrazinyl, 1,3,5-triazin-2-yl, 1,2,4-triazin-5-yl or 1,2,4-triazin-6-yl. Said groups bonded via a nitrogen atom are, for example, 1H-pyrrol-1-yl, 1H-pyrazol-1-yl, 1H-1,2,4-triazol-1-yl or 4H-1,2,4-triazol-4-yl.

All compounds of formula I occur in at least two different isomeric forms: $I_I$ (cis) and $I_{II}$ (trans):

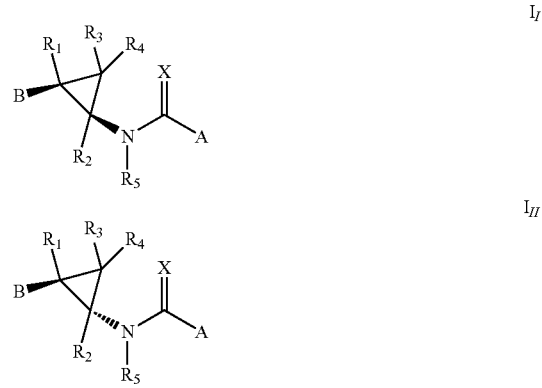

The invention covers all those isomers and mixtures thereof.

The compounds of the formula I may occur in different tautomeric forms. For example, compounds of formula I, wherein X is oxygen and $R_2$ is hydrogen, exist in the tautomeric forms $I_{III}$ and $I_{IV}$:

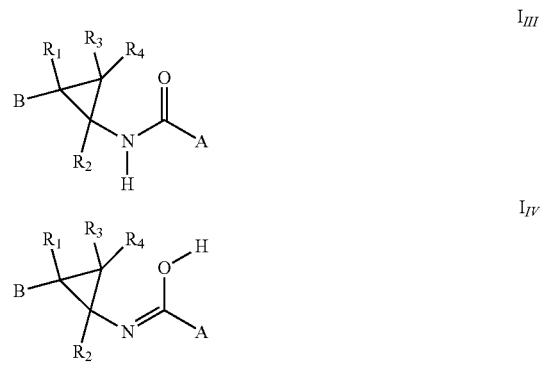

The invention covers all those tautomeric forms and mixtures thereof.

In a preferred group of compounds A is a 5-membered heterocyclic ring containing one to three heteroatoms, each independently selected from oxygen, nitrogen and sulphur; the heterocyclic ring being substituted by the groups $R_6$, $R_7$ and $R_8$.

Within said preferred group of compounds, further preferably A is $A_1$

in which
$R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{18}$ is hydrogen, halogen or cyano;

or A is $A_2$

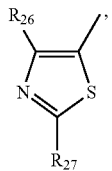

(A$_2$)

in which $R_{26}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{27}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_3$

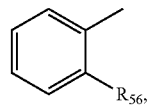

(A$_3$)

in which $R_{36}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{37}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{38}$ is hydrogen, halogen or cyano;

or A is $A_4$

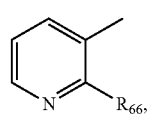

(A$_4$)

in which $R_{46}$ and $R_{47}$ independently of one another are halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl.

Within said preferred group of compounds, further preferably A is $A_1$.

Within said preferred group of compounds, further preferably A is $A_2$.

Within said preferred group of compounds, further preferably A is $A_3$.

Within said preferred group of compounds, further preferably A is $A_4$.

In another preferred group of compounds A is a phenyl ring or a 6-membered heterocyclic ring containing one to three heteroatoms, each independently selected from oxygen, nitrogen and sulphur; the phenyl ring or the heterocyclic ring being substituted by the groups $R_6$, $R_7$ and $R_8$.

Within said preferred group of compounds, further preferably A is $A_5$

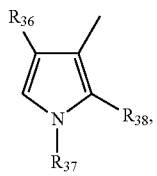

(A$_5$)

in which $R_{56}$ is halogen, $C_1$-$C_4$halogenalkyl, $C_1$-$C_4$halogenalkoxy or $C_1$-$C_4$halogenalkoxy-$C_1$-$C_4$alkyl; or A is $A_6$

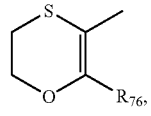

(A$_6$)

in which $R_{66}$ is halogen, cyano, nitro, $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; or A is $A_7$

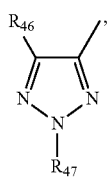

(A$_7$)

in which $R_{76}$ is $C_1$-$C_4$alkyl or $C_1$-$C_4$halogenalkyl.

Within said preferred group of compounds, further preferably A is $A_5$.

Within said preferred group of compounds, further preferably A is $A_6$.

Within said preferred group of compounds, further preferably A is $A_7$.

In a particular preferred group of compounds A is $A_1$, wherein $R_{18}$ is hydrogen. In another particular preferred group of compounds A is $A_1$, wherein $R_{16}$ is $C_1$-$C_4$alkyl or $C_1$-$C_4$haloalkyl, preferably $C_1$-$C_4$haloalkyl; $R_{17}$ is $C_1$-$C_4$alkyl; and $R_{18}$ is hydrogen or halogen, preferably hydrogen.

In another particular preferred group of compounds A is $A_2$, wherein $R_{26}$ is $C_1$-$C_4$alkyl or $C_1$-$C_4$haloalkyl; and $R_{27}$ is $C_1$-$C_4$alkyl.

In yet another particular preferred group of compounds A is $A_3$, wherein $R_{36}$ is $C_1$-$C_4$alkyl or $C_1$-$C_4$haloalkyl; $R_{37}$ is $C_1$-$C_4$alkyl; and $R_{38}$ is hydrogen or halogen.

In yet another particular preferred group of compounds A is $A_4$, wherein $R_{46}$ is $C_1$-$C_4$alkyl or $C_1$-$C_4$haloalkyl; and $R_{47}$ is $C_1$-$C_4$alkyl.

In yet another particular preferred group of compounds A is $A_4$, wherein $R_{46}$ halomethyl, preferably $R_{46}$ is selected from $CF_3$, $CF_2H$ and $CFH_2$; and $R_{47}$ is $C_1$-$C_4$alkyl.

In yet another particular preferred group of compounds A is $A_5$, wherein $R_{56}$ is halogen or $C_1$-$C_4$haloalkyl.

In yet another particular preferred group of compounds A is $A_6$, wherein $R_{66}$ is halogen or $C_1$-$C_4$haloalkyl.

In yet another particular preferred group of compounds A is $A_7$, wherein $R_{76}$ is $C_1$-$C_4$alkyl or $C_1$-$C_4$haloalkyl.

One embodiment of the invention is represented by compounds, wherein X is oxygen.

Another embodiment of the invention is represented by compounds, wherein X is sulfur.

Compounds, wherein X is oxygen are preferred.

In a preferred group of compounds $R_5$ is hydrogen.

In a preferred group of compounds $R_1$, $R_2$, $R_3$ and $R_4$ independently of each other stands for hydrogen, halogen, cyano or $C_1$-$C_6$alkyl, which is unsubstituted or substituted by one or more substituents selected from halogen, cyano, $C_1$-$C_6$alkoxy and $_1$-$C_6$halogenalkoxy; more preferably $R_1$, $R_2$, $R_3$ and $R_4$ independently of each other stands for hydrogen, halogen, cyano or $C_1$-$C_6$alkyl, which is unsubstituted or substituted by one or more substituents selected from halogen and $C_1$-$C_6$alkoxy; most preferably $R_1$, $R_2$, $R_3$ and $R_4$ independently of each other stands for hydrogen, halogen, or $C_1$-$C_6$alkyl.

In a preferred group of compounds $R_1$ is hydrogen, halogen, $C_1$-$C_6$alkyl, $C_1$-$C_6$halogenalkyl or $C_1$-$C_6$alkoxy-$C_1$-$C_6$alkyl;

$R_2$ is hydrogen, halogen, $C_1$-$C_6$alkyl, $C_1$-$C_6$halogenalkyl or $C_1$-$C_6$alkoxy-$C_1$-$C_6$alkyl;

$R_3$ is hydrogen, halogen, $C_1$-$C_6$alkyl, $C_1$-$C_6$halogenalkyl or $C_1$-$C_6$alkoxy-$C_1$-$C_6$alkyl; and $R_4$ is hydrogen, halogen, $C_1$-$C_6$alkyl, $C_1$-$C_6$halogenalkyl or $C_1$-$C_6$alkoxy-$C_1$-$C_6$alkyl.

Within said embodiment, preferably, $R_1$ is hydrogen, halogen or $C_1$-$C_6$alkyl; and $R_2$, $R_3$ and $R_4$ are each independently selected from hydrogen and $C_1$-$C_6$alkyl. Within said embodiment, more preferably $R_3$ and $R_4$ are hydrogen. In one embodiment $R_2$, $R_3$ and $R_4$ are hydrogen. In another embodiment, $R_1$, $R_2$, $R_3$ and $R_4$ are hydrogen.

One embodiment of the invention is represented by compounds, wherein B is a phenyl group, which is substituted by one or more substituents $R_9$.

Within said embodiment, preferably B is a phenyl group, which is substituted by one, two or three substituents $R_9$; more preferably B is a phenyl group, which is substituted by one or two substituents $R_9$.

Also preferably, B is a phenyl group, that is substituted by at least one substituent $R_9$ in the para-position.

In a preferred group of compounds each substituent $R_9$ independently of each other stands for halogen, —C($R^d$)=N(O$R^e$) or -L-R'; more preferably each substituent $R_9$ independently of each other stands for halogen or -L-R'. In a preferred group of compounds each L independently of each other is a bond or —O—. In a preferred group of compounds each substituent $R^f$ independently of each other stands for $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Within said embodiment, further preferably B is $B_1$

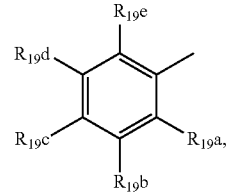

(B$_1$)

in which $R_{19a}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{19b}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{19c}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{19d}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{19e}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

provided that at least one of $R_{19a}$, $R_{19b}$, $R_{19c}$, $R_{19d}$ and $R_{19e}$ is not hydrogen.

In one embodiment of the invention, $R_{19b}$ and $R_{19d}$ is hydrogen; and $R_{19a}$, $R_{19c}$ and $R_{19e}$ independently of one another are selected from hydrogen, halogen, cyano, $C_2$-$C_6$alkynyl, $C_1$-$C_6$halogenalkyl, $C_1$-$C_6$halogenalkoxy or phenyl, which is substituted halogen; provided that at least one of $R_{19a}$, $R_{19c}$ and $R_{19e}$ is not hydrogen.

Another embodiment of the invention is represented by compounds, wherein B is a naphthyl or quinolinyl group, which is substituted by one or more substituents $R_9$.

Another embodiment of the invention is represented by compounds, wherein B is a naphthyl group, which is substituted by one or more substituents $R_9$.

Within said embodiment, preferably B is a naphthyl group, which is substituted by one or two substituents $R_9$. Within said embodiment, in a preferred group of compounds each substituent $R_6$ independently of each other stands for halogen, —C($R^d$)=N(O$R^e$) or -L-$R^f$; more preferably each substituent $R_6$ independently of each other stands for halogen or -L-$R^f$. In a preferred group of compounds each L independently of each other is a bond or —O—. In a preferred group of compounds each substituent $R^f$ independently of each other stands for $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Another embodiment of the invention is represented by compounds, wherein B is a quinolinyl group, which is substituted by one or more substituents $R_9$.

Within said embodiment, preferably B is a quinolinyl group, which is substituted by one or two substituents $R_9$. Within said embodiment, in a preferred group of compounds each substituent $R_6$ independently of each other stands for halogen, —C($R^d$)=N(O$R^e$) or -L-$R^f$; more preferably each substituent $R_6$ independently of each other stands for halogen or -L-$R^f$. In a preferred group of compounds each L independently of each other is a bond or —. In a preferred group of compounds each substituent $R^f$ independently of each other stands for $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Compounds of formula I, wherein $R_5$ is hydrogen and X is oxygen, may be prepared by reacting a compound of formula II

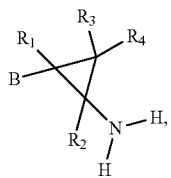

(II)

in which B, $R_1$, $R_2$, $R_3$ and $R_4$ are as defined under formula I; with a compound of formula III

A-C(=O)—R*  (III), in which A is as defined under formula I, and R* is halogen, hydroxy or $C_{1-6}$ alkoxy, preferably chloro, in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

The Intermediates of the Formula II

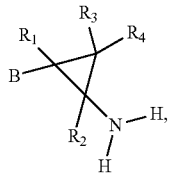

(II)

in which B, $R_1$, $R_2$, $R_3$ and $R_4$ are as defined under formula I; are novel and were developed specifically for the preparation of the compounds of the formula I. Accordingly, they also form part of the subject-matter of the present invention.

In preferred intermediates of formula II, $R_1$, $R_2$, $R_3$ and $R_4$ independently of each other stands for hydrogen, halogen, cyano or $C_1$-$C_6$alkyl, which is unsubstituted or substituted by one or more substituents selected from halogen, cyano, $C_1$-$C_6$alkoxy and 1-$C_6$halogenalkoxy; more preferably $R_1$, $R_2$, $R_3$ and $R_4$ independently of each other stands for hydrogen, halogen, cyano or $C_1$-$C_6$alkyl, which is unsubstituted or substituted by one or more substituents selected from halogen and $C_1$-$C_6$alkoxy; most preferably $R_1$, $R_2$, $R_3$ and $R_4$ independently of each other stands for hydrogen, halogen, or $C_1$-$C_6$alkyl.

In a preferred group of intermediates of formula II, $R_1$ is hydrogen, halogen, $C_1$-$C_6$alkyl, $C_1$-$C_6$halogenalkyl or $C_1$-$C_6$alkoxy-$C_1$-$C_6$alkyl; $R_2$ is hydrogen, halogen, $C_1$-$C_6$alkyl, $C_1$-$C_6$halogenalkyl or $C_1$-$C_6$alkoxy-$C_1$-$C_6$alkyl; $R_3$ is hydrogen, halogen, $C_1$-$C_6$alkyl, $C_1$-$C_6$halogenalkyl or $C_1$-$C_6$alkoxy-$C_1$-$C_6$alkyl; and $R_4$ is hydrogen, halogen, $C_1$-$C_6$alkyl, $C_1$-$C_6$halogenalkyl or $C_1$-$C_6$alkoxy-$C_1$-$C_6$alkyl. Within said embodiment, preferably, $R_1$ is hydrogen, halogen or $C_1$-$C_6$alkyl; and $R_2$, $R_3$ and $R_4$ are each independently selected from hydrogen and $C_1$-$C_6$alkyl. Within said embodiment, more preferably $R_3$ and $R_4$ are hydrogen. In one embodiment $R_2$, $R_3$ and $R_4$ are hydrogen.

In preferred intermediates of formula II B is a phenyl group, which is substituted by one or more substituents $R_9$. Within said embodiment, preferably B is a phenyl group, which is substituted by one, two or three substituents $R_9$; more preferably B is a phenyl group, which is substituted by one or two substituents $R_9$. Also preferably, in intermediates of formula II B is a phenyl group, that is substituted by at least one substituent $R_9$ in the para-position.

In a preferred group of intermediates of formula II each substituent $R_9$ independently of each other stands for halogen, —C($R^d$)=N(O$R^e$) or -L-$R^f$; more preferably each substituent $R_9$ independently of each other stands for halogen or -L-$R^f$. In a preferred group of compounds each L independently of each other is a bond or —O—. In a preferred group of compounds each substituent $R^f$ independently of each other stands for $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Within said embodiment, further preferably in intermediates of formula II B is $B_1$

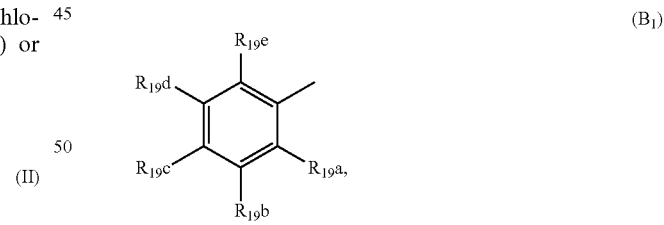

($B_1$)

in which $R_{19a}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{19b}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{19c}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{19d}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{19e}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; provided that at least one of $R_{19a}$, $R_{19b}$, $R_{19c}$, $R_{19d}$ and $R_{19e}$ is not hydrogen.

In one embodiment of the invention, in intermediates of formula II $R_{19b}$ and $R_{19d}$ is hydrogen; and $R_{19a}$, $R_{19g}$ and $R_{19e}$ independently of one another are selected from hydrogen, halogen, cyano, $C_2$-$C_6$alkynyl, $C_1$-$C_6$halogenalkyl, $C_1$-$C_6$halogenalkoxy or phenyl, which is substituted halogen; provided that at least one of $R_{19a}$, $R_{19c}$ and $R_{19e}$ is not hydrogen.

In another embodiment of the invention, in intermediates of formula II B is a naphthyl or quinolinyl group, which is substituted by one or more substituents $R_9$.

Intermediates of the formula II, in which B, $R_1$, $R_2$, $R_3$ and $R_4$ are as defined under formula I; may be prepared according to the following reaction schemes (scheme 1 and 2) or in analogy to those reaction schemes.

Intermediates of the Formula IIB

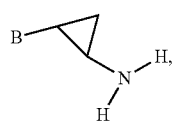

in which B is as defined under formula I (intermediates of formula II, in which $R_1$, $R_2$, $R_3$ and $R_4$ are hydrogen and B is as defined under formula I) may be prepared by reaction scheme 1.

Scheme 1:

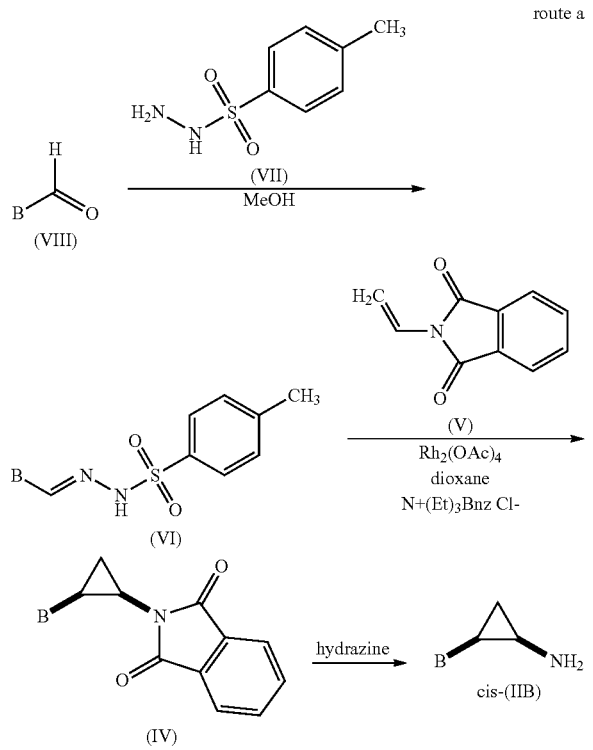

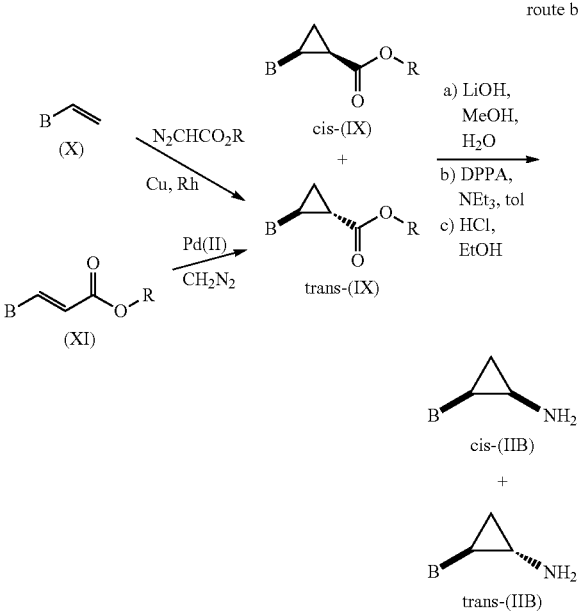

Scheme 1, Route a (Cis-Selective Synthesis):

According to the procedure of Varinder K. Aggarwal et al, *Organic Lett.* 2001, Vol. 3, No. 17, 2785-2788, aldehydes of formula VIII, wherein B is as defined under formula I, are reacted with compounds of formula VII to give tosylhydrazones of formula VI, wherein B is as defined under formula I. These diazo-precursors of formula VI can be induced to react directly with N-vinylphthalimide (V) to afford phthalimides of the formula IV, wherein B is as defined under formula I, and following hydrazinolysis to afford the cis-2-arylcyclopropylamines of the formula IIB, wherein B is as defined under formula I.

The reactions are carried out at temperatures of between 0-50° C. in a convenient organic solvent such as methanol, ethanol, chloroform, dichloromethane or dioxane.

A range of metal catalysts such as the ones derived from copper, palladium, iron or rhodium can be used for the cyclopropanation reaction. The preferred catalyst is rhodium acetate which reacts with the sodium or lithium salt of the tosylhydrazone and N-vinylphthalimide (V) in the presence of a phase transfer catalyst such as benzyltriethylammonium chloride to give phthalimides of the formula IV.

The phthalimides of the formula IV are converted to the amines of formula IIB with hydrazine hydrate in a convenient solvent such as ethanol.

Scheme 1, Route b: Synthesis of Trans-Compounds

According to the procedure of A. Burger et al, *J. Am. Soc.*, 70, 2198 (1948), *J. of Med. Chem.* 1962, 5, 1243-1265, 2-arylcyclopropylamines of the formula IIB, wherein B is as defined under formula I, can be prepared with a moderate trans-selectivity.

The cyclopropyl-esters trans/cis-(IX), wherein B is as defined under formula I, can be prepared by metal catalyzed cyclopropanation of an alkyl-diazoacetate of the formula $N_2CHCO_2R$, wherein R is $C_1$-$C_6$alkyl, with an olefin of the formula X, wherein B is as defined under formula I. Suitable solvents for this process include ether, $CH_2Cl_2$ and $ClCH_2CH_2Cl$, preferably ether. Reaction temperatures range from room temperature to 60° C., preferably 40° C. Suitable catalysts for the cyclopropanation are $Cu(acac)_2$ or $Pd(OAc)_2$.

The 2-arylcyclopropylamines trans/cis-(IIB) are then prepared from the cyclopropyl-esters trans/cis-(IX) using a three-step sequence: basic hydrolysis of the ester (J. Valigarda et al, *J. Chem. Soc. Perkin Trans.* 1 1994), Curtius rearrangement, and finally hydrolysis of the isocyanate (P. A. S. Smith, *Org. Reactions, III,* 337 1946). The trans-2-arylcyclopropylamines of formula trans-(IIB) can be purified by recrystallisation of the corresponding D- and L-tartrates from aqueous 2-propanol according to known methods. 2-arylcyclopropylesters trans/cis-(IX) can selectively hydrolyzed by a modification of the method of H. M Walborsky and L. Plonsker, *J. Am. Soc.*, 83, 2138 (1961).

Alternatively, cyclopropyl-esters trans/cis-(IX), wherein B is as defined under formula I, can be prepared by the reaction of diazomethane with an alkyl cinnamate of formula XI, wherein B is as defined under formula I, in the presence of $Pd(OAc)_2$ as described by U. Mende et al. *THL No.* 9, 629-632, 1975. Such cyclopropanations with diazomethane and chiral palladium(II) complexes are also described by Scott E. Denmark et al. *J. Org. Chem.* 1997, 62, 3375-3389. The trans-2-arylcyclopropylamines of formula trans-(IIB) can then be prepared from the cyclopropyl-esters trans/cis-(IX) as described above.

Intermediates of the Formula IIC

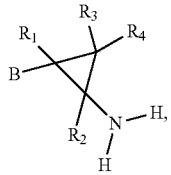

(IIC)

in which B is as defined under formula I and (II), $R_1$ is hydrogen, halogen, cyano, $C_1$-$C_6$alkyl, which is unsubstituted or substituted by one or more substituents $R^a$, or $C_3$-$C_6$cycloalkyl, which is unsubstituted or substituted by one or more substituents $R^a$, wherein each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio or $C_1$-$C_6$halogenalkylthio;

$R_2$ is hydrogen, cyano, nitro, $C_1$-$C_6$alkyl, which is unsubstituted or substituted by one or more substituents $R^a$, or $C_3$-$C_6$cycloalkyl, which is unsubstituted or substituted by one or more substituents $R^a$; wherein each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio or $C_1$-$C_6$halogenalkylthio;

$R_3$ and $R_4$ independently of each other stand for hydrogen, cyano, nitro, $C_1$-$C_6$alkyl, which is unsubstituted or substituted by one or more substituents $R^a$, or $C_{3-6}$cycloalkyl, which is unsubstituted or substituted by one or more substituents $R^a$; wherein each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio or $C_1$-$C_6$halogenalkylthio;

may be prepared by reaction scheme 2.

Scheme 2:

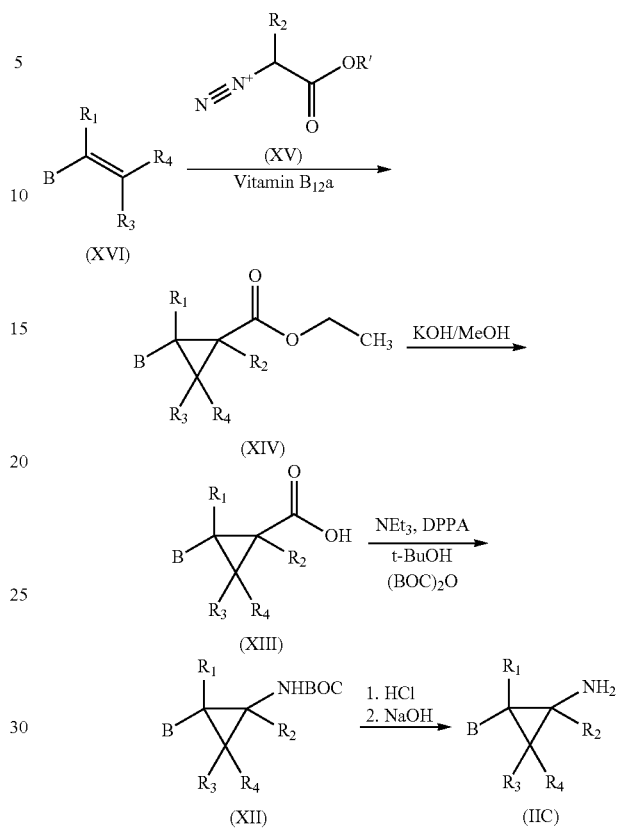

According to scheme 2, reaction of compounds of formula XVI, wherein $R_1$, $R_3$, $R_4$ and B are as defined under formula IIC, with alkyldiazoacetate derivatives of formula XV, wherein $R_2$ is as defined under formula IIC and R' is $C_1$-$C_6$alkyl, and Vitamin $B_{12}$a as catalyst (Y. Chen and X. P. Zhang, J. Org. Chem. 2004, 69, 2431-2435), gives a diastereomeric mixture of cyclopropylcarboxylates of formula XIV, wherein $R_1$, $R_2$, $R_3$, $R_4$ and B are as defined under formula IIC. The diastereomers can be separated either chromatographically or, after saponification, by recrystallisation of the corresponding carboxylic acids of formula XIII, wherein $R_1$, $R_2$, $R_3$, $R_4$ and B are as defined under formula IIC. Curtius degradation to the BOC-protected amines of formula XII, wherein $R_1$, $R_2$, $R_3$, $R_4$ and B are as defined under formula IIC, and deprotection with hydrogen chloride produces the compounds of formula IIC in the form of hydrochlorides (see PCT/US2004/021505 and G. Haufe et al, J. Med. Chem. 2004, 47, 5860-5871). The cis and trans isomers of (XIV) or (XII) may be separated by chromatography.

The reactions are carried out at temperatures of between 0-100° C. in a convenient organic solvent such as methanol, ethanol, tert-butanol, trifluoroethanol, chloroform, dichloromethane or dioxane.

Other catalysts such as copper acetate can be used as an alternative to Vitamin $B_{12}$a for the cyclopropanation reaction.

The Curtius rearrangement of the carboxylic acids of formula XIII to the BOC-protected amines of formula XIII can be carried out using diphenylphosphoryl azide with a convenient base such as triethylamine followed by treatment with di-tert-butyl carbonate (D. Kim and S. M. Weinreb, J. Org. Chem. 1978, 43, 125-131). The BOC protecting group can be removed by sequential acid and base treatment.

Compounds of the formulae VIII, X, XI or XVI, all wherein B is a phenyl group, which is substituted by one or more substituents $R_9$, are known and are commercially available or can be prepared according to the above-mentioned references or according to methods known in the art.

Compounds of the formula III are known and partially commercially available. They can be prepared analogously as described, for example, in WO 00/09482, WO 02/38542, WO 04/018438, EP-0-589-301, WO 93/11117 and Arch. Pharm. Res. 2000, 23(4), 315-323.

The compounds of formula VII, V, and XV are known and are commercially available or can be prepared according to the above-mentioned references or according to methods known in the art.

Compounds of the formula XVII

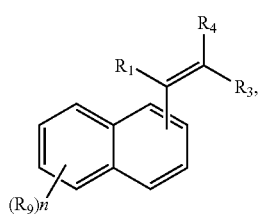

(XVII)

wherein $R_9$ is as defined under formula I; n is 1, 2, 3, 4, 5, 6 or 7, preferably 1 or 2; $R_1$ is hydrogen, cyano, $C_1$-$C_6$alkyl, which is unsubstituted or substituted by one or more substituents $R^a$, or $C_3$-$C_6$cycloalkyl, which is unsubstituted or substituted by one or more substituents $R^a$, wherein each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio or $C_1$-$C_6$halogenalkylthio; and $R_3$ and $R_4$ independently of each other stand for hydrogen, cyano, nitro, $C_1$-$C_6$alkyl, which is unsubstituted or substituted by one or more substituents $R^a$, or $C_3$-$C_6$cycloalkyl, which is unsubstituted or substituted by one or more substituents $R^a$; wherein each $R^a$ independently of each other stand for halogen, cyano, nitro, $C_1$-$C_6$alkoxy, $C_1$-$C_6$halogenalkoxy, $C_3$-$C_6$cycloalkyl, $C_1$-$C_6$alkylthio or $C_1$-$C_6$halogenalkylthio; can be prepared according to reaction scheme 3 or in analogy to reaction scheme 3. Said compounds of formula XVII correspond to compounds of formula X or XVI, wherein B is a naphthyl group, which is substituted by one or more substituents $R_9$, with the exception of compounds according to formula XVI, wherein $R_1$ is halogen.

Scheme 3:

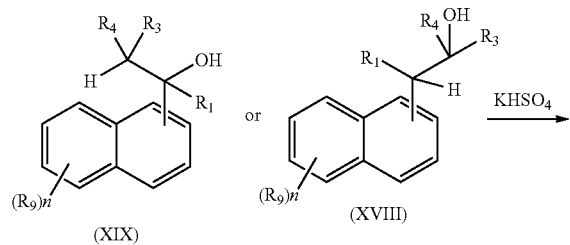

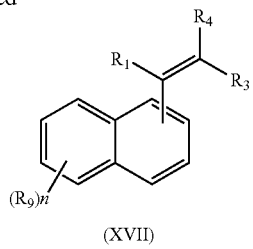

(XVII)

According to scheme 3, compounds of the formula XVII, wherein $R_9$, n, $R_1$, $R_3$ and $R_4$ are as defined above, can be prepared from compounds of formula XVIII, wherein $R_9$, n, $R_1$, $R_3$ and $R_4$ are as defined under formula XVII, or from compounds of formula XIX, wherein $R_9$, n, $R_1$, $R_3$ and $R_4$ are as defined under formula XVII, by alcohol-dehydration over $KHSO_4$ according to Charles C. Price et al. *J Org Chem* (1949), 14 111-117.

Compounds of the Formula XX

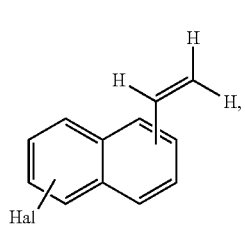

(XX)

wherein Hal is F or Cl; can be prepared according to scheme 4. Compounds of formula XX form a sub-group of compounds of formula X or XVI.

Scheme 4:

Monohalogen-vinylnaphtalenes of formula XX, wherein Hal is F or Cl, can be prepared by a palladium-catalyzed vinylation of the naphthyl bromides of formula XXI, wherein Hal is F or Cl, using TBAF as activator and an inexpensive and non-toxic vinyl donor, such as 1,3,5,7-tetramethyl-1,3,5,7-tetravinylcyclotetrasiloxane, as published by Scott E. Denmark *Organic Letters* 2006 Vol. 8, No. 1 63-66.

Furthermore, the synthesis of 6-chloro-2-vinyinaphthalene is known, see *J. Am. Chem. Soc.*, (1948), 70, 4265-4266.

Compounds of the formulae XIX, XVIII and XXI are known and are commercially available or can be prepared according to the above-mentioned references or according to methods known in the art.

Compounds of the formula XXII or XXIII

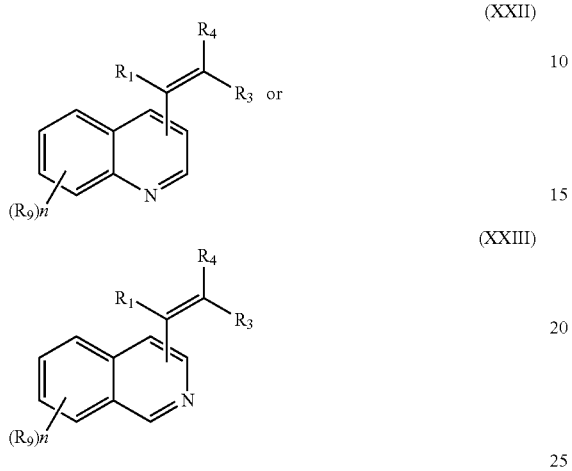

wherein $R_9$ is as defined under formula I; n is 1, 2, 3, 4, 5 or 6, preferably 1 or 2; and $R_1$, $R_3$ and $R_4$ are as defined under formula XVI, can be prepared according to reaction scheme 5 or in analogy to reaction scheme 5. Said compounds of formula XXII and XXIII correspond to compounds of formula X or XVI, wherein B is a quinolinyl group, which is substituted by one or more substituents $R_9$.

Scheme 5:

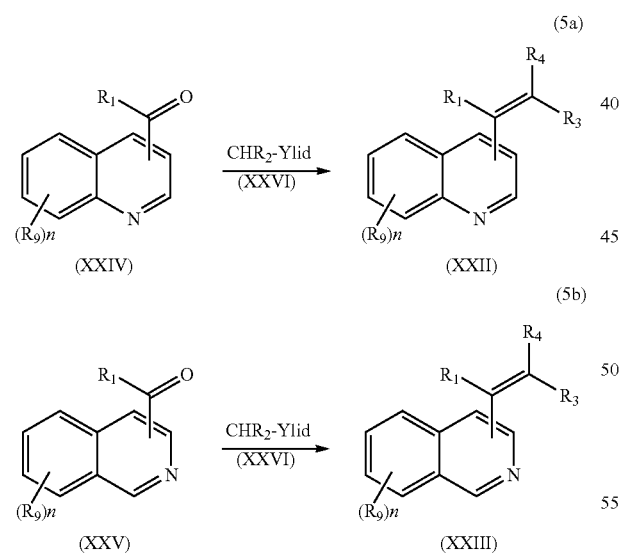

According to scheme 5, compounds of the formula XXII and XXIII, wherein $R_9$, n, $R_1$, $R_3$ and $R_4$ are as defined above, can be prepared from compounds of formula XXIV and XXV, respectively via a Wittig-reaction with compounds of formula XXVI, wherein $R_2$ is as defined under formula I.

Compounds of the formulae XXIV and XXV are known and are commercially available or can be prepared from known precursors according to methods known in the art. Especially, some monochloro-substituted 4-quinolinecarboxaldehydes and monochlorosubstituted 3-quinolinecarboxaldehydes are commercially available or known, for example, compounds XXIVa to XXIVj are registered under the following CAS-registry numbers.

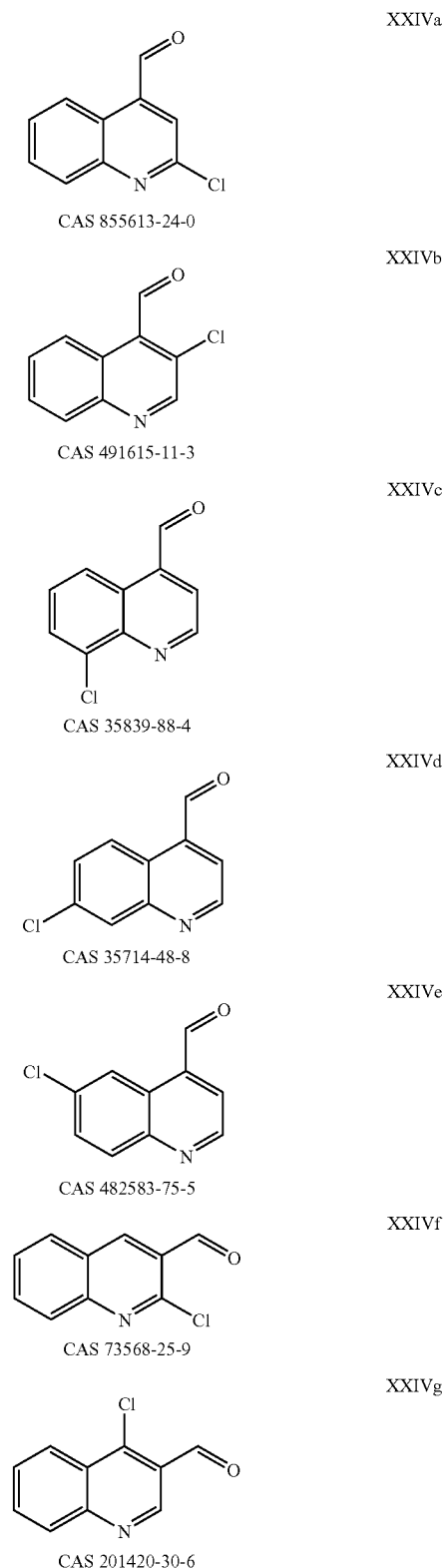

-continued

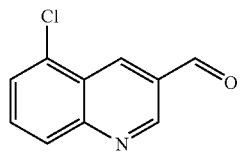
CAS 457614-14-1

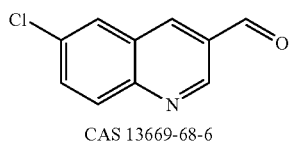
CAS 13669-68-6

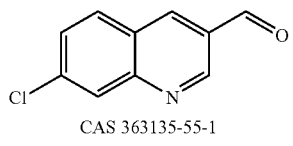
CAS 363135-55-1

Compounds according to Formula ID

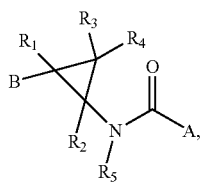
(ID)

wherein A and B are as defined in $R_5$ is $C_{1-4}$ alkyl, $CH_2CH=CHR_{5a}$, $CH_2C\equiv CR_{5b}$ or $COR_{5c}$; $R_{5a}$ and $R_{5b}$ are each, independently, hydrogen, $C_1$-$C_6$alkyl, $C_1$-$C_6$halogenalkyl, $C_2$-$C_6$alkenyl, $C_2$-$C_6$alkynyl, $C_3$-$C_7$cycloalkyl, $COOC_1$-$C_4$alkyl, $COOC_3$-$C_6$alkenyl, $COOC_3$-$C_6$alkynyl or CN; $R_{5c}$ is hydrogen, $C_1$-$C_6$alkyl, $C_1$-$C_6$halogenalkyl, $C_1$-$C_6$alkoxy-$C_1$-$C_6$alkyl, $C_1$-$C_6$halogenalkoxy-$C_1$-$C_6$alkyl, $C_1$-$C_6$alkylthio, $C_1$-$C_6$halogenalkylthio, $C_1$-$C_6$alkoxy, $C_1$-$C_6$halogenalkoxy, $C_3$-$C_6$alkenyloxy, $C_3$-$C_6$halogenalkenyloxy, $C_3$-$C_6$alkynyloxy or $C_3$-$C_6$halogenalkynyloxy; may be prepared according to reaction scheme 6.

Scheme 6:

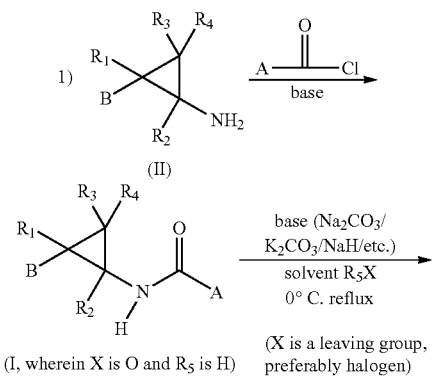

-continued

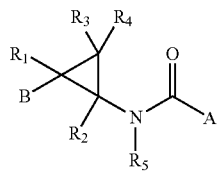
(I, wherein X is O)

or $R_5X$
base
solvent
0° C. - reflux
base: $Na_2CO_3$/
$K_2CO_3$/$N(R)_3$
solvent: dioxane, THF, for alkylations also alcohols, hexane cyclohexane, toluene or other aromatic solvents

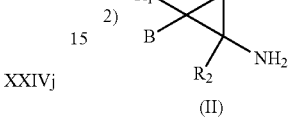

base($Na_2CO_3$, $K_2CO_3$, NaH)
solvent (ethers, $CH_2Cl_2$, CHCl_3, toluene, hexane, cyclohexane)
0° C. - reflux

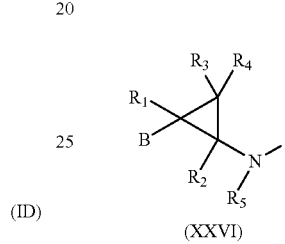
(XXVI)

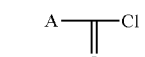

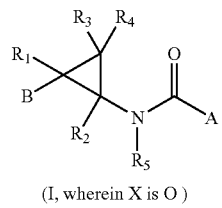
(I, wherein X is O)

In compounds of formula XXVI B, $R_1$, $R_2$, $R_3$, $R_4$ and $R_5$ are as defined under formula IID.

Compounds of formula I, wherein X is sulfur, can be prepared from compounds of formula I, wherein X is oxygen, for example by reaction with $P_2S_5$ in an inert solvent, such as benzene, toluene, tetrahydrofurane, dioxane or mixtures thereof.

The compounds of the formula III are known and partially commercially available. They can be prepared analogously as described, for example, in WO 00/09482, WO 02/38542, WO 04/018438, EP-O-589-301, WO 93/11117 and Arch. Pharm. Res. 2000, 23(4), 315-323.

The compounds of formula VII, V, XI and XII are known and are commercially available or can be prepared according to the above-mentioned references or according to methods known in the art.

For preparing all further compounds of the formula I functionalized according to the definitions of A, B, X, $R_1$, $R_2$, $R_3$, $R_4$ and $R_5$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants:

cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid [2-(4-chlorophenyl)-cyclopropyl]-amide (Compound No. 1.001)

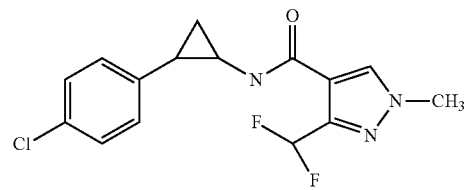 [SMILES: Cn1cc(C(=O)NC2CC2c2ccc(Cl)cc2)c(C(F)F)n1]

The crude amine Z1.001 from Example P4 was suspended in dichloromethane (10 ml) and triethylamine (250 mg, 2.5 mmol). To this suspension was added at 0° C. a solution of 3-difluoromethyl-1-methyl-1H-pyrazole-4-carbonyl chloride (194 mg, 1.0 mmol) in dichloromethane (2 ml) and stirred for one hour. After removal of the solvent the residue was purified by flash chromatography over silica gel (eluant: hexane/ethyl acetate 1:9). Yield: 92 mg (28.2% of theory) of the cis-isomer of 3-difluoromethyl-1-methyl-1H-pyrazole-4-carboxylic acid [2-(4-chlorophenyl)-cyclopropyl]-amide (compound no. 1.001) in form of a solid m.p. 127° C.

$^1$H NMR (400 MHz, CDCl$_3$): δ1.06-1.17 (m, 1H, CHH), 1.44 (q, 1H, CHH), 2.32-2.38 (q, 1H, CHAr), 3.23-3.29 (m, 1H, CHN), 3.73 (s, 3H, NCH$_3$), 6.08 (s, 1H, NH), 6.48-6.75 (t, 1H, CHF$_2$), 7.14-7.17 (d, 2H, Ar—H), 7.20-7.23 (d, 2H, Ar—H), 7.70 (s, 1H, Pyrazol-H). MS [M+H]$^+$ 326/328.

Example P2

Preparation of 3-difluoromethyl-1-methyl-1H-pyrazole-4-carboxylic acid (2-(4-chlorophenyl)-2-fluoro-cyclopropyl)-amide (Compound No. 1.004)

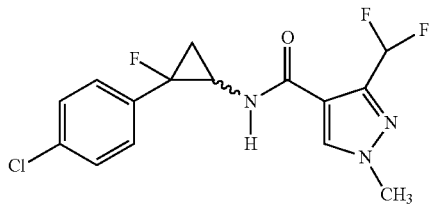 [SMILES: Cn1cc(C(=O)NC2CC2(F)c2ccc(Cl)cc2)c(C(F)F)n1]

A solution of 3-difluoromethyl-1-methyl-1H-pyrazole-4-carbonyl chloride (0.105 g; 0.54 mmol) in dichloromethane (2 ml) was added dropwise to a stirred solution of the amine from example P5 (compound Z1.004; 2-(4-chlorophenyl)-2-fluoro-cyclopropylamine; 0.100 g; 0.54 mmol) and triethylamine (0.15 ml; 1.08 mmol) in dichloromethane (3 ml). The reaction mixture was stirred for 1 hr at ambient temperature then allowed to stand for 18 h. The reaction mixture was washed with 2M HCl (5 ml) and with saturated NaHCO$_3$ (5 ml) and then dried over MgSO$_4$. Evaporation of the solvent yielded 0.15 g 3-difluoromethyl-1-methyl-1H-pyrazole-4-carboxylic acid (2-(4-chlorophenyl)-2-fluoro-cyclopropyl)-amide in the form of a yellow solid (81% of theory) as a 7:3 mixture of cis/trans isomers.

$^1$HNMR (400 MHz, CDCl$_3$): Cis isomer: 1.50δ (m; 1H): 1.92δ (ddd; 1H): 3.62δ (m; 1H): 3.85δ (s; 3H): 6.05δ (br-s; 1H): 6.60δ (t; 1H): 7.30δ-7.40δ (m; 4H): 7.80δ (s; 1H). Trans isomer: 1.57δ (m; 1H): 1.67δ (ddd; 1H): 3.32δ (m; 1H): 6.70δ (br-s; 1H): 6.85δ (t; 1H) 7.30δ-7.40δ (m; 4H): 7.95δ (s; 1H).

Example P3

Preparation of N-[(1R,2S)-2-(4-chlorophenyl)-2-fluoro-cyclopropyl]-2-trifluoromethyl-benzamide (Compound No. 6.004)

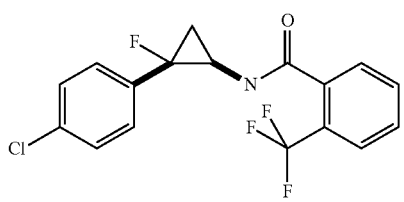

A solution of 2-trifluoromethylbenzoyl chloride (0.10 g; 0.54 mmol) in dichloromethane (2 ml) added dropwise to a stirred solution of the amine from example P5 (compound Z1.004; 2-(4-chlorophenyl)-2-fluoro-cyclopropylamine; 0.100 g; 0.54 mmol) and triethylamine (0.15 ml; 1.08 m) in dichloromethane (3 ml). Stirred for 1 hr at room temperature then allowed to stand for 18 hr. The white precipitate was filtered off, washed with 2M HCl, saturated NaHCO$_3$ and water and air dried giving the pure cis isomer. 0.065 g (34%).

$^1$HNMR (400 MHz, CDCl$_3$): 1.60δ (m; 1H): 1.97δ (ddd; 1H): 3.67δ (m; 1H): 5.40δ (br-s; 1H): 7.10δ-7.65δ (m; 8H). MH$^+$ 358. MP 204-206°.

The dichloromethane soluble material consisted of a 1:1 mixture of cis/trans isomers.

Example P4

Preparation of (1R,2R)-2-(4-chloro-phenyl)-cyclopropylamine (Compound No. Z1.001)

a) Preparation of 4-chlorobenzaldehyde tosyl hydrazone

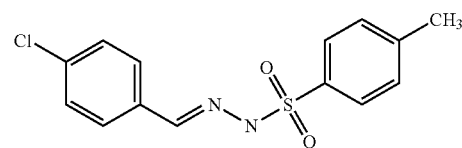 [SMILES: Cc1ccc(S(=O)(=O)N/N=C/c2ccc(Cl)cc2)cc1]

To a stirred suspension of p-toluenesulfonyl hydrazide (5.0 g, 26.8 mmol) in methanol (20 ml) 4-chloro-benzaldehyde (3.3 g, 23.3 mol) was added dropwise. After 0.h hour the mixture was cooled to 0° C. and the product removed by filtration, washed with cold methanol (10 ml) and then crystallized from hot methanol to give 5.5 g (76.5% of theory) 4-chlorobenzaldehyde tosyl hydrazone in the form of a white solid.

$^1$H NMR (400 MHz, DMSO): δ 11.5 (S$_{broad}$, 1H), 7.91 (s, 1H), 7.77 (d, 2H), 7.57 (d, 2H), 7.44 (d, 2H), 7.49 (d, 2H), 2.35 (s, 3H).

b) Preparation of 4-chlorobenzaldehyde tosyl hydrazone sodium salt

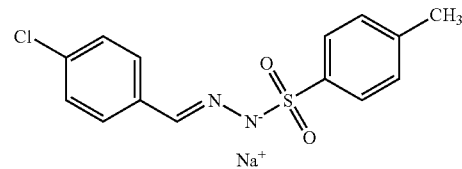 [SMILES: Cc1ccc(S(=O)(=O)[N-]/N=C/c2ccc(Cl)cc2)cc1 ; [Na+]]

A 1 M sodium methoxyde solution was prepared by adding sodium (423 mg, 18.39 mmol) to anhydrous methanol (19 ml) with external cooling. Once all of the metal was dissolved, 4-chlorobenzaldehyde tosyl hydrazone (5.39 g, 17.51 mmol) was added and the mixture was stirred until the solid was dissolved. After stirring for a further 15 min at room temperature the methanol was removed under reduced pressure at room temperature. 5.73 g of 4-chlorobenzaldehyde tosyl hydrazone sodium salt was obtained in the form of a white powder (99% of theory).

c) Preparation of 2-[(1R,2R)-2-(4-chloro-phenyl)-cyclopropyl]-isoindole-1,3-dione

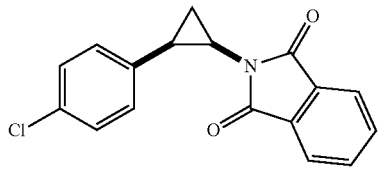

A mixture of 4-chlorobenzaldehyde tosyl hydrazone sodium salt (1.67 g, 5.05 mmol), benzyltriethylammonium-chloride (115 mg, 0.5 mmol), rhodium acetate (20 mg, 0.05 mmol) and N-vinylphtalimide (4.32 g, 25.0 mmol) in dry 1,4-dioxane (13 ml) was stirred for one day under nitrogen at room temperature. Water (35 ml) was added to the mixture and the aqueous phase was extracted three times with dichloromethane. The combined organic layers were dried over Na$_2$SO$_4$. Evaporation gave the crude material, which was purified by flash chromatography over silicagel (eluent: hexane/ethylacetate 1:1). To afford 392 mg (26.3% of theory) of 2-[2-(4-chloro-phenyl)-cyclopropyl]-isoindole-1,3-dione in the form of a solid.

$^1$H NMR (400 MHz, CDCl$_3$): δ 7.73-7.62 (m, 4H), 7.04-7.01 (m, 4H), 3.08 (td, 1H, CHN), 2.50 (q, 1H, CHPh), 2.19 (ddd, 1H, CHH), 1.63 (q, 1H, CHH).

MS [M+H]$^+$ 298/300.

d) Preparation of (1R,2R)-2-(4-chloro-phenyl)-cyclopropylamine (Compound No. Z1.001)

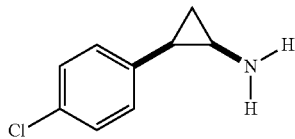 [SMILES: N[C@@H]1C[C@@H]1c1ccc(Cl)cc1]

A mixture of 2-[2-(4-chloro-phenyl)-cyclopropyl]-isoindole-1,3-dione (320 mg, 1.07 mmol) and hydrazine hydrate (0.5 ml) in ethanol (8 ml) was stirred for 0.5 hour at 50° C. The solution was evaporated under reduced pressure. The resulting amine (compound Z1.001) was used in example P1 without further purification.

Example P5

Preparation of 2-(4-chlorophenyl)-2-fluoro-cyclopropylamine (Compound No. Z1.004)

a) Preparation of 2-(4-chlorophenyl)-2-fluoro-cyclopropane carboxylic acid ethyl ester

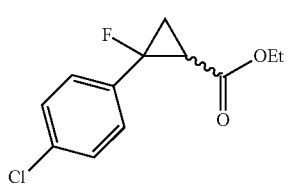 [SMILES: CCOC(=O)C1CC1(F)c1ccc(Cl)cc1]

Vitamin B12a (1.00 g; 0.723 mmol) was dissolved in dry trifluoroethanol (70 ml) and 1-chloro-4-(1-fluoro-vinyl)-benzene (6.50 g; 41.5 mmol) and ethyl diazoacetate (6.30 g; 50 mmol; 90% purity) was added. The solution was stirred, under reflux, under nitrogen atmosphere for 18 h. After cooling the solvent was evaporated and the residue purified by flash chromatography using 9:1 hexane/ethyl acetate. 6.9 g of 2-(4-chlorophenyl)-2-fluoro-cyclopropane carboxylic acid ethyl ester was obtained in the form of an oil (81% of theory) as a 7:3 mixture of cis/trans isomers.

$^1$H NMR (400 MHz, CDCl3): cis isomer: 1.05δ (t; 3H): 1.82δ (ddd; 1H): 1.95δ (ddd; 1H): 2.57δ (ddd; 1H): 3.95δ (m; 2H): 7.20δ-7.42δ (m; 4H). Trans isomer: 1.30δ (t; 3H): 1.60δ (ddd; 1H): 2.17δ (ddd; 1H): 2.30δ (ddd; 1H): 4.25δ (m; 2H): 7.20δ-7.42δ (m; 4H).

b) Preparation of 2-(4-chlorophenyl)-2-fluoro-cyclopropanecarboxylic acid

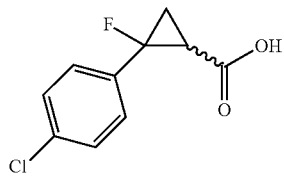 [SMILES: O=C(O)C1CC1(F)c1ccc(Cl)cc1]

The ester from example P5a) (6.90 g; 28 mmol) was added dropwise to a stirred solution of KOH in methanol (0.956M; 300 ml; 0.28 m) with ice/water cooling. The solution was then stirred at room temperature for 18 h and concentrated under reduced pressure at room temperature. The residue was mixed with cold water and extracted with dichloromethane. The aqueous portion was acidified with concentrated HCl with ice cooling and extracted twice with dichloromethane. The extracts were dried (MgSO$_4$) and evaporated. 5.10 g of 2-(4-chlorophenyl)-2-fluoro-cyclopropanecarboxylic acid was obtained in the form of a yellow solid (85% of theory) as a 7:3 mixture of cis/trans isomers.

$^1$HNMR (400 MHz, CDCl$_3$): cis isomer: 1.85δ-2.00δ (m; 2H): 2.55δ (ddd; 1H); 7.20δ-7.40δ (m; 4H). Trans isomer: 1.67δ (ddd; 1H): 2.12δ (ddd; 1H): 2.30δ (ddd; 1H): 7.20δ-7.40δ (m; 4H).

c) Preparation of (2-(4-chlorophenyl)-2-fluoro-cyclopropyl)-carbamic acid tert-butyl ester

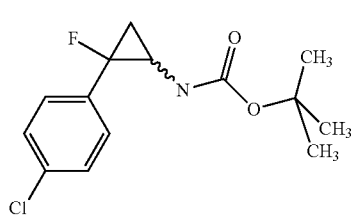 [SMILES: CC(C)(C)OC(=O)NC1CC1(F)c1ccc(Cl)cc1]

The carboxylic acid from example P5b) (5.09 g; 23.7 mmol) was dissolved in a mixture of cyclohexane (150 ml) and tert-butanol (17.70 g; 0.237 m). Triethylamine (2.86 g; 0.0284 m) and diphenylphosphoryl azide (7.30 g; 0.0262 m) were added and the solution stirred under reflux under nitrogen for 18 h. After cooling, di-tert-butyl carbonate (7.86 g; 0.0359 m) was added and the mixture stirred under reflux for 2 h. After cooling the mixture was diluted with ethyl acetate (200 ml) and washed with 5% citric acid solution (50 ml) followed by saturated NaHCO$_3$ solution. The extract was dried (MgSO$_4$) and evaporated. The oily residue was triturated with pentane (50 ml) and the white solid filtered off and recrystallized from hexane. 4.3 g of (2-(4-chlorophenyl)-2-fluoro-cyclopropyl)-carbamic acid tert-butyl ester was obtained in the from of a white solid (63% of theory) as a 7:3 mixture of cis/trans isomers.

$^1$HNMR (400 MHz, CDCl$_3$): cis isomer: 1.32δ (s; 9H): 1.42δ (m; 1H): 1.80δ (ddd; 1H): 3.30δ (m; 1H): 4.25δ (br-s; 1H): 7.30δ-7.40δ (m; 4H). Trans isomer: 1.40δ (m; 1H): 1.50δ (s; 9H): 2.97δ (m; 1H): 4.95δ (br-s; 1H): 7.30δ-7.40δ (m; 4H).

d) Preparation of 2-(4-chlorophenyl)-2-fluoro-cyclopropylamine (Compound No. Z1.004)

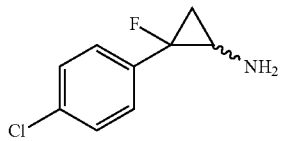 [SMILES: NC1CC1(F)c1ccc(Cl)cc1]

(2-(4-chlorophenyl)-2-fluoro-cyclopropyl)-carbamic acid tert-butyl ester from example P5c) (1.00 g; 3.5 mmol) was dissolved in methanol (10 ml) and a saturated solution of HCl in ethanol (10 ml) added. The solution was stirred at room temperature for 2 h then evaporated leaving a white solid. Water (50 ml) then added and mixture extracted twice with ethyl acetate. The aqueous phase was made alkaline with 2M NaOH and extracted twice with ethyl acetate. The extracts were dried (MgSO$_4$) and evaporated. 0.60 g of 2-(4-chlorophenyl)-2-fluoro-cyclopropylamine was obtained in the form of a yellow oil (92% of theory) as a 7:3 mixture of cis/trans isomers.

$^1$HNMR (400 MHz, CDCl$_3$): cis isomer: 1.15δ (ddd; 1H): 1.60δ (ddd; 1H): 3.10δ (ddd; 1H): 7.30δ-7.455 (m; 4H). Trans isomer: 1.27δ (ddd; 1H): 1.40δ (m; 1H): 2.57δ (ddd; 1H): 7.10δ-7.30δ (m; 4H).

Tables 1 to 8: Compounds of Formula IA

The invention is further illustrated by the preferred individual compounds of formula (IA) listed below in Tables 1 to 8. Characterising data is given in Table 18.

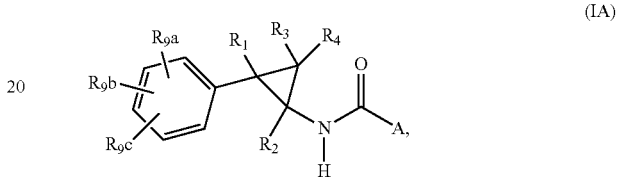

(IA)

Each of Tables 1 to 8, which follow the Table Y below, comprises 274 compounds of the formula (IA) in which $R_1$, $R_2$, $R_3$, $R_4$, $R_{9a}$, $R_{9b}$ and $R_{9c}$ have the values given in Table Y and A has the value given in the relevant Table 1 to 8. Thus Table 1 corresponds to Table Y when Y is 1 and A has the value given under the Table 1 heading, Table 2 corresponds to Table Y when Y is 2 and A has the value given under the Table 2 heading, and so on for Tables 3 to 8.

TABLE Y

| Cpd No. | $R_1$ | $R_2$ | $R_3$ | $R_4$ | $R_{9a}$ | $R_{9b}$ | $R_{9c}$ |
|---|---|---|---|---|---|---|---|
| Y.001 | H | H | H | H | 4-Cl | H | H |
| Y.002 | CH$_3$ | H | H | H | 4-Cl | H | H |
| Y.003 | CH$_2$CH$_3$ | H | H | H | 4-Cl | H | H |
| Y.004 | F | H | H | H | 4-Cl | H | H |
| Y.005 | CN | H | H | H | 4-Cl | H | H |
| Y.006 | H | CH$_3$ | H | H | 4-Cl | H | H |
| Y.007 | CH$_3$ | CH$_3$ | H | H | 4-Cl | H | H |
| Y.008 | CH$_2$CH$_3$ | CH$_3$ | H | H | 4-Cl | H | H |
| Y.009 | F | CH$_3$ | H | H | 4-Cl | H | H |
| Y.010 | CN | CH$_3$ | H | H | 4-Cl | H | H |
| Y.011 | H | CH$_2$CH$_3$ | H | H | 4-Cl | H | H |
| Y.012 | CH$_3$ | CH$_2$CH$_3$ | H | H | 4-Cl | H | H |
| Y.013 | F | CH$_2$CH$_3$ | H | H | 4-Cl | H | H |
| Y.014 | CN | CH$_2$CH$_3$ | H | H | 4-Cl | H | H |
| Y.015 | H | H | F | H | 4-Cl | H | H |
| Y.016 | CH$_3$ | H | F | H | 4-Cl | H | H |
| Y.017 | F | H | F | H | 4-Cl | H | H |
| Y.018 | H | CH$_3$ | F | H | 4-Cl | H | H |
| Y.019 | CH$_3$ | CH$_3$ | F | H | 4-Cl | H | H |
| Y.020 | F | CH$_3$ | F | H | 4-Cl | H | H |
| Y.021 | H | H | F | F | 4-Cl | H | H |
| Y.022 | CH$_3$ | H | F | F | 4-Cl | H | H |
| Y.023 | F | H | F | F | 4-Cl | H | H |
| Y.024 | H | CH$_3$ | F | F | 4-Cl | H | H |
| Y.025 | CH$_3$ | CH$_3$ | F | F | 4-Cl | H | H |
| Y.026 | F | CH$_3$ | F | F | 4-Cl | H | H |
| Y.027 | H | H | H | H | 4-CF$_3$ | H | H |
| Y.028 | CH$_3$ | H | H | H | 4-CF$_3$ | H | H |
| Y.029 | CH$_2$CH$_3$ | H | H | H | 4-CF$_3$ | H | H |
| Y.030 | F | H | H | H | 4-CF$_3$ | H | H |
| Y.031 | CN | H | H | H | 4-CF$_3$ | H | H |
| Y.032 | H | CH$_3$ | H | H | 4-CF$_3$ | H | H |
| Y.033 | CH$_3$ | CH$_3$ | H | H | 4-CF$_3$ | H | H |
| Y.034 | CH$_2$CH$_3$ | CH$_3$ | H | H | 4-CF$_3$ | H | H |
| Y.035 | F | CH$_3$ | H | H | 4-CF$_3$ | H | H |
| Y.036 | CN | CH$_3$ | H | H | 4-CF$_3$ | H | H |

TABLE Y-continued

| Cpd No. | R₁ | R₂ | R₃ | R₄ | R_{9a} | R_{9b} | R_{9c} |
|---|---|---|---|---|---|---|---|
| Y.037 | H | CH₂CH₃ | H | H | 4-CF₃ | H | H |
| Y.038 | CH₃ | CH₂CH₃ | H | H | 4-CF₃ | H | H |
| Y.039 | F | CH₂CH₃ | H | H | 4-CF₃ | H | H |
| Y.040 | CN | CH₂CH₃ | H | H | 4-CF₃ | H | H |
| Y.041 | H | H | F | H | 4-CF₃ | H | H |
| Y.042 | CH₃ | H | F | H | 4-CF₃ | H | H |
| Y.043 | F | H | F | H | 4-CF₃ | H | H |
| Y.044 | H | CH₃ | F | H | 4-CF₃ | H | H |
| Y.045 | CH₃ | CH₃ | F | H | 4-CF₃ | H | H |
| Y.046 | F | CH₃ | F | H | 4-CF₃ | H | H |
| Y.047 | H | H | F | F | 4-CF₃ | H | H |
| Y.048 | CH₃ | H | F | F | 4-CF₃ | H | H |
| Y.049 | F | H | F | F | 4-CF₃ | H | H |
| Y.050 | H | CH₃ | F | F | 4-CF₃ | H | H |
| Y.051 | CH₃ | CH₃ | F | F | 4-CF₃ | H | H |
| Y.052 | F | CH₃ | F | F | 4-CF₃ | H | H |
| Y.053 | H | H | H | H | 4-OCF₃ | H | H |
| Y.054 | CH₃ | H | H | H | 4-OCF₃ | H | H |
| Y.055 | CH₂CH₃ | H | H | H | 4-OCF₃ | H | H |
| Y.056 | F | H | H | H | 4-OCF₃ | H | H |
| Y.057 | CN | H | H | H | 4-OCF₃ | H | H |
| Y.058 | H | CH₃ | H | H | 4-OCF₃ | H | H |
| Y.059 | CH₃ | CH₃ | H | H | 4-OCF₃ | H | H |
| Y.060 | CH₂CH₃ | CH₃ | H | H | 4-OCF₃ | H | H |
| Y.061 | F | CH₃ | H | H | 4-OCF₃ | H | H |
| Y.062 | CN | CH₃ | H | H | 4-OCF₃ | H | H |
| Y.063 | H | CH₂CH₃ | H | H | 4-OCF₃ | H | H |
| Y.064 | CH₃ | CH₂CH₃ | H | H | 4-OCF₃ | H | H |
| Y.065 | F | CH₂CH₃ | H | H | 4-OCF₃ | H | H |
| Y.066 | CN | CH₂CH₃ | H | H | 4-OCF₃ | H | H |
| Y.067 | H | H | F | H | 4-OCF₃ | H | H |
| Y.068 | CH₃ | H | F | H | 4-OCF₃ | H | H |
| Y.069 | F | H | F | H | 4-OCF₃ | H | H |
| Y.070 | H | CH₃ | F | H | 4-OCF₃ | H | H |
| Y.071 | CH₃ | CH₃ | F | H | 4-OCF₃ | H | H |
| Y.072 | F | CH₃ | F | H | 4-OCF₃ | H | H |
| Y.073 | H | H | F | F | 4-OCF₃ | H | H |
| Y.074 | CH₃ | H | F | F | 4-OCF₃ | H | H |
| Y.075 | F | H | F | F | 4-OCF₃ | H | H |
| Y.076 | H | CH₃ | F | F | 4-OCF₃ | H | H |
| Y.077 | CH₃ | CH₃ | F | F | 4-OCF₃ | H | H |
| Y.078 | F | CH₃ | F | F | 4-OCF₃ | H | H |
| Y.079 | H | H | H | H | 4-F | H | H |
| Y.080 | F | H | H | H | 4-F | H | H |
| Y.081 | H | CH₃ | H | H | 4-F | H | H |
| Y.082 | F | CH₃ | H | H | 4-F | H | H |
| Y.083 | H | CH₂CH₃ | H | H | 4-F | H | H |
| Y.084 | H | H | F | H | 4-F | H | H |
| Y.085 | F | H | F | H | 4-F | H | H |
| Y.086 | H | CH₃ | F | H | 4-F | H | H |
| Y.087 | F | CH₃ | F | H | 4-F | H | H |
| Y.088 | H | H | F | F | 4-F | H | H |
| Y.089 | F | H | F | F | 4-F | H | H |
| Y.090 | F | CH₃ | F | F | 4-F | H | H |
| Y.091 | H | H | H | H | 4-p-Cl-phenyl | H | H |
| Y.092 | CH₃ | H | H | H | 4-p-Cl-phenyl | H | H |
| Y.093 | CH₂CH₃ | H | H | H | 4-p-Cl-phenyl | H | H |
| Y.094 | F | H | H | H | 4-p-Cl-phenyl | H | H |
| Y.095 | CN | H | H | H | 4-p-Cl-phenyl | H | H |
| Y.096 | H | CH₃ | H | H | 4-p-Cl-phenyl | H | H |
| Y.097 | CH₃ | CH₃ | H | H | 4-p-Cl-phenyl | H | H |
| Y.098 | CH₂CH₃ | CH₃ | H | H | 4-p-Cl-phenyl | H | H |
| Y.099 | F | CH₃ | H | H | 4-p-Cl-phenyl | H | H |
| Y.100 | CN | CH₃ | H | H | 4-p-Cl-phenyl | H | H |
| Y.101 | H | CH₂CH₃ | H | H | 4-p-Cl-phenyl | H | H |
| Y.102 | CH₃ | CH₂CH₃ | H | H | 4-p-Cl-phenyl | H | H |
| Y.103 | F | CH₂CH₃ | H | H | 4-p-Cl-phenyl | H | H |
| Y.104 | CN | CH₂CH₃ | H | H | 4-p-Cl-phenyl | H | H |
| Y.105 | H | H | F | H | 4-p-Cl-phenyl | H | H |
| Y.106 | CH₃ | H | F | H | 4-p-Cl-phenyl | H | H |
| Y.107 | F | H | F | H | 4-p-Cl-phenyl | H | H |
| Y.108 | H | CH₃ | F | H | 4-p-Cl-phenyl | H | H |
| Y.109 | CH₃ | CH₃ | F | H | 4-p-Cl-phenyl | H | H |
| Y.110 | F | CH₃ | F | H | 4-p-Cl-phenyl | H | H |
| Y.111 | H | H | F | F | 4-p-Cl-phenyl | H | H |
| Y.112 | CH₃ | H | F | F | 4-p-Cl-phenyl | H | H |
| Y.113 | F | H | F | F | 4-p-Cl-phenyl | H | H |
| Y.114 | H | CH₃ | F | F | 4-p-Cl-phenyl | H | H |

TABLE Y-continued

| Cpd No. | R₁ | R₂ | R₃ | R₄ | R₉ₐ | R₉ᵦ | R₉c |
|---|---|---|---|---|---|---|---|
| Y.115 | CH₃ | CH₃ | F | F | 4-p-Cl-phenyl | H | H |
| Y.116 | F | CH₃ | F | F | 4-p-Cl-phenyl | H | H |
| Y.117 | H | H | H | H | 4-C≡CC(CH₃)₃ | H | H |
| Y.118 | CH₃ | H | H | H | 4-C≡CC(CH₃)₃ | H | H |
| Y.119 | CH₂CH₃ | H | H | H | 4-C≡CC(CH₃)₃ | H | H |
| Y.120 | F | H | H | H | 4-C≡CC(CH₃)₃ | H | H |
| Y.121 | CN | H | H | H | 4-C≡CC(CH₃)₃ | H | H |
| Y.122 | H | CH₃ | H | H | 4-C≡CC(CH₃)₃ | H | H |
| Y.123 | CH₃ | CH₃ | H | H | 4-C≡CC(CH₃)₃ | H | H |
| Y.124 | CH₂CH₃ | CH₃ | H | H | 4-C≡CC(CH₃)₃ | H | H |
| Y.125 | F | CH₃ | H | H | 4-C≡CC(CH₃)₃ | H | H |
| Y.126 | CN | CH₃ | H | H | 4-C≡CC(CH₃)₃ | H | H |
| Y.127 | H | CH₂CH₃ | H | H | 4-C≡CC(CH₃)₃ | H | H |
| Y.128 | CH₃ | CH₂CH₃ | H | H | 4-C≡CC(CH₃)₃ | H | H |
| Y.129 | F | CH₂CH₃ | H | H | 4-C≡CC(CH₃)₃ | H | H |
| Y.130 | CN | CH₂CH₃ | H | H | 4-C≡CC(CH₃)₃ | H | H |
| Y.131 | H | H | F | H | 4-C≡CC(CH₃)₃ | H | H |
| Y.132 | H | CH₃ | F | H | 4-C≡CC(CH₃)₃ | H | H |
| Y.133 | CH₃ | CH₃ | F | H | 4-C≡CC(CH₃)₃ | H | H |
| Y.134 | F | CH₃ | F | H | 4-C≡CC(CH₃)₃ | H | H |
| Y.135 | H | H | F | F | 4-C≡CC(CH₃)₃ | H | H |
| Y.136 | CH₃ | H | F | F | 4-C≡CC(CH₃)₃ | H | H |
| Y.137 | F | H | F | F | 4-C≡CC(CH₃)₃ | H | H |
| Y.138 | H | CH₃ | F | F | 4-C≡CC(CH₃)₃ | H | H |
| Y.139 | CH₃ | CH₃ | F | F | 4-C≡CC(CH₃)₃ | H | H |
| Y.140 | F | CH₃ | F | F | 4-C≡CC(CH₃)₃ | H | H |
| Y.141 | H | H | H | H | 4-C≡CC(CH₃)₃ | H | H |
| Y.142 | CH₃ | H | H | H | 4-C≡CC(CH₃)₃ | H | H |
| Y.143 | H | H | H | H | 4-Cl | 2-Cl | H |
| Y.144 | CH₃ | H | H | H | 4-Cl | 2-Cl | H |
| Y.145 | CH₂CH₃ | H | H | H | 4-Cl | 2-Cl | H |
| Y.146 | F | H | H | H | 4-Cl | 2-Cl | H |
| Y.147 | CN | H | H | H | 4-Cl | 2-Cl | H |
| Y.148 | H | CH₃ | H | H | 4-Cl | 2-Cl | H |
| Y.149 | CH₃ | CH₃ | H | H | 4-Cl | 2-Cl | H |
| Y.150 | CH₂CH₃ | CH₃ | H | H | 4-Cl | 2-Cl | H |
| Y.151 | F | CH₃ | H | H | 4-Cl | 2-Cl | H |
| Y.152 | CN | CH₃ | H | H | 4-Cl | 2-Cl | H |
| Y.153 | H | CH₂CH₃ | H | H | 4-Cl | 2-Cl | H |
| Y.154 | CH₃ | CH₂CH₃ | H | H | 4-Cl | 2-Cl | H |
| Y.155 | F | CH₂CH₃ | H | H | 4-Cl | 2-Cl | H |
| Y.156 | CN | CH₂CH₃ | H | H | 4-Cl | 2-Cl | H |
| Y.157 | H | H | F | H | 4-Cl | 2-Cl | H |
| Y.158 | CH₃ | H | F | H | 4-Cl | 2-Cl | H |
| Y.159 | F | H | F | H | 4-Cl | 2-Cl | H |
| Y.160 | H | CH₃ | F | H | 4-Cl | 2-Cl | H |
| Y.161 | CH₃ | CH₃ | F | H | 4-Cl | 2-Cl | H |
| Y.162 | F | CH₃ | F | H | 4-Cl | 2-Cl | H |
| Y.163 | H | H | F | F | 4-Cl | 2-Cl | H |
| Y.164 | CH₃ | H | F | F | 4-Cl | 2-Cl | H |
| Y.165 | F | H | F | F | 4-Cl | 2-Cl | H |
| Y.166 | H | CH₃ | F | F | 4-Cl | 2-Cl | H |
| Y.167 | CH₃ | CH₃ | F | F | 4-Cl | 2-Cl | H |
| Y.168 | F | CH₃ | F | F | 4-Cl | 2-Cl | H |
| Y.169 | H | H | H | H | 4-F | 2-F | H |
| Y.170 | CH₃ | H | H | H | 4-F | 2-F | H |
| Y.171 | CH₂CH₃ | H | H | H | 4-F | 2-F | H |
| Y.172 | F | H | H | H | 4-F | 2-F | H |
| Y.173 | CN | H | H | H | 4-F | 2-F | H |
| Y.174 | H | CH₃ | H | H | 4-F | 2-F | H |
| Y.175 | CH₃ | CH₃ | H | H | 4-F | 2-F | H |
| Y.176 | CH₂CH₃ | CH₃ | H | H | 4-F | 2-F | H |
| Y.177 | F | CH₃ | H | H | 4-F | 2-F | H |
| Y.178 | CN | CH₃ | H | H | 4-F | 2-F | H |
| Y.179 | H | CH₂CH₃ | H | H | 4-F | 2-F | H |
| Y.180 | CH₃ | CH₂CH₃ | H | H | 4-F | 2-F | H |
| Y.181 | F | CH₂CH₃ | H | H | 4-F | 2-F | H |
| Y.182 | CN | CH₂CH₃ | H | H | 4-F | 2-F | H |
| Y.183 | H | H | F | H | 4-F | 2-F | H |
| Y.184 | CH₃ | H | F | H | 4-F | 2-F | H |
| Y.185 | F | H | F | H | 4-F | 2-F | H |
| Y.186 | H | CH₃ | F | H | 4-F | 2-F | H |
| Y.187 | CH₃ | CH₃ | F | H | 4-F | 2-F | H |
| Y.188 | F | CH₃ | F | H | 4-F | 2-F | H |
| Y.189 | H | H | F | F | 4-F | 2-F | H |
| Y.190 | CH₃ | H | F | F | 4-F | 2-F | H |
| Y.191 | F | H | F | F | 4-F | 2-F | H |
| Y.192 | H | CH₃ | F | F | 4-F | 2-F | H |

TABLE Y-continued

| Cpd No. | R$_1$ | R$_2$ | R$_3$ | R$_4$ | R$_{9a}$ | R$_{9b}$ | R$_{9c}$ |
|---|---|---|---|---|---|---|---|
| Y.193 | CH$_3$ | CH$_3$ | F | F | 4-F | 2-F | H |
| Y.194 | F | CH$_3$ | F | F | 4-F | 2-F | H |
| Y.195 | H | H | H | H | 4-Cl | 2-F | H |
| Y.196 | CH$_3$ | H | H | H | 4-Cl | 2-F | H |
| Y.197 | CH$_2$CH$_3$ | H | H | H | 4-Cl | 2-F | H |
| Y.198 | F | H | H | H | 4-Cl | 2-F | H |
| Y.199 | CN | H | H | H | 4-Cl | 2-F | H |
| Y.200 | H | CH$_3$ | H | H | 4-Cl | 2-F | H |
| Y.201 | CH$_3$ | CH$_3$ | H | H | 4-Cl | 2-F | H |
| Y.202 | CH$_2$CH$_3$ | CH$_3$ | H | H | 4-Cl | 2-F | H |
| Y.203 | F | CH$_3$ | H | H | 4-Cl | 2-F | H |
| Y.204 | CN | CH$_3$ | H | H | 4-Cl | 2-F | H |
| Y.205 | H | CH$_2$CH$_3$ | H | H | 4-Cl | 2-F | H |
| Y.206 | CH$_3$ | CH$_2$CH$_3$ | H | H | 4-Cl | 2-F | H |
| Y.207 | F | CH$_2$CH$_3$ | H | H | 4-Cl | 2-F | H |
| Y.208 | CN | CH$_2$CH$_3$ | H | H | 4-Cl | 2-F | H |
| Y.209 | H | H | F | H | 4-Cl | 2-F | H |
| Y.210 | CH$_3$ | H | F | H | 4-Cl | 2-F | H |
| Y.211 | F | H | F | H | 4-Cl | 2-F | H |
| Y.212 | H | CH$_3$ | F | H | 4-Cl | 2-F | H |
| Y.213 | CH$_3$ | CH$_3$ | F | H | 4-Cl | 2-F | H |
| Y.214 | F | CH$_3$ | F | H | 4-Cl | 2-F | H |
| Y.215 | H | H | F | F | 4-Cl | 2-F | H |
| Y.216 | CH$_3$ | H | F | F | 4-Cl | 2-F | H |
| Y.217 | F | H | F | F | 4-Cl | 2-F | H |
| Y.218 | H | CH$_3$ | F | F | 4-Cl | 2-F | H |
| Y.219 | CH$_3$ | CH$_3$ | F | F | 4-Cl | 2-F | H |
| Y.220 | F | CH$_3$ | F | F | 4-Cl | 2-F | H |
| Y.221 | H | H | H | H | 4-F | 2-Cl | H |
| Y.222 | H | H | H | H | 2-Cl | H | H |
| Y.223 | CH$_2$CH$_3$ | H | H | H | 4-F | 2-Cl | H |
| Y.224 | F | H | H | H | 4-F | 2-Cl | H |
| Y.225 | CN | H | H | H | 4-F | 2-Cl | H |
| Y.226 | H | CH$_3$ | H | H | 4-F | 2-Cl | H |
| Y.227 | CH$_3$ | CH$_3$ | H | H | 4-F | 2-Cl | H |
| Y.228 | CH$_2$CH$_3$ | CH$_3$ | H | H | 4-F | 2-Cl | H |
| Y.229 | F | CH$_3$ | H | H | 4-F | 2-Cl | H |
| Y.230 | CN | CH$_3$ | H | H | 4-F | 2-Cl | H |
| Y.231 | H | CH$_2$CH$_3$ | H | H | 4-F | 2-Cl | H |
| Y.232 | CH$_3$ | CH$_2$CH$_3$ | H | H | 4-F | 2-Cl | H |
| Y.233 | F | CH$_2$CH$_3$ | H | H | 4-F | 2-Cl | H |
| Y.234 | CN | CH$_2$CH$_3$ | H | H | 4-F | 2-Cl | H |
| Y.235 | H | H | F | H | 4-F | 2-Cl | H |
| Y.236 | CH$_3$ | H | F | H | 4-F | 2-Cl | H |
| Y.237 | F | H | F | H | 4-F | 2-Cl | H |
| Y.238 | H | CH$_3$ | F | H | 4-F | 2-Cl | H |
| Y.239 | CH$_3$ | CH$_3$ | F | H | 4-F | 2-Cl | H |
| Y.240 | F | CH$_3$ | F | H | 4-F | 2-Cl | H |
| Y.241 | H | H | F | F | 4-F | 2-Cl | H |
| Y.242 | CH$_3$ | H | F | F | 4-F | 2-Cl | H |
| Y.243 | F | H | F | F | 4-F | 2-Cl | H |
| Y.244 | H | CH$_3$ | F | F | 4-F | 2-Cl | H |
| Y.245 | CH$_3$ | CH$_3$ | F | F | 4-F | 2-Cl | H |
| Y.246 | F | CH$_3$ | F | F | 4-F | 2-Cl | H |
| Y.247 | H | H | H | H | 4-p-Cl-phenyl | 2-Cl | H |
| Y.248 | F | H | H | H | 4-p-Cl-phenyl | 2-Cl | H |
| Y.249 | H | CH$_3$ | H | H | 4-p-Cl-phenyl | 2-Cl | H |
| Y.250 | F | CH$_3$ | H | H | 4-p-Cl-phenyl | 2-Cl | H |
| Y.251 | H | H | F | H | 4-p-Cl-phenyl | 2-Cl | H |
| Y.252 | F | H | F | H | 4-p-Cl-phenyl | 2-Cl | H |
| Y.253 | H | CH$_3$ | F | H | 4-p-Cl-phenyl | 2-Cl | H |
| Y.254 | F | CH$_3$ | F | H | 4-p-Cl-phenyl | 2-Cl | H |
| Y.255 | H | H | F | F | 4-p-Cl-phenyl | 2-Cl | H |
| Y.256 | H | CH$_3$ | F | F | 4-p-Cl-phenyl | 2-Cl | H |
| Y.257 | H | H | H | H | 4-Br | 2-Cl | H |
| Y.258 | H | H | H | H | 4-Br | 2-Cl | 6-Cl |
| Y.259 | H | H | H | H | 4-Cl | 2-Cl | 6-Cl |
| Y.260 | H | H | H | H | 4-p-CF$_3$-phenyl | 2-Cl | 6-Cl |
| Y.261 | H | H | H | H | 4-p-CF$_3$-phenyl | 2-Cl | H |
| Y.262 | H | H | H | H | 4-(3',4'-Cl$_2$)-phenyl | 2-Cl | H |
| Y.263 | H | H | H | H | 4-(3',4'-Cl$_2$)-phenyl | 2-Cl | 6-Cl |
| Y.264 | H | H | H | H | 4-p-Cl-phenyl | 2-Cl | 6-Cl |
| Y.265 | H | H | H | H | 4-(CH$_3$) | 2-Cl | H |
| Y.266 | H | H | H | H | 4-(CH$_3$) | 2-CH$_3$ | 6-(CH$_3$) |
| Y.267 | H | H | H | H | 4-C≡CC(CH$_3$)$_3$ | 2-Cl | H |
| Y.268 | H | H | H | H | 4-C≡CC(CH$_3$)$_3$ | 2-Cl | 6-Cl |
| Y.269 | H | H | H | H | 4-C≡CCH(CH$_2$)$_2$ | 2-Cl | H |
| Y.270 | H | H | H | H | 4-C≡CCH(CH$_2$)$_2$ | 2-Cl | 6-Cl |

TABLE Y-continued

| Cpd No. | $R_1$ | $R_2$ | $R_3$ | $R_4$ | $R_{9a}$ | $R_{9b}$ | $R_{9c}$ |
|---|---|---|---|---|---|---|---|
| Y.271 | H | H | H | H | 4-CH=N—OCH$_3$ | 2-Cl | H |
| Y.272 | H | H | H | H | 4-CH=N—OCH$_3$ | 2-Cl | 6-Cl |
| Y.273 | H | H | H | H | 4-C(CH$_3$)=N—OCH$_3$ | 2-Cl | H |
| Y.274 | H | H | H | H | 4-C(CH$_3$)=N—OCH$_3$ | 2-Cl | 6-Cl |

Table 1 provides 274 compounds of formula (IA), wherein A is

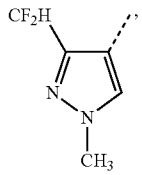

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y. For example, compound 1.001 has the following structure:

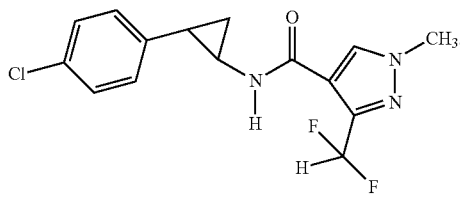

(1.001)

Table 2 provides 274 compounds of formula (IA) wherein A is

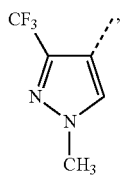

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 3 provides 274 compounds of formula (IA) wherein A is

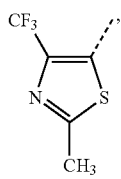

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 4 provides 274 compounds of formula (IA) wherein A is

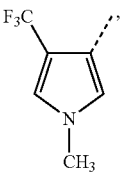

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 5 provides 274 compounds of formula (IA) wherein A is

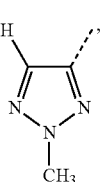

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 6 provides 274 compounds of formula (IA) wherein A is

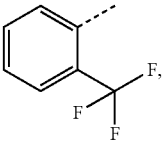

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 7 provides 274 compounds of formula (IA) wherein A is

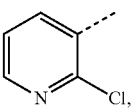

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Table 8 provides 274 compounds of formula (IA) wherein A is

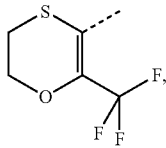

wherein the broken lines indicate the point of attachment of the group A to the amide group, and $R_1$, $R_2$, $R_3$, $R_4$, $R_{9a}$, $R_{9b}$ and $R_{9c}$ are as defined in Table Y.

Tables 9 to 16: Compounds of Formula IB

The invention is further illustrated by the preferred individual compounds of formula (IB) listed below in Tables 9 to 16. Characterising data is given in Table 18.

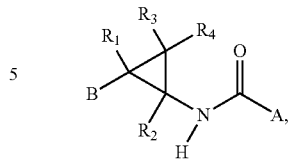
(IB)

Each of Tables 9 to 16, which follow the Table W below, comprises 872 compounds of the formula (IB) in which B, $R_1$, $R_2$, $R_3$ and $R_4$ have the values given in Table W and A has the value given in the relevant Table 9 to 16. Thus Table 9 corresponds to Table W when W is 9 and A has the value given under the Table 9 heading, Table 10 corresponds to Table W when W is 10 and A has the value given under the Table 10 heading, and so on for Tables 11 to 16.

In Table W the group B stands for the group $B_1$, $B_2$, $B_3$ or $B_4$:

TABLE W

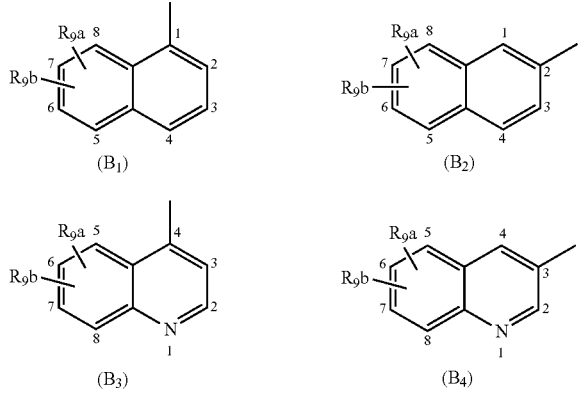

| Compound No. | B | $R_1$ | $R_2$ | $R_3$ | $R_4$ | $R_{9a}$ | $R_{9b}$ |
|---|---|---|---|---|---|---|---|
| W.001 | $B_1$ | H | H | H | H | 2-Cl | H |
| W.002 | $B_1$ | $CH_3$ | H | H | H | 2-Cl | H |
| W.003 | $B_1$ | $CH_2CH_3$ | H | H | H | 2-Cl | H |
| W.004 | $B_1$ | F | H | H | H | 2-Cl | H |
| W.005 | $B_1$ | CN | H | H | H | 2-Cl | H |
| W.006 | $B_1$ | H | $CH_3$ | H | H | 2-Cl | H |
| W.007 | $B_1$ | $CH_3$ | $CH_3$ | H | H | 2-Cl | H |
| W.008 | $B_1$ | $CH_2CH_3$ | $CH_3$ | H | H | 2-Cl | H |
| W.009 | $B_1$ | F | $CH_3$ | H | H | 2-Cl | H |
| W.010 | $B_1$ | CN | $CH_3$ | H | H | 2-Cl | H |
| W.011 | $B_1$ | H | $CH_2CH_3$ | H | H | 2-Cl | H |
| W.012 | $B_1$ | $CH_3$ | $CH_2CH_3$ | H | H | 2-Cl | H |
| W.013 | $B_1$ | F | $CH_2CH_3$ | H | H | 2-Cl | H |
| W.014 | $B_1$ | CN | $CH_2CH_3$ | H | H | 2-Cl | H |
| W.015 | $B_1$ | H | H | F | H | 2-Cl | H |
| W.016 | $B_1$ | $CH_3$ | H | F | H | 2-Cl | H |
| W.017 | $B_1$ | F | H | F | H | 2-Cl | H |
| W.018 | $B_1$ | H | $CH_3$ | F | H | 2-Cl | H |
| W.019 | $B_1$ | $CH_3$ | $CH_3$ | F | H | 2-Cl | H |
| W.020 | $B_1$ | F | $CH_3$ | F | H | 2-Cl | H |
| W.021 | $B_1$ | H | H | F | F | 2-Cl | H |
| W.022 | $B_1$ | H | H | $CH_3$ | $CH_3$ | 2-Cl | H |
| W.023 | $B_1$ | F | H | $CH_3$ | $CH_3$ | 2-Cl | H |
| W.024 | $B_1$ | H | $CH_3$ | $CH_3$ | $CH_3$ | 2-Cl | H |
| W.025 | $B_1$ | $CH_3$ | $CH_3$ | $CH_3$ | $CH_3$ | 2-Cl | H |
| W.026 | $B_1$ | F | $CH_3$ | $CH_3$ | $CH_3$ | 2-Cl | H |
| W.027 | $B_1$ | H | H | H | H | 4-Cl | H |
| W.028 | $B_1$ | $CH_3$ | H | H | H | 4-Cl | H |
| W.029 | $B_1$ | $CH_2CH_3$ | H | H | H | 4-Cl | H |
| W.030 | $B_1$ | F | H | H | H | 4-Cl | H |
| W.031 | $B_1$ | CN | H | H | H | 4-Cl | H |
| W.032 | $B_1$ | H | $CH_3$ | H | H | 4-Cl | H |

TABLE W-continued

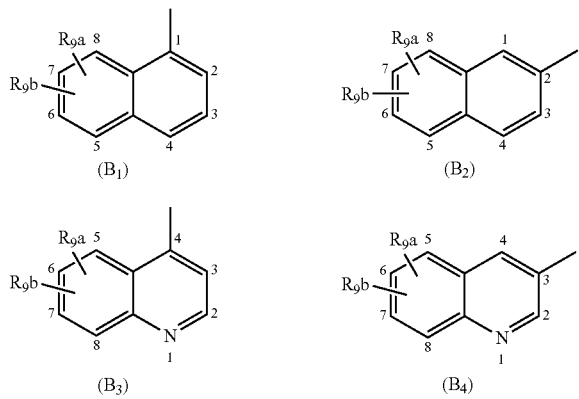

(B₁)  (B₂)

(B₃)  (B₄)

| Compound No. | B | R₁ | R₂ | R₃ | R₄ | R₉ₐ | R₉ᵦ |
|---|---|---|---|---|---|---|---|
| W.033 | B₁ | CH₃ | CH₃ | H | H | 4-Cl | H |
| W.034 | B₁ | CH₂CH₃ | CH₃ | H | H | 4-Cl | H |
| W.035 | B₁ | F | CH₃ | H | H | 4-Cl | H |
| W.036 | B₁ | CN | CH₃ | H | H | 4-Cl | H |
| W.037 | B₁ | H | CH₂CH₃ | H | H | 4-Cl | H |
| W.038 | B₁ | CH₃ | CH₂CH₃ | H | H | 4-Cl | H |
| W.039 | B₁ | F | CH₂CH₃ | H | H | 4-Cl | H |
| W.040 | B₁ | CN | CH₂CH₃ | H | H | 4-Cl | H |
| W.041 | B₁ | H | H | F | H | 4-Cl | H |
| W.042 | B₁ | CH₃ | H | F | H | 4-Cl | H |
| W.043 | B₁ | F | H | F | H | 4-Cl | H |
| W.044 | B₁ | H | CH₃ | F | H | 4-Cl | H |
| W.045 | B₁ | CH₃ | CH₃ | F | H | 4-Cl | H |
| W.046 | B₁ | F | CH₃ | F | H | 4-Cl | H |
| W.047 | B₁ | H | H | F | F | 4-Cl | H |
| W.048 | B₁ | H | H | CH₃ | CH₃ | 4-Cl | H |
| W.049 | B₁ | F | H | CH₃ | CH₃ | 4-Cl | H |
| W.050 | B₁ | H | CH₃ | CH₃ | CH₃ | 4-Cl | H |
| W.051 | B₁ | CH₃ | CH₃ | CH₃ | CH₃ | 4-Cl | H |
| W.052 | B₁ | F | CH₃ | CH₃ | CH₃ | 4-Cl | H |
| W.053 | B₁ | H | H | H | H | 5-Cl | H |
| W.054 | B₁ | CH₃ | H | H | H | 5-Cl | H |
| W.055 | B₁ | CH₂CH₃ | H | H | H | 5-Cl | H |
| W.056 | B₁ | F | H | H | H | 5-Cl | H |
| W.057 | B₁ | CN | H | H | H | 5-Cl | H |
| W.058 | B₁ | H | CH₃ | H | H | 5-Cl | H |
| W.059 | B₁ | CH₃ | CH₃ | H | H | 5-Cl | H |
| W.060 | B₁ | CH₂CH₃ | CH₃ | H | H | 5-Cl | H |
| W.061 | B₁ | F | CH₃ | H | H | 5-Cl | H |
| W.062 | B₁ | CN | CH₃ | H | H | 5-Cl | H |
| W.063 | B₁ | H | CH₂CH₃ | H | H | 5-Cl | H |
| W.064 | B₁ | CH₃ | CH₂CH₃ | H | H | 5-Cl | H |
| W.065 | B₁ | F | CH₂CH₃ | H | H | 5-Cl | H |
| W.066 | B₁ | CN | CH₂CH₃ | H | H | 5-Cl | H |
| W.067 | B₁ | H | H | F | H | 5-Cl | H |
| W.068 | B₁ | CH₃ | H | F | H | 5-Cl | H |
| W.069 | B₁ | F | H | F | H | 5-Cl | H |
| W.070 | B₁ | H | CH₃ | F | H | 5-Cl | H |
| W.071 | B₁ | CH₃ | CH₃ | F | H | 5-Cl | H |
| W.072 | B₁ | F | CH₃ | F | H | 5-Cl | H |
| W.073 | B₁ | H | H | F | F | 5-Cl | H |
| W.074 | B₁ | H | H | CH₃ | CH₃ | 5-Cl | H |
| W.075 | B₁ | F | H | CH₃ | CH₃ | 5-Cl | H |
| W.076 | B₁ | H | CH₃ | CH₃ | CH₃ | 5-Cl | H |
| W.077 | B₁ | CH₃ | CH₃ | CH₃ | CH₃ | 5-Cl | H |
| W.078 | B₁ | F | CH₃ | CH₃ | CH₃ | 5-Cl | H |
| W.079 | B₁ | H | H | H | H | 6-Cl | H |
| W.080 | B₁ | CH₃ | H | H | H | 6-Cl | H |
| W.081 | B₁ | CH₂CH₃ | H | H | H | 6-Cl | H |
| W.082 | B₁ | F | H | H | H | 6-Cl | H |
| W.083 | B₁ | CN | H | H | H | 6-Cl | H |
| W.084 | B₁ | H | CH₃ | H | H | 6-Cl | H |
| W.085 | B₁ | CH₃ | CH₃ | H | H | 6-Cl | H |
| W.086 | B₁ | CH₂CH₃ | CH₃ | H | H | 6-Cl | H |
| W.087 | B₁ | F | CH₃ | H | H | 6-Cl | H |
| W.088 | B₁ | CN | CH₃ | H | H | 6-Cl | H |
| W.089 | B₁ | H | CH₂CH₃ | H | H | 6-Cl | H |

TABLE W-continued

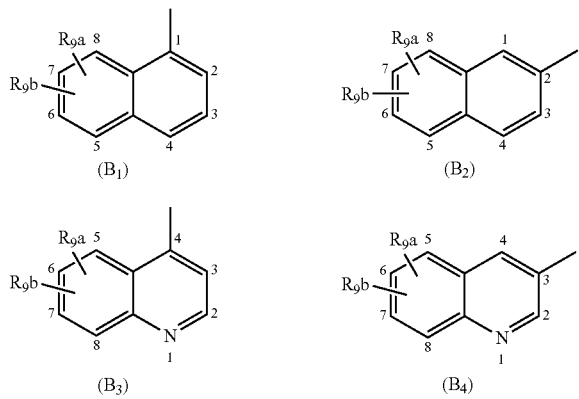

| Compound No. | B | R₁ | R₂ | R₃ | R₄ | R₉ₐ | R₉ᵦ |
|---|---|---|---|---|---|---|---|
| W.090 | B₁ | CH₃ | CH₂CH₃ | H | H | 6-Cl | H |
| W.091 | B₁ | F | CH₂CH₃ | H | H | 6-Cl | H |
| W.092 | B₁ | CN | CH₂CH₃ | H | H | 6-Cl | H |
| W.093 | B₁ | H | H | F | H | 6-Cl | H |
| W.094 | B₁ | CH₃ | H | F | H | 6-Cl | H |
| W.095 | B₁ | F | H | F | H | 6-Cl | H |
| W.096 | B₁ | H | CH₃ | F | H | 6-Cl | H |
| W.097 | B₁ | CH₃ | CH₃ | F | H | 6-Cl | H |
| W.098 | B₁ | F | CH₃ | F | H | 6-Cl | H |
| W.099 | B₁ | H | H | F | F | 6-Cl | H |
| W.100 | B₁ | H | H | CH₃ | CH₃ | 6-Cl | H |
| W.101 | B₁ | F | H | CH₃ | CH₃ | 6-Cl | H |
| W.102 | B₁ | H | CH₃ | CH₃ | CH₃ | 6-Cl | H |
| W.103 | B₁ | CH₃ | CH₃ | CH₃ | CH₃ | 6-Cl | H |
| W.104 | B₁ | F | CH₃ | CH₃ | CH₃ | 6-Cl | H |
| W.105 | B₁ | H | H | H | H | 8-Cl | H |
| W.106 | B₁ | CH₃ | H | H | H | 8-Cl | H |
| W.107 | B₁ | CH₂CH₃ | H | H | H | 8-Cl | H |
| W.108 | B₁ | F | H | H | H | 8-Cl | H |
| W.109 | B₁ | CN | H | H | H | 8-Cl | H |
| W.110 | B₁ | H | CH₃ | H | H | 8-Cl | H |
| W.111 | B₁ | CH₃ | CH₃ | H | H | 8-Cl | H |
| W.112 | B₁ | CH₂CH₃ | CH₃ | H | H | 8-Cl | H |
| W.113 | B₁ | F | CH₃ | H | H | 8-Cl | H |
| W.114 | B₁ | CN | CH₃ | H | H | 8-Cl | H |
| W.115 | B₁ | H | CH₂CH₃ | H | H | 8-Cl | H |
| W.116 | B₁ | CH₃ | CH₂CH₃ | H | H | 8-Cl | H |
| W.117 | B₁ | F | CH₂CH₃ | H | H | 8-Cl | H |
| W.118 | B₁ | CN | CH₂CH₃ | H | H | 8-Cl | H |
| W.119 | B₁ | H | H | F | H | 8-Cl | H |
| W.120 | B₁ | CH₃ | H | F | H | 8-Cl | H |
| W.121 | B₁ | F | H | F | H | 8-Cl | H |
| W.122 | B₁ | H | CH₃ | F | H | 8-Cl | H |
| W.123 | B₁ | CH₃ | CH₃ | F | H | 8-Cl | H |
| W.124 | B₁ | F | CH₃ | F | H | 8-Cl | H |
| W.125 | B₁ | H | H | F | F | 8-Cl | H |
| W.126 | B₁ | H | H | CH₃ | CH₃ | 8-Cl | H |
| W.127 | B₁ | F | H | CH₃ | CH₃ | 8-Cl | H |
| W.128 | B₁ | H | CH₃ | CH₃ | CH₃ | 8-Cl | H |
| W.129 | B₁ | CH₃ | CH₃ | CH₃ | CH₃ | 8-Cl | H |
| W.130 | B₁ | F | CH₃ | CH₃ | CH₃ | 8-Cl | H |
| W.131 | B₁ | H | H | H | H | 2-p-Cl-phenyl | H |
| W.132 | B₁ | CH₃ | H | H | H | 2-p-Cl-phenyl | H |
| W.133 | B₁ | CH₂CH₃ | H | H | H | 2-p-Cl-phenyl | H |
| W.134 | B₁ | F | H | H | H | 2-p-Cl-phenyl | H |
| W.135 | B₁ | CN | H | H | H | 2-p-Cl-phenyl | H |
| W.136 | B₁ | H | CH₃ | H | H | 2-p-Cl-phenyl | H |
| W.137 | B₁ | CH₃ | CH₃ | H | H | 2-p-Cl-phenyl | H |
| W.138 | B₁ | CH₂CH₃ | CH₃ | H | H | 2-p-Cl-phenyl | H |
| W.139 | B₁ | F | CH₃ | H | H | 2-p-Cl-phenyl | H |
| W.140 | B₁ | CN | CH₃ | H | H | 2-p-Cl-phenyl | H |
| W.141 | B₁ | H | CH₂CH₃ | H | H | 2-p-Cl-phenyl | H |
| W.142 | B₁ | CH₃ | CH₂CH₃ | H | H | 2-p-Cl-phenyl | H |
| W.143 | B₁ | F | CH₂CH₃ | H | H | 2-p-Cl-phenyl | H |
| W.144 | B₁ | CN | CH₂CH₃ | H | H | 2-p-Cl-phenyl | H |
| W.145 | B₁ | H | H | F | H | 2-p-Cl-phenyl | H |
| W.146 | B₁ | CH₃ | H | F | H | 2-p-Cl-phenyl | H |

TABLE W-continued

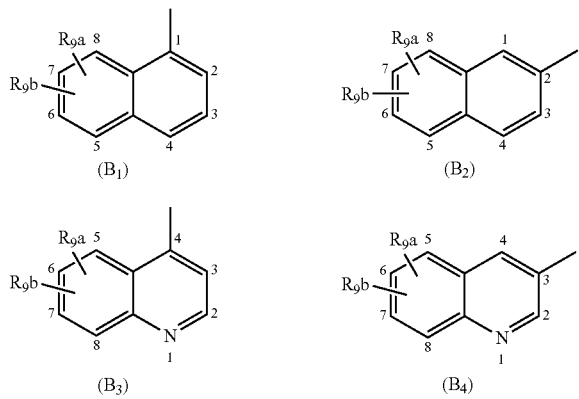

| Compound No. | B | R₁ | R₂ | R₃ | R₄ | R₉ₐ | R₉ᵦ |
|---|---|---|---|---|---|---|---|
| W.147 | B₁ | F | H | F | H | 2-p-Cl-phenyl | H |
| W.148 | B₁ | H | CH₃ | F | H | 2-p-Cl-phenyl | H |
| W.149 | B₁ | CH₃ | CH₃ | F | H | 2-p-Cl-phenyl | H |
| W.150 | B₁ | F | CH₃ | F | H | 2-p-Cl-phenyl | H |
| W.151 | B₁ | H | H | F | F | 2-p-Cl-phenyl | H |
| W.152 | B₁ | H | H | CH₃ | CH₃ | 2-p-Cl-phenyl | H |
| W.153 | B₁ | F | H | CH₃ | CH₃ | 2-p-Cl-phenyl | H |
| W.154 | B₁ | H | CH₃ | CH₃ | CH₃ | 2-p-Cl-phenyl | H |
| W.155 | B₁ | CH₃ | CH₃ | CH₃ | CH₃ | 2-p-Cl-phenyl | H |
| W.156 | B₁ | F | CH₃ | CH₃ | CH₃ | 2-p-Cl-phenyl | H |
| W.157 | B₁ | H | H | H | H | 4-p-Cl-phenyl | H |
| W.158 | B₁ | CH₃ | H | H | H | 4-p-Cl-phenyl | H |
| W.159 | B₁ | CH₂CH₃ | H | H | H | 4-p-Cl-phenyl | H |
| W.160 | B₁ | F | H | H | H | 4-p-Cl-phenyl | H |
| W.161 | B₁ | CN | H | H | H | 4-p-Cl-phenyl | H |
| W.162 | B₁ | H | CH₃ | H | H | 4-p-Cl-phenyl | H |
| W.163 | B₁ | CH₃ | CH₃ | H | H | 4-p-Cl-phenyl | H |
| W.164 | B₁ | CH₂CH₃ | CH₃ | H | H | 4-p-Cl-phenyl | H |
| W.165 | B₁ | F | CH₃ | H | H | 4-p-Cl-phenyl | H |
| W.166 | B₁ | CN | CH₃ | H | H | 4-p-Cl-phenyl | H |
| W.167 | B₁ | H | CH₂CH₃ | H | H | 4-p-Cl-phenyl | H |
| W.168 | B₁ | CH₃ | CH₂CH₃ | H | H | 4-p-Cl-phenyl | H |
| W.169 | B₁ | F | CH₂CH₃ | H | H | 4-p-Cl-phenyl | H |
| W.170 | B₁ | CN | CH₂CH₃ | H | H | 4-p-Cl-phenyl | H |
| W.171 | B₁ | H | H | F | H | 4-p-Cl-phenyl | H |
| W.172 | B₁ | CH₃ | H | F | H | 4-p-Cl-phenyl | H |
| W.173 | B₁ | F | H | F | H | 4-p-Cl-phenyl | H |
| W.174 | B₁ | H | CH₃ | F | H | 4-p-Cl-phenyl | H |
| W.175 | B₁ | CH₃ | CH₃ | F | H | 4-p-Cl-phenyl | H |
| W.176 | B₁ | F | CH₃ | F | H | 4-p-Cl-phenyl | H |
| W.177 | B₁ | H | H | F | F | 4-p-Cl-phenyl | H |
| W.178 | B₁ | H | H | CH₃ | CH₃ | 4-p-Cl-phenyl | H |
| W.179 | B₁ | F | H | CH₃ | CH₃ | 4-p-Cl-phenyl | H |
| W.180 | B₁ | H | CH₃ | CH₃ | CH₃ | 4-p-Cl-phenyl | H |
| W.181 | B₁ | CH₃ | CH₃ | CH₃ | CH₃ | 4-p-Cl-phenyl | H |
| W.182 | B₁ | F | CH₃ | CH₃ | CH₃ | 4-p-Cl-phenyl | H |
| W.183 | B₁ | H | H | H | H | 8-p-Cl-phenyl | H |
| W.184 | B₁ | CH₃ | H | H | H | 8-p-Cl-phenyl | H |
| W.185 | B₁ | CH₂CH₃ | H | H | H | 8-p-Cl-phenyl | H |
| W.186 | B₁ | F | H | H | H | 8-p-Cl-phenyl | H |
| W.187 | B₁ | CN | H | H | H | 8-p-Cl-phenyl | H |
| W.188 | B₁ | H | CH₃ | H | H | 8-p-Cl-phenyl | H |
| W.189 | B₁ | CH₃ | CH₃ | H | H | 8-p-Cl-phenyl | H |
| W.190 | B₁ | CH₂CH₃ | CH₃ | H | H | 8-p-Cl-phenyl | H |
| W.191 | B₁ | F | CH₃ | H | H | 8-p-Cl-phenyl | H |
| W.192 | B₁ | CN | CH₃ | H | H | 8-p-Cl-phenyl | H |
| W.193 | B₁ | H | CH₂CH₃ | H | H | 8-p-Cl-phenyl | H |
| W.194 | B₁ | CH₃ | CH₂CH₃ | H | H | 8-p-Cl-phenyl | H |
| W.195 | B₁ | F | CH₂CH₃ | H | H | 8-p-Cl-phenyl | H |
| W.196 | B₁ | CN | CH₂CH₃ | H | H | 8-p-Cl-phenyl | H |
| W.197 | B₁ | H | H | F | H | 8-p-Cl-phenyl | H |
| W.198 | B₁ | CH₃ | H | F | H | 8-p-Cl-phenyl | H |
| W.199 | B₁ | F | H | F | H | 8-p-Cl-phenyl | H |
| W.200 | B₁ | H | CH₃ | F | H | 8-p-Cl-phenyl | H |
| W.201 | B₁ | CH₃ | CH₃ | F | H | 8-p-Cl-phenyl | H |
| W.202 | B₁ | F | CH₃ | F | H | 8-p-Cl-phenyl | H |
| W.203 | B₁ | H | H | F | F | 8-p-Cl-phenyl | H |

TABLE W-continued

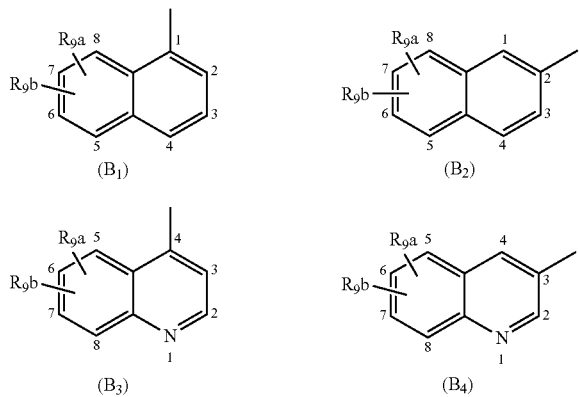

| Compound No. | B | R₁ | R₂ | R₃ | R₄ | R₉ₐ | R₉ᵦ |
|---|---|---|---|---|---|---|---|
| W.204 | B₁ | H | H | CH₃ | CH₃ | 8-p-Cl-phenyl | H |
| W.205 | B₁ | F | H | CH₃ | CH₃ | 8-p-Cl-phenyl | H |
| W.206 | B₁ | H | CH₃ | CH₃ | CH₃ | 8-p-Cl-phenyl | H |
| W.207 | B₁ | CH₃ | CH₃ | CH₃ | CH₃ | 8-p-Cl-phenyl | H |
| W.208 | B₁ | F | CH₃ | CH₃ | CH₃ | 8-p-Cl-phenyl | H |
| W.209 | B₁ | H | H | H | H | 2-Cl | 4-Cl |
| W.210 | B₁ | CH₃ | H | H | H | 2-Cl | 4-Cl |
| W.211 | B₁ | CH₂CH₃ | H | H | H | 2-Cl | 4-Cl |
| W.212 | B₁ | F | H | H | H | 2-Cl | 4-Cl |
| W.213 | B₁ | CN | H | H | H | 2-Cl | 4-Cl |
| W.214 | B₁ | H | CH₃ | H | H | 2-Cl | 4-Cl |
| W.215 | B₁ | CH₃ | CH₃ | H | H | 2-Cl | 4-Cl |
| W.216 | B₁ | CH₂CH₃ | CH₃ | H | H | 2-Cl | 4-Cl |
| W.217 | B₁ | F | CH₃ | H | H | 2-Cl | 4-Cl |
| W.218 | B₁ | CN | CH₃ | H | H | 2-Cl | 4-Cl |
| W.219 | B₁ | H | CH₂CH₃ | H | H | 2-Cl | 4-Cl |
| W.220 | B₁ | CH₃ | CH₂CH₃ | H | H | 2-Cl | 4-Cl |
| W.221 | B₁ | F | CH₂CH₃ | H | H | 2-Cl | 4-Cl |
| W.222 | B₁ | CN | CH₂CH₃ | H | H | 2-Cl | 4-Cl |
| W.223 | B₁ | H | H | F | H | 2-Cl | 4-Cl |
| W.224 | B₁ | CH₃ | H | F | H | 2-Cl | 4-Cl |
| W.225 | B₁ | F | H | F | H | 2-Cl | 4-Cl |
| W.226 | B₁ | H | CH₃ | F | H | 2-Cl | 4-Cl |
| W.227 | B₁ | CH₃ | CH₃ | F | H | 2-Cl | 4-Cl |
| W.228 | B₁ | F | CH₃ | F | H | 2-Cl | 4-Cl |
| W.229 | B₁ | H | H | F | F | 2-Cl | 4-Cl |
| W.230 | B₁ | H | H | CH₃ | CH₃ | 2-Cl | 4-Cl |
| W.231 | B₁ | F | H | CH₃ | CH₃ | 2-Cl | 4-Cl |
| W.232 | B₁ | H | CH₃ | CH₃ | CH₃ | 2-Cl | 4-Cl |
| W.233 | B₁ | CH₃ | CH₃ | CH₃ | CH₃ | 2-Cl | 4-Cl |
| W.234 | B₁ | F | CH₃ | CH₃ | CH₃ | 2-Cl | 4-Cl |
| W.235 | B₁ | H | H | H | H | 2-p-Cl-phenyl | 4-Cl |
| W.236 | B₁ | CH₃ | H | H | H | 2-p-Cl-phenyl | 4-Cl |
| W.237 | B₁ | CH₂CH₃ | H | H | H | 2-p-Cl-phenyl | 4-Cl |
| W.238 | B₁ | F | H | H | H | 2-p-Cl-phenyl | 4-Cl |
| W.239 | B₁ | CN | H | H | H | 2-p-Cl-phenyl | 4-Cl |
| W.240 | B₁ | H | CH₃ | H | H | 2-p-Cl-phenyl | 4-Cl |
| W.241 | B₁ | CH₃ | CH₃ | H | H | 2-p-Cl-phenyl | 4-Cl |
| W.242 | B₁ | CH₂CH₃ | CH₃ | H | H | 2-p-Cl-phenyl | 4-Cl |
| W.243 | B₁ | F | CH₃ | H | H | 2-p-Cl-phenyl | 4-Cl |
| W.244 | B₁ | CN | CH₃ | H | H | 2-p-Cl-phenyl | 4-Cl |
| W.245 | B₁ | H | CH₂CH₃ | H | H | 2-p-Cl-phenyl | 4-Cl |
| W.246 | B₁ | CH₃ | CH₂CH₃ | H | H | 2-p-Cl-phenyl | 4-Cl |
| W.247 | B₁ | F | CH₂CH₃ | H | H | 2-p-Cl-phenyl | 4-Cl |
| W.248 | B₁ | CN | CH₂CH₃ | H | H | 2-p-Cl-phenyl | 4-Cl |
| W.249 | B₁ | H | H | F | H | 2-p-Cl-phenyl | 4-Cl |
| W.250 | B₁ | CH₃ | H | F | H | 2-p-Cl-phenyl | 4-Cl |
| W.251 | B₁ | F | H | F | H | 2-p-Cl-phenyl | 4-Cl |
| W.252 | B₁ | H | CH₃ | F | H | 2-p-Cl-phenyl | 4-Cl |
| W.253 | B₁ | CH₃ | CH₃ | F | H | 2-p-Cl-phenyl | 4-Cl |
| 254 | B₁ | F | CH₃ | F | H | 2-p-Cl-phenyl | 4-Cl |
| W.255 | B₁ | H | H | F | F | 2-p-Cl-phenyl | 4-Cl |
| W.256 | B₁ | H | H | CH₃ | CH₃ | 2-p-Cl-phenyl | 4-Cl |
| W.257 | B₂ | H | H | H | H | 6-Cl | H |
| W.258 | B₂ | CH₃ | H | H | H | 6-Cl | H |
| W.259 | B₂ | CH₂CH₃ | H | H | H | 6-Cl | H |
| W.260 | B₂ | F | H | H | H | 6-Cl | H |

TABLE W-continued

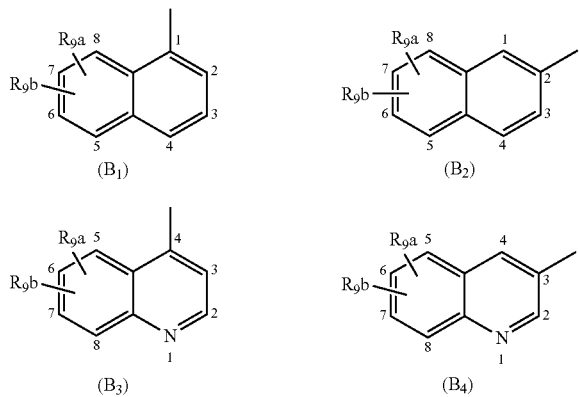

| Compound No. | B | R₁ | R₂ | R₃ | R₄ | R₉ₐ | R₉ᵦ |
|---|---|---|---|---|---|---|---|
| W.261 | B₂ | CN | H | H | H | 6-Cl | H |
| W.262 | B₂ | H | CH₃ | H | H | 6-Cl | H |
| W.263 | B₂ | CH₃ | CH₃ | H | H | 6-Cl | H |
| W.264 | B₂ | CH₂CH₃ | CH₃ | H | H | 6-Cl | H |
| W.265 | B₂ | F | CH₃ | H | H | 6-Cl | H |
| W.266 | B₂ | CN | CH₃ | H | H | 6-Cl | H |
| W.267 | B₂ | H | CH₂CH₃ | H | H | 6-Cl | H |
| W.268 | B₂ | CH₃ | CH₂CH₃ | H | H | 6-Cl | H |
| W.269 | B₂ | F | CH₂CH₃ | H | H | 6-Cl | H |
| W.270 | B₂ | CN | CH₂CH₃ | H | H | 6-Cl | H |
| W.271 | B₂ | H | H | F | H | 6-Cl | H |
| W.272 | B₂ | CH₃ | H | F | H | 6-Cl | H |
| W.273 | B₂ | F | H | F | H | 6-Cl | H |
| W.274 | B₂ | H | CH₃ | F | H | 6-Cl | H |
| W.275 | B₂ | CH₃ | CH₃ | F | H | 6-Cl | H |
| W.276 | B₂ | F | CH₃ | F | H | 6-Cl | H |
| W.277 | B₂ | H | H | F | F | 6-Cl | H |
| W.278 | B₂ | H | H | CH₃ | CH₃ | 6-Cl | H |
| W.279 | B₂ | F | H | CH₃ | CH₃ | 6-Cl | H |
| W.280 | B₂ | H | CH₃ | CH₃ | CH₃ | 6-Cl | H |
| W.281 | B₂ | CH₃ | CH₃ | CH₃ | CH₃ | 6-Cl | H |
| W.282 | B₂ | F | CH₃ | CH₃ | CH₃ | 6-Cl | H |
| W.283 | B₂ | H | H | H | H | 6-OCF₃ | H |
| W.284 | B₂ | CH₃ | H | H | H | 6-OCF₃ | H |
| W.285 | B₂ | CH₂CH₃ | H | H | H | 6-OCF₃ | H |
| W.286 | B₂ | F | H | H | H | 6-OCF₃ | H |
| W.287 | B₂ | CN | H | H | H | 6-OCF₃ | H |
| W.288 | B₂ | H | CH₃ | H | H | 6-OCF₃ | H |
| W.289 | B₂ | CH₃ | CH₃ | H | H | 6-OCF₃ | H |
| W.290 | B₂ | CH₂CH₃ | CH₃ | H | H | 6-OCF₃ | H |
| W.291 | B₂ | F | CH₃ | H | H | 6-OCF₃ | H |
| W.292 | B₂ | CN | CH₃ | H | H | 6-OCF₃ | H |
| W.293 | B₂ | H | CH₂CH₃ | H | H | 6-OCF₃ | H |
| W.294 | B₂ | CH₃ | CH₂CH₃ | H | H | 6-OCF₃ | H |
| W.295 | B₂ | F | CH₂CH₃ | H | H | 6-OCF₃ | H |
| W.296 | B₂ | CN | CH₂CH₃ | H | H | 6-OCF₃ | H |
| W.297 | B₂ | H | H | F | H | 6-OCF₃ | H |
| W.298 | B₂ | CH₃ | H | F | H | 6-OCF₃ | H |
| W.299 | B₂ | F | H | F | H | 6-OCF₃ | H |
| W.300 | B₂ | H | CH₃ | F | H | 6-OCF₃ | H |
| W.301 | B₂ | CH₃ | CH₃ | F | H | 6-OCF₃ | H |
| W.302 | B₂ | F | CH₃ | F | H | 6-OCF₃ | H |
| W.303 | B₂ | H | H | F | F | 6-OCF₃ | H |
| W.304 | B₂ | H | H | CH₃ | CH₃ | 6-OCF₃ | H |
| W.305 | B₂ | F | H | CH₃ | CH₃ | 6-OCF₃ | H |
| W.306 | B₂ | H | CH₃ | CH₃ | CH₃ | 6-OCF₃ | H |
| W.307 | B₂ | CH₃ | CH₃ | CH₃ | CH₃ | 6-OCF₃ | H |
| W.308 | B₂ | F | CH₃ | CH₃ | CH₃ | 6-OCF₃ | H |
| W.309 | B₂ | H | H | H | H | 6-CF₃ | H |
| W.310 | B₂ | CH₃ | H | H | H | 6-CF₃ | H |
| W.311 | B₂ | CH₂CH₃ | H | H | H | 6-CF₃ | H |
| W.312 | B₂ | F | H | H | H | 6-CF₃ | H |
| W.313 | B₂ | CN | H | H | H | 6-CF₃ | H |
| W.314 | B₂ | H | CH₃ | H | H | 6-CF₃ | H |
| W.315 | B₂ | CH₃ | CH₃ | H | H | 6-CF₃ | H |
| W.316 | B₂ | CH₂CH₃ | CH₃ | H | H | 6-CF₃ | H |
| W.317 | B₂ | F | CH₃ | H | H | 6-CF₃ | H |

TABLE W-continued

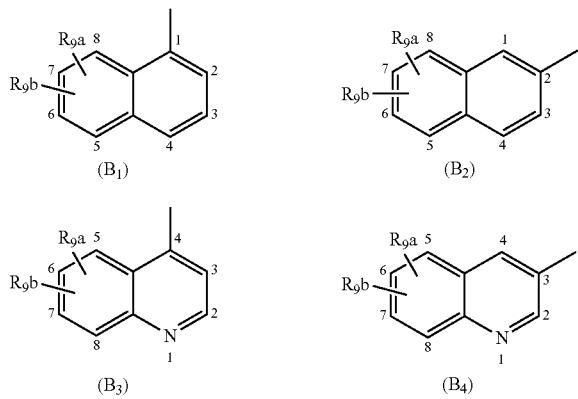

| Compound No. | B | R₁ | R₂ | R₃ | R₄ | R₉ₐ | R₉ᵦ |
|---|---|---|---|---|---|---|---|
| W.318 | B₂ | CN | CH₃ | H | H | 6-CF₃ | H |
| W.319 | B₂ | H | CH₂CH₃ | H | H | 6-CF₃ | H |
| W.320 | B₂ | CH₃ | CH₂CH₃ | H | H | 6-CF₃ | H |
| W.321 | B₂ | F | CH₂CH₃ | H | H | 6-CF₃ | H |
| W.322 | B₂ | CN | CH₂CH₃ | H | H | 6-CF₃ | H |
| W.323 | B₂ | H | H | F | H | 6-CF₃ | H |
| W.324 | B₂ | CH₃ | H | F | H | 6-CF₃ | H |
| W.325 | B₂ | F | H | F | H | 6-CF₃ | H |
| W.326 | B₂ | H | CH₃ | F | H | 6-CF₃ | H |
| W.327 | B₂ | CH₃ | CH₃ | F | H | 6-CF₃ | H |
| W.328 | B₂ | F | CH₃ | F | H | 6-CF₃ | H |
| W.329 | B₂ | H | H | F | F | 6-CF₃ | H |
| W.330 | B₂ | H | H | CH₃ | CH₃ | 6-CF₃ | H |
| W.331 | B₂ | F | H | CH₃ | CH₃ | 6-CF₃ | H |
| W.332 | B₂ | H | CH₃ | CH₃ | CH₃ | 6-CF₃ | H |
| W.333 | B₂ | CH₃ | CH₃ | CH₃ | CH₃ | 6-CF₃ | H |
| W.334 | B₂ | F | CH₃ | CH₃ | CH₃ | 6-CF₃ | H |
| W.335 | B₂ | H | H | H | H | 6-p-Cl-phenyl | H |
| W.336 | B₂ | CH₃ | H | H | H | 6-p-Cl-phenyl | H |
| W.337 | B₂ | CH₂CH₃ | H | H | H | 6-p-Cl-phenyl | H |
| W.338 | B₂ | F | H | H | H | 6-p-Cl-phenyl | H |
| W.339 | B₂ | CN | H | H | H | 6-p-Cl-phenyl | H |
| W.340 | B₂ | H | CH₃ | H | H | 6-p-Cl-phenyl | H |
| W.341 | B₂ | CH₃ | CH₃ | H | H | 6-p-Cl-phenyl | H |
| W.342 | B₂ | CH₂CH₃ | CH₃ | H | H | 6-p-Cl-phenyl | H |
| W.343 | B₂ | F | CH₃ | H | H | 6-p-Cl-phenyl | H |
| W.344 | B₂ | CN | CH₃ | H | H | 6-p-Cl-phenyl | H |
| W.345 | B₂ | H | CH₂CH₃ | H | H | 6-p-Cl-phenyl | H |
| W.346 | B₂ | CH₃ | CH₂CH₃ | H | H | 6-p-Cl-phenyl | H |
| W.347 | B₂ | F | CH₂CH₃ | H | H | 6-p-Cl-phenyl | H |
| W.348 | B₂ | CN | CH₂CH₃ | H | H | 6-p-Cl-phenyl | H |
| W.349 | B₂ | H | H | F | H | 6-p-Cl-phenyl | H |
| W.350 | B₂ | CH₃ | H | F | H | 6-p-Cl-phenyl | H |
| W.351 | B₂ | F | H | F | H | 6-p-Cl-phenyl | H |
| W.352 | B₂ | H | CH₃ | F | H | 6-p-Cl-phenyl | H |
| W.353 | B₂ | CH₃ | CH₃ | F | H | 6-p-Cl-phenyl | H |
| W.354 | B₂ | F | CH₃ | F | H | 6-p-Cl-phenyl | H |
| W.355 | B₂ | H | H | F | F | 6-p-Cl-phenyl | H |
| W.356 | B₂ | H | H | CH₃ | CH₃ | 6-p-Cl-phenyl | H |
| W.357 | B₂ | F | H | CH₃ | CH₃ | 6-p-Cl-phenyl | H |
| W.358 | B₂ | H | CH₃ | CH₃ | CH₃ | 6-p-Cl-phenyl | H |
| W.359 | B₂ | CH₃ | CH₃ | CH₃ | CH₃ | 6-p-Cl-phenyl | H |
| W.360 | B₂ | F | CH₃ | CH₃ | CH₃ | 6-p-Cl-phenyl | H |
| W.361 | B₃ | H | H | H | H | 2-Cl | H |
| W.362 | B₃ | CH₃ | H | H | H | 2-Cl | H |
| W.363 | B₃ | CH₂CH₃ | H | H | H | 2-Cl | H |
| W.364 | B₃ | F | H | H | H | 2-Cl | H |
| W.365 | B₃ | CN | H | H | H | 2-Cl | H |
| W.366 | B₃ | H | CH₃ | H | H | 2-Cl | H |
| W.367 | B₃ | CH₃ | CH₃ | H | H | 2-Cl | H |
| W.368 | B₃ | CH₂CH₃ | CH₃ | H | H | 2-Cl | H |
| W.369 | B₃ | F | CH₃ | H | H | 2-Cl | H |
| W.370 | B₃ | CN | CH₃ | H | H | 2-Cl | H |
| W.371 | B₃ | H | CH₂CH₃ | H | H | 2-Cl | H |
| W.372 | B₃ | CH₃ | CH₂CH₃ | H | H | 2-Cl | H |
| W.373 | B₃ | F | CH₂CH₃ | H | H | 2-Cl | H |
| W.374 | B₃ | CN | CH₂CH₃ | H | H | 2-Cl | H |

TABLE W-continued

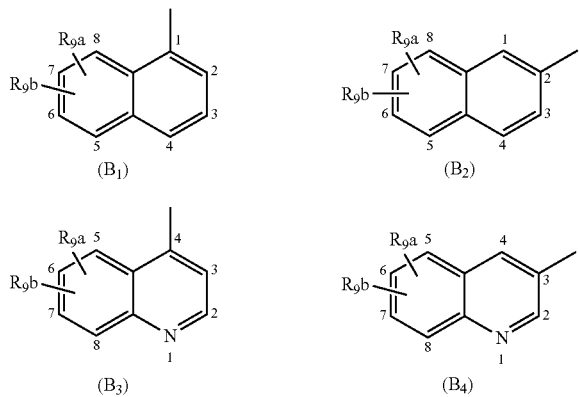

| Compound No. | B | R$_1$ | R$_2$ | R$_3$ | R$_4$ | R$_{9a}$ | R$_{9b}$ |
|---|---|---|---|---|---|---|---|
| W.375 | B$_3$ | H | H | F | H | 2-Cl | H |
| W.376 | B$_3$ | CH$_3$ | H | F | H | 2-Cl | H |
| W.377 | B$_3$ | F | H | F | H | 2-Cl | H |
| W.378 | B$_3$ | H | CH$_3$ | F | H | 2-Cl | H |
| W.379 | B$_3$ | CH$_3$ | CH$_3$ | F | H | 2-Cl | H |
| W.380 | B$_3$ | F | CH$_3$ | F | H | 2-Cl | H |
| W.381 | B$_3$ | H | H | F | F | 2-Cl | H |
| W.382 | B$_3$ | H | H | CH$_3$ | CH$_3$ | 2-Cl | H |
| W.383 | B$_3$ | F | H | CH$_3$ | CH$_3$ | 2-Cl | H |
| W.384 | B$_3$ | H | CH$_3$ | CH$_3$ | CH$_3$ | 2-Cl | H |
| W.385 | B$_3$ | CH$_3$ | CH$_3$ | CH$_3$ | CH$_3$ | 2-Cl | H |
| W.386 | B$_3$ | F | CH$_3$ | CH$_3$ | CH$_3$ | 2-Cl | H |
| W.387 | B$_3$ | H | H | H | H | 3-Cl | H |
| W.388 | B$_3$ | CH$_3$ | H | H | H | 3-Cl | H |
| W.389 | B$_3$ | CH$_2$CH$_3$ | H | H | H | 3-Cl | H |
| W.390 | B$_3$ | F | H | H | H | 3-Cl | H |
| W.391 | B$_3$ | CN | H | H | H | 3-Cl | H |
| W.392 | B$_3$ | H | CH$_3$ | H | H | 3-Cl | H |
| W.393 | B$_3$ | CH$_3$ | CH$_3$ | H | H | 3-Cl | H |
| W.394 | B$_3$ | CH$_2$CH$_3$ | CH$_3$ | H | H | 3-Cl | H |
| W.395 | B$_3$ | F | CH$_3$ | H | H | 3-Cl | H |
| W.396 | B$_3$ | CN | CH$_3$ | H | H | 3-Cl | H |
| W.397 | B$_3$ | H | CH$_2$CH$_3$ | H | H | 3-Cl | H |
| W.398 | B$_3$ | CH$_3$ | CH$_2$CH$_3$ | H | H | 3-Cl | H |
| W.399 | B$_3$ | F | CH$_2$CH$_3$ | H | H | 3-Cl | H |
| W.400 | B$_3$ | CN | CH$_2$CH$_3$ | H | H | 3-Cl | H |
| W.401 | B$_3$ | H | H | F | H | 3-Cl | H |
| W.402 | B$_3$ | CH$_3$ | H | F | H | 3-Cl | H |
| W.403 | B$_3$ | F | H | F | H | 3-Cl | H |
| W.404 | B$_3$ | H | CH$_3$ | F | H | 3-Cl | H |
| W.405 | B$_3$ | CH$_3$ | CH$_3$ | F | H | 3-Cl | H |
| W.406 | B$_3$ | F | CH$_3$ | F | H | 3-Cl | H |
| W.407 | B$_3$ | H | H | F | F | 3-Cl | H |
| W.408 | B$_3$ | H | H | CH$_3$ | CH$_3$ | 3-Cl | H |
| W.409 | B$_3$ | F | H | CH$_3$ | CH$_3$ | 3-Cl | H |
| W.410 | B$_3$ | H | CH$_3$ | CH$_3$ | CH$_3$ | 3-Cl | H |
| W.411 | B$_3$ | CH$_3$ | CH$_3$ | CH$_3$ | CH$_3$ | 3-Cl | H |
| W.412 | B$_3$ | F | CH$_3$ | CH$_3$ | CH$_3$ | 3-Cl | H |
| W.413 | B$_3$ | H | H | H | H | 6-Cl | H |
| W.414 | B$_3$ | CH$_3$ | H | H | H | 6-Cl | H |
| W.415 | B$_3$ | CH$_2$CH$_3$ | H | H | H | 6-Cl | H |
| W.416 | B$_3$ | F | H | H | H | 6-Cl | H |
| W.417 | B$_3$ | CN | H | H | H | 6-Cl | H |
| W.418 | B$_3$ | H | CH$_3$ | H | H | 6-Cl | H |
| W.419 | B$_3$ | CH$_3$ | CH$_3$ | H | H | 6-Cl | H |
| W.420 | B$_3$ | CH$_2$CH$_3$ | CH$_3$ | H | H | 6-Cl | H |
| W.421 | B$_3$ | F | CH$_3$ | H | H | 6-Cl | H |
| W.422 | B$_3$ | CN | CH$_3$ | H | H | 6-Cl | H |
| W.423 | B$_3$ | H | CH$_2$CH$_3$ | H | H | 6-Cl | H |
| W.424 | B$_3$ | CH$_3$ | CH$_2$CH$_3$ | H | H | 6-Cl | H |
| W.425 | B$_3$ | F | CH$_2$CH$_3$ | H | H | 6-Cl | H |
| W.426 | B$_3$ | CN | CH$_2$CH$_3$ | H | H | 6-Cl | H |
| W.427 | B$_3$ | H | H | F | H | 6-Cl | H |
| W.428 | B$_3$ | CH$_3$ | H | F | H | 6-Cl | H |
| W.429 | B$_3$ | F | H | F | H | 6-Cl | H |
| W.430 | B$_3$ | H | CH$_3$ | F | H | 6-Cl | H |
| W.431 | B$_3$ | CH$_3$ | CH$_3$ | F | H | 6-Cl | H |

TABLE W-continued

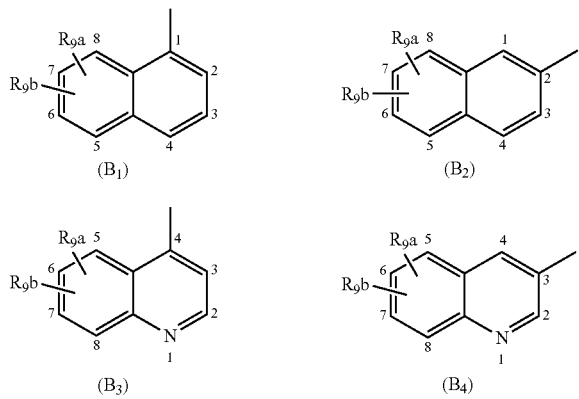

| Compound No. | B | R₁ | R₂ | R₃ | R₄ | R₉ₐ | R₉ᵦ |
|---|---|---|---|---|---|---|---|
| W.432 | B₃ | F | CH₃ | F | H | 6-Cl | H |
| W.433 | B₃ | H | H | F | F | 6-Cl | H |
| W.434 | B₃ | H | H | CH₃ | CH₃ | 6-Cl | H |
| W.435 | B₃ | F | H | CH₃ | CH₃ | 6-Cl | H |
| W.436 | B₃ | H | CH₃ | CH₃ | CH₃ | 6-Cl | H |
| W.437 | B₃ | CH₃ | CH₃ | CH₃ | CH₃ | 6-Cl | H |
| W.438 | B₃ | F | CH₃ | CH₃ | CH₃ | 6-Cl | H |
| W.439 | B₃ | H | H | H | H | 7-Cl | H |
| W.440 | B₃ | CH₃ | H | H | H | 7-Cl | H |
| W.441 | B₃ | CH₂CH₃ | H | H | H | 7-Cl | H |
| W.442 | B₃ | F | H | H | H | 7-Cl | H |
| W.443 | B₃ | CN | H | H | H | 7-Cl | H |
| W.444 | B₃ | H | CH₃ | H | H | 7-Cl | H |
| W.445 | B₃ | CH₃ | CH₃ | H | H | 7-Cl | H |
| W.446 | B₃ | CH₂CH₃ | CH₃ | H | H | 7-Cl | H |
| W.447 | B₃ | F | CH₃ | H | H | 7-Cl | H |
| W.448 | B₃ | CN | CH₃ | H | H | 7-Cl | H |
| W.449 | B₃ | H | CH₂CH₃ | H | H | 7-Cl | H |
| W.450 | B₃ | CH₃ | CH₂CH₃ | H | H | 7-Cl | H |
| W.451 | B₃ | F | CH₂CH₃ | H | H | 7-Cl | H |
| W.452 | B₃ | CN | CH₂CH₃ | H | H | 7-Cl | H |
| W.453 | B₃ | H | H | F | H | 7-Cl | H |
| W.454 | B₃ | CH₃ | H | F | H | 7-Cl | H |
| W.455 | B₃ | F | H | F | H | 7-Cl | H |
| W.456 | B₃ | H | CH₃ | F | H | 7-Cl | H |
| W.457 | B₃ | CH₃ | CH₃ | F | H | 7-Cl | H |
| W.458 | B₃ | F | CH₃ | F | H | 7-Cl | H |
| W.459 | B₃ | H | H | F | F | 7-Cl | H |
| W.460 | B₃ | H | H | CH₃ | CH₃ | 7-Cl | H |
| W.461 | B₃ | F | H | CH₃ | CH₃ | 7-Cl | H |
| W.462 | B₃ | H | CH₃ | CH₃ | CH₃ | 7-Cl | H |
| W.463 | B₃ | CH₃ | CH₃ | CH₃ | CH₃ | 7-Cl | H |
| W.464 | B₃ | F | CH₃ | CH₃ | CH₃ | 7-Cl | H |
| W.465 | B₃ | H | H | H | H | 8-Cl | H |
| W.466 | B₃ | CH₃ | H | H | H | 8-Cl | H |
| W.467 | B₃ | CH₂CH₃ | H | H | H | 8-Cl | H |
| W.468 | B₃ | F | H | H | H | 8-Cl | H |
| W.469 | B₃ | CN | H | H | H | 8-Cl | H |
| W.470 | B₃ | H | CH₃ | H | H | 8-Cl | H |
| W.471 | B₃ | CH₃ | CH₃ | H | H | 8-Cl | H |
| W.472 | B₃ | CH₂CH₃ | CH₃ | H | H | 8-Cl | H |
| W.473 | B₃ | F | CH₃ | H | H | 8-Cl | H |
| W.474 | B₃ | CN | CH₃ | H | H | 8-Cl | H |
| W.475 | B₃ | H | CH₂CH₃ | H | H | 8-Cl | H |
| W.476 | B₃ | CH₃ | CH₂CH₃ | H | H | 8-Cl | H |
| W.477 | B₃ | F | CH₂CH₃ | H | H | 8-Cl | H |
| W.478 | B₃ | CN | CH₂CH₃ | H | H | 8-Cl | H |
| W.479 | B₃ | H | H | F | H | 8-Cl | H |
| W.480 | B₃ | CH₃ | H | F | H | 8-Cl | H |
| W.481 | B₃ | F | H | F | H | 8-Cl | H |
| W.482 | B₃ | H | CH₃ | F | H | 8-Cl | H |
| W.483 | B₃ | CH₃ | CH₃ | F | H | 8-Cl | H |
| W.484 | B₃ | F | CH₃ | F | H | 8-Cl | H |
| W.485 | B₃ | H | H | F | F | 8-Cl | H |
| W.486 | B₃ | H | H | CH₃ | CH₃ | 8-Cl | H |
| W.487 | B₃ | F | H | CH₃ | CH₃ | 8-Cl | H |
| W.488 | B₃ | H | CH₃ | CH₃ | CH₃ | 8-Cl | H |

TABLE W-continued

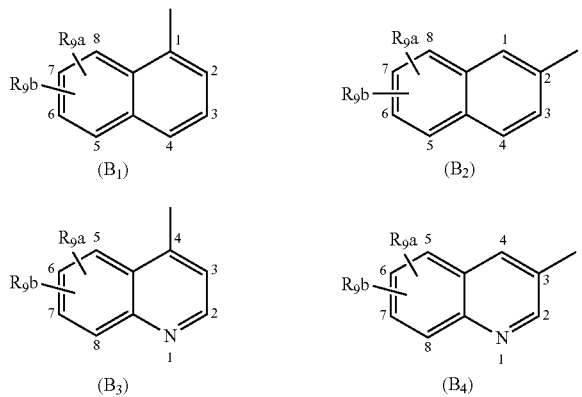

| Compound No. | B | $R_1$ | $R_2$ | $R_3$ | $R_4$ | $R_{9a}$ | $R_{9b}$ |
|---|---|---|---|---|---|---|---|
| W.489 | $B_3$ | $CH_3$ | $CH_3$ | $CH_3$ | $CH_3$ | 8-Cl | H |
| W.490 | $B_3$ | F | $CH_3$ | $CH_3$ | $CH_3$ | 8-Cl | H |
| W.491 | $B_3$ | H | H | H | H | 2-Cl | 5-Cl |
| W.492 | $B_3$ | $CH_3$ | H | H | H | 2-Cl | 5-Cl |
| W.493 | $B_3$ | $CH_2CH_3$ | H | H | H | 2-Cl | 5-Cl |
| W.494 | $B_3$ | F | H | H | H | 2-Cl | 5-Cl |
| W.495 | $B_3$ | CN | H | H | H | 2-Cl | 5-Cl |
| W.496 | $B_3$ | H | $CH_3$ | H | H | 2-Cl | 5-Cl |
| W.497 | $B_3$ | $CH_3$ | $CH_3$ | H | H | 2-Cl | 5-Cl |
| W.498 | $B_3$ | $CH_2CH_3$ | $CH_3$ | H | H | 2-Cl | 5-Cl |
| W.499 | $B_3$ | F | $CH_3$ | H | H | 2-Cl | 5-Cl |
| W.500 | $B_3$ | CN | $CH_3$ | H | H | 2-Cl | 5-Cl |
| W.501 | $B_3$ | H | $CH_2CH_3$ | H | H | 2-Cl | 5-Cl |
| W.502 | $B_3$ | $CH_3$ | $CH_2CH_3$ | H | H | 2-Cl | 5-Cl |
| W.503 | $B_3$ | F | $CH_2CH_3$ | H | H | 2-Cl | 5-Cl |
| W.504 | $B_3$ | CN | $CH_2CH_3$ | H | H | 2-Cl | 5-Cl |
| W.505 | $B_3$ | H | H | F | H | 2-Cl | 5-Cl |
| W.506 | $B_3$ | $CH_3$ | H | F | H | 2-Cl | 5-Cl |
| W.507 | $B_3$ | F | H | F | H | 2-Cl | 5-Cl |
| W.508 | $B_3$ | H | $CH_3$ | F | H | 2-Cl | 5-Cl |
| W.509 | $B_3$ | $CH_3$ | $CH_3$ | F | H | 2-Cl | 5-Cl |
| W.510 | $B_3$ | F | $CH_3$ | F | H | 2-Cl | 5-Cl |
| W.511 | $B_3$ | H | H | F | F | 2-Cl | 5-Cl |
| W.512 | $B_3$ | H | H | $CH_3$ | $CH_3$ | 2-Cl | 5-Cl |
| W.513 | $B_3$ | F | H | $CH_3$ | $CH_3$ | 2-Cl | 5-Cl |
| W.514 | $B_3$ | H | $CH_3$ | $CH_3$ | $CH_3$ | 2-Cl | 5-Cl |
| W.515 | $B_3$ | $CH_3$ | $CH_3$ | $CH_3$ | $CH_3$ | 2-Cl | 5-Cl |
| W.516 | $B_3$ | F | $CH_3$ | $CH_3$ | $CH_3$ | 2-Cl | 6-Cl |
| W.517 | $B_3$ | H | H | H | H | 2-Cl | 6-Cl |
| W.518 | $B_3$ | $CH_3$ | H | H | H | 2-Cl | 6-Cl |
| W.519 | $B_3$ | $CH_2CH_3$ | H | H | H | 2-Cl | 6-Cl |
| W.520 | $B_3$ | F | H | H | H | 2-Cl | 6-Cl |
| W.521 | $B_3$ | CN | H | H | H | 2-Cl | 6-Cl |
| W.522 | $B_3$ | H | $CH_3$ | H | H | 2-Cl | 6-Cl |
| W.523 | $B_3$ | $CH_3$ | $CH_3$ | H | H | 2-Cl | 6-Cl |
| W.524 | $B_3$ | $CH_2CH_3$ | $CH_3$ | H | H | 2-Cl | 6-Cl |
| W.525 | $B_3$ | F | $CH_3$ | H | H | 2-Cl | 6-Cl |
| W.526 | $B_3$ | CN | $CH_3$ | H | H | 2-Cl | 6-Cl |
| W.527 | $B_3$ | H | $CH_2CH_3$ | H | H | 2-Cl | 6-Cl |
| W.528 | $B_3$ | $CH_3$ | $CH_2CH_3$ | H | H | 2-Cl | 6-Cl |
| W.529 | $B_3$ | F | $CH_2CH_3$ | H | H | 2-Cl | 6-Cl |
| W.530 | $B_3$ | CN | $CH_2CH_3$ | H | H | 2-Cl | 6-Cl |
| W.531 | $B_3$ | H | H | F | H | 2-Cl | 6-Cl |
| W.532 | $B_3$ | $CH_3$ | H | F | H | 2-Cl | 6-Cl |
| W.533 | $B_3$ | F | H | F | H | 2-Cl | 6-Cl |
| W.534 | $B_3$ | H | $CH_3$ | F | H | 2-Cl | 6-Cl |
| W.535 | $B_3$ | $CH_3$ | $CH_3$ | F | H | 2-Cl | 6-Cl |
| W.536 | $B_3$ | F | $CH_3$ | F | H | 2-Cl | 6-Cl |
| W.537 | $B_3$ | H | H | F | F | 2-Cl | 6-Cl |
| W.538 | $B_3$ | H | H | $CH_3$ | $CH_3$ | 2-Cl | 6-Cl |
| W.539 | $B_3$ | F | H | $CH_3$ | $CH_3$ | 2-Cl | 6-Cl |
| W.540 | $B_3$ | H | $CH_3$ | $CH_3$ | $CH_3$ | 2-Cl | 6-Cl |
| W.541 | $B_3$ | $CH_3$ | $CH_3$ | $CH_3$ | $CH_3$ | 2-Cl | 6-Cl |
| W.542 | $B_3$ | F | $CH_3$ | $CH_3$ | $CH_3$ | 2-Cl | 6-Cl |
| 243 | $B_3$ | H | H | H | H | 2-Cl | 7-Cl |
| W.544 | $B_3$ | $CH_3$ | H | H | H | 2-Cl | 7-Cl |
| W.545 | $B_3$ | $CH_2CH_3$ | H | H | H | 2-Cl | 7-Cl |

TABLE W-continued

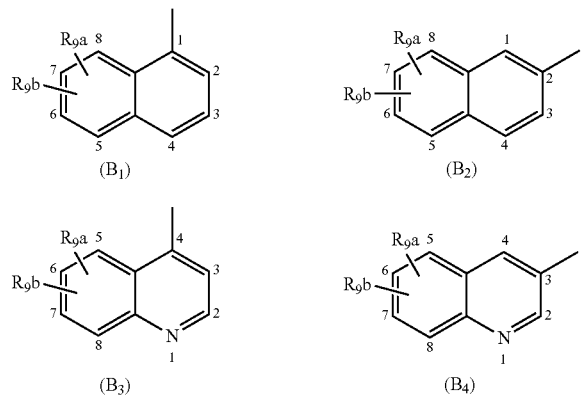

| Compound No. | B | $R_1$ | $R_2$ | $R_3$ | $R_4$ | $R_{9a}$ | $R_{9b}$ |
|---|---|---|---|---|---|---|---|
| W.546 | $B_3$ | F | H | H | H | 2-Cl | 7-Cl |
| W.547 | $B_3$ | CN | H | H | H | 2-Cl | 7-Cl |
| W.548 | $B_3$ | H | $CH_3$ | H | H | 2-Cl | 7-Cl |
| W.549 | $B_3$ | $CH_3$ | $CH_3$ | H | H | 2-Cl | 7-Cl |
| W.550 | $B_3$ | $CH_2CH_3$ | $CH_3$ | H | H | 2-Cl | 7-Cl |
| W.551 | $B_3$ | F | $CH_3$ | H | H | 2-Cl | 7-Cl |
| W.552 | $B_3$ | CN | $CH_3$ | H | H | 2-Cl | 7-Cl |
| W.553 | $B_3$ | H | $CH_2CH_3$ | H | H | 2-Cl | 7-Cl |
| W.554 | $B_3$ | $CH_3$ | $CH_2CH_3$ | H | H | 2-Cl | 7-Cl |
| W.555 | $B_3$ | F | $CH_2CH_3$ | H | H | 2-Cl | 7-Cl |
| W.556 | $B_3$ | CN | $CH_2CH_3$ | H | H | 2-Cl | 7-Cl |
| W.557 | $B_3$ | H | H | F | H | 2-Cl | 7-Cl |
| W.558 | $B_3$ | $CH_3$ | H | F | H | 2-Cl | 7-Cl |
| W.559 | $B_3$ | F | H | F | H | 2-Cl | 7-Cl |
| W.560 | $B_3$ | H | $CH_3$ | F | H | 2-Cl | 7-Cl |
| W.561 | $B_3$ | $CH_3$ | $CH_3$ | F | H | 2-Cl | 7-Cl |
| W.562 | $B_3$ | F | $CH_3$ | F | H | 2-Cl | 7-Cl |
| W.563 | $B_3$ | H | H | F | F | 2-Cl | 7-Cl |
| W.564 | $B_3$ | H | H | $CH_3$ | $CH_3$ | 2-Cl | 7-Cl |
| W.565 | $B_3$ | F | H | $CH_3$ | $CH_3$ | 2-Cl | 7-Cl |
| W.566 | $B_3$ | H | $CH_3$ | $CH_3$ | $CH_3$ | 2-Cl | 7-Cl |
| W.567 | $B_3$ | $CH_3$ | $CH_3$ | $CH_3$ | $CH_3$ | 2-Cl | 7-Cl |
| W.568 | $B_3$ | F | $CH_3$ | $CH_3$ | $CH_3$ | 2-Cl | 7-Cl |
| W.569 | $B_3$ | H | H | H | H | 2-Cl | 8-Cl |
| W.570 | $B_3$ | $CH_3$ | H | H | H | 2-Cl | 8-Cl |
| W.571 | $B_3$ | $CH_2CH_3$ | H | H | H | 2-Cl | 8-Cl |
| W.572 | $B_3$ | F | H | H | H | 2-Cl | 8-Cl |
| W.573 | $B_3$ | CN | H | H | H | 2-Cl | 8-Cl |
| W.574 | $B_3$ | H | $CH_3$ | H | H | 2-Cl | 8-Cl |
| W.575 | $B_3$ | $CH_3$ | $CH_3$ | H | H | 2-Cl | 8-Cl |
| W.576 | $B_3$ | $CH_2CH_3$ | $CH_3$ | H | H | 2-Cl | 8-Cl |
| W.577 | $B_3$ | F | $CH_3$ | H | H | 2-Cl | 8-Cl |
| W.578 | $B_3$ | CN | $CH_3$ | H | H | 2-Cl | 8-Cl |
| W.579 | $B_3$ | H | $CH_2CH_3$ | H | H | 2-Cl | 8-Cl |
| W.580 | $B_3$ | $CH_3$ | $CH_2CH_3$ | H | H | 2-Cl | 8-Cl |
| W.581 | $B_3$ | F | $CH_2CH_3$ | H | H | 2-Cl | 8-Cl |
| W.582 | $B_3$ | CN | $CH_2CH_3$ | H | H | 2-Cl | 8-Cl |
| W.583 | $B_3$ | H | H | F | H | 2-Cl | 8-Cl |
| W.584 | $B_3$ | $CH_3$ | H | F | H | 2-Cl | 8-Cl |
| W.585 | $B_3$ | F | H | F | H | 2-Cl | 8-Cl |
| W.586 | $B_3$ | H | $CH_3$ | F | H | 2-Cl | 8-Cl |
| W.587 | $B_3$ | $CH_3$ | $CH_3$ | F | H | 2-Cl | 8-Cl |
| W.588 | $B_3$ | F | $CH_3$ | F | H | 2-Cl | 8-Cl |
| W.589 | $B_3$ | H | H | F | F | 2-Cl | 8-Cl |
| W.590 | $B_3$ | H | H | $CH_3$ | $CH_3$ | 2-Cl | 8-Cl |
| W.591 | $B_3$ | F | H | $CH_3$ | $CH_3$ | 2-Cl | 8-Cl |
| W.592 | $B_3$ | H | $CH_3$ | $CH_3$ | $CH_3$ | 2-Cl | 8-Cl |
| W.593 | $B_3$ | $CH_3$ | $CH_3$ | $CH_3$ | $CH_3$ | 2-Cl | 8-Cl |
| W.594 | $B_3$ | F | $CH_3$ | $CH_3$ | $CH_3$ | 2-Cl | 8-Cl |
| W.595 | $B_3$ | H | H | H | H | 6-p-Cl-phenyl | 2-Cl |
| W.596 | $B_3$ | $CH_3$ | H | H | H | 6-p-Cl-phenyl | 2-Cl |
| W.597 | $B_3$ | $CH_2CH_3$ | H | H | H | 6-p-Cl-phenyl | 2-Cl |
| W.598 | $B_3$ | F | H | H | H | 6-p-Cl-phenyl | 2-Cl |
| W.599 | $B_3$ | CN | H | H | H | 6-p-Cl-phenyl | 2-Cl |
| W.600 | $B_3$ | H | $CH_3$ | H | H | 6-p-Cl-phenyl | 2-Cl |
| W.601 | $B_3$ | $CH_3$ | $CH_3$ | H | H | 6-p-Cl-phenyl | 2-Cl |
| W.602 | $B_3$ | $CH_2CH_3$ | $CH_3$ | H | H | 6-p-Cl-phenyl | 2-Cl |

TABLE W-continued

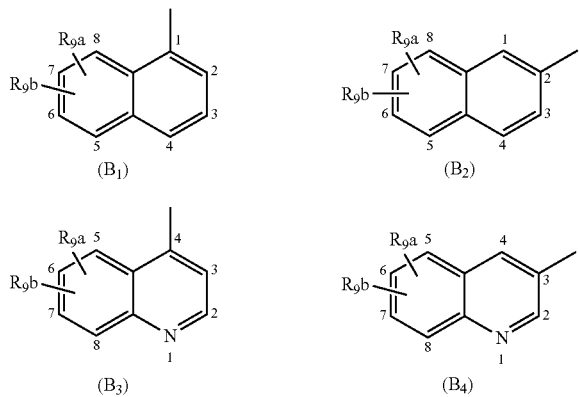

| Compound No. | B | R₁ | R₂ | R₃ | R₄ | R₉ₐ | R₉ᵦ |
|---|---|---|---|---|---|---|---|
| W.603 | B₃ | F | CH₃ | H | H | 6-p-Cl-phenyl | 2-Cl |
| W.604 | B₃ | CN | CH₃ | H | H | 6-p-Cl-phenyl | 2-Cl |
| W.605 | B₃ | H | CH₂CH₃ | H | H | 6-p-Cl-phenyl | 2-Cl |
| W.606 | B₃ | CH₃ | CH₂CH₃ | H | H | 6-p-Cl-phenyl | 2-Cl |
| W.607 | B₃ | F | CH₂CH₃ | H | H | 6-p-Cl-phenyl | 2-Cl |
| W.608 | B₃ | CN | CH₂CH₃ | H | H | 6-p-Cl-phenyl | 2-Cl |
| W.609 | B₃ | H | H | F | H | 6-p-Cl-phenyl | 2-Cl |
| W.610 | B₃ | CH₃ | H | F | H | 6-p-Cl-phenyl | 2-Cl |
| W.611 | B₃ | F | H | F | H | 6-p-Cl-phenyl | 2-Cl |
| W.612 | B₃ | H | CH₃ | F | H | 6-p-Cl-phenyl | 2-Cl |
| W.613 | B₃ | CH₃ | CH₃ | F | H | 6-p-Cl-phenyl | 2-Cl |
| W.614 | B₃ | F | CH₃ | F | H | 6-p-Cl-phenyl | 2-Cl |
| W.615 | B₃ | H | H | F | F | 6-p-Cl-phenyl | 2-Cl |
| W.616 | B₃ | H | H | CH₃ | CH₃ | 6-p-Cl-phenyl | 2-Cl |
| W.617 | B₄ | H | H | H | H | 2-Cl | H |
| W.618 | B₄ | CH₃ | H | H | H | 2-Cl | H |
| W.619 | B₄ | CH₂CH₃ | H | H | H | 2-Cl | H |
| W.620 | B₄ | F | H | H | H | 2-Cl | H |
| W.621 | B₄ | CN | H | H | H | 2-Cl | H |
| W.622 | B₄ | H | CH₃ | H | H | 2-Cl | H |
| W.623 | B₄ | CH₃ | CH₃ | H | H | 2-Cl | H |
| W.624 | B₄ | CH₂CH₃ | CH₃ | H | H | 2-Cl | H |
| W.625 | B₄ | F | CH₃ | H | H | 2-Cl | H |
| W.626 | B₄ | CN | CH₃ | H | H | 2-Cl | H |
| W.627 | B₄ | H | CH₂CH₃ | H | H | 2-Cl | H |
| W.628 | B₄ | CH₃ | CH₂CH₃ | H | H | 2-Cl | H |
| W.629 | B₄ | F | CH₂CH₃ | H | H | 2-Cl | H |
| W.630 | B₄ | CN | CH₂CH₃ | H | H | 2-Cl | H |
| W.631 | B₄ | H | H | F | H | 2-Cl | H |
| W.632 | B₄ | CH₃ | H | F | H | 2-Cl | H |
| W.633 | B₄ | F | H | F | H | 2-Cl | H |
| W.634 | B₄ | H | CH₃ | F | H | 2-Cl | H |
| W.635 | B₄ | CH₃ | CH₃ | F | H | 2-Cl | H |
| W.636 | B₄ | F | CH₃ | F | H | 2-Cl | H |
| W.637 | B₄ | H | H | F | F | 2-Cl | H |
| W.638 | B₄ | H | H | CH₃ | CH₃ | 2-Cl | H |
| W.639 | B₄ | F | H | CH₃ | CH₃ | 2-Cl | H |
| W.640 | B₄ | H | CH₃ | CH₃ | CH₃ | 2-Cl | H |
| W.641 | B₄ | CH₃ | CH₃ | CH₃ | CH₃ | 2-Cl | H |
| W.642 | B₄ | F | CH₃ | CH₃ | CH₃ | 2-Cl | H |
| W.643 | B₄ | H | H | H | H | 4-Cl | H |
| W.644 | B₄ | CH₃ | H | H | H | 4-Cl | H |
| W.645 | B₄ | CH₂CH₃ | H | H | H | 4-Cl | H |
| W.646 | B₄ | F | H | H | H | 4-Cl | H |
| W.647 | B₄ | CN | H | H | H | 4-Cl | H |
| W.648 | B₄ | H | CH₃ | H | H | 4-Cl | H |
| W.649 | B₄ | CH₃ | CH₃ | H | H | 4-Cl | H |
| W.650 | B₄ | CH₂CH₃ | CH₃ | H | H | 4-Cl | H |
| W.651 | B₄ | F | CH₃ | H | H | 4-Cl | H |
| W.652 | B₄ | CN | CH₃ | H | H | 4-Cl | H |
| W.653 | B₄ | H | CH₂CH₃ | H | H | 4-Cl | H |
| W.654 | B₄ | CH₃ | CH₂CH₃ | H | H | 4-Cl | H |
| W.655 | B₄ | F | CH₂CH₃ | H | H | 4-Cl | H |
| W.656 | B₄ | CN | CH₂CH₃ | H | H | 4-Cl | H |
| W.657 | B₄ | H | H | F | H | 4-Cl | H |
| W.658 | B₄ | CH₃ | H | F | H | 4-Cl | H |
| W.659 | B₄ | F | H | F | H | 4-Cl | H |

TABLE W-continued

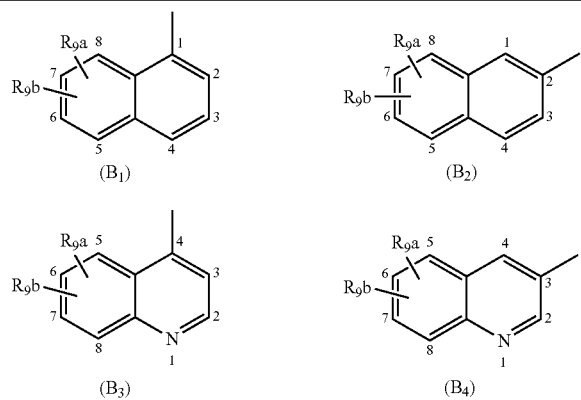

| Compound No. | B | R₁ | R₂ | R₃ | R₄ | R₉ₐ | R₉ᵦ |
|---|---|---|---|---|---|---|---|
| W.660 | B₄ | H | CH₃ | F | H | 4-Cl | H |
| W.661 | B₄ | CH₃ | CH₃ | F | H | 4-Cl | H |
| W.662 | B₄ | F | CH₃ | F | H | 4-Cl | H |
| W.663 | B₄ | H | H | F | F | 4-Cl | H |
| W.664 | B₄ | H | H | CH₃ | CH₃ | 4-Cl | H |
| W.665 | B₄ | F | H | CH₃ | CH₃ | 4-Cl | H |
| W.666 | B₄ | H | CH₃ | CH₃ | CH₃ | 4-Cl | H |
| W.667 | B₄ | CH₃ | CH₃ | CH₃ | CH₃ | 4-Cl | H |
| W.668 | B₄ | F | CH₃ | CH₃ | CH₃ | 4-Cl | H |
| W.669 | B₄ | H | H | H | H | 6-Cl | H |
| W.670 | B₄ | CH₃ | H | H | H | 6-Cl | H |
| W.671 | B₄ | CH₂CH₃ | H | H | H | 6-Cl | H |
| W.672 | B₄ | F | H | H | H | 6-Cl | H |
| W.673 | B₄ | CN | H | H | H | 6-Cl | H |
| W.674 | B₄ | H | CH₃ | H | H | 6-Cl | H |
| W.675 | B₄ | CH₃ | CH₃ | H | H | 6-Cl | H |
| W.676 | B₄ | CH₂CH₃ | CH₃ | H | H | 6-Cl | H |
| W.677 | B₄ | F | CH₃ | H | H | 6-Cl | H |
| W.678 | B₄ | CN | CH₃ | H | H | 6-Cl | H |
| W.679 | B₄ | H | CH₂CH₃ | H | H | 6-Cl | H |
| W.680 | B₄ | CH₃ | CH₂CH₃ | H | H | 6-Cl | H |
| W.681 | B₄ | F | CH₂CH₃ | H | H | 6-Cl | H |
| W.682 | B₄ | CN | CH₂CH₃ | H | H | 6-Cl | H |
| W.683 | B₄ | H | H | F | H | 6-Cl | H |
| W.684 | B₄ | CH₃ | H | F | H | 6-Cl | H |
| W.685 | B₄ | F | H | F | H | 6-Cl | H |
| W.686 | B₄ | H | CH₃ | F | H | 6-Cl | H |
| W.687 | B₄ | CH₃ | CH₃ | F | H | 6-Cl | H |
| W.688 | B₄ | F | CH₃ | F | H | 6-Cl | H |
| W.689 | B₄ | H | H | F | F | 6-Cl | H |
| W.690 | B₄ | H | H | CH₃ | CH₃ | 6-Cl | H |
| W.691 | B₄ | F | H | CH₃ | CH₃ | 6-Cl | H |
| W.692 | B₄ | H | CH₃ | CH₃ | CH₃ | 6-Cl | H |
| W.693 | B₄ | CH₃ | CH₃ | CH₃ | CH₃ | 6-Cl | H |
| W.694 | B₄ | F | CH₃ | CH₃ | CH₃ | 6-Cl | H |
| W.695 | B₄ | H | H | H | H | 7-Cl | H |
| W.696 | B₄ | CH₃ | H | H | H | 7-Cl | H |
| W.697 | B₄ | CH₂CH₃ | H | H | H | 7-Cl | H |
| W.698 | B₄ | F | H | H | H | 7-Cl | H |
| W.699 | B₄ | CN | H | H | H | 7-Cl | H |
| W.700 | B₄ | H | CH₃ | H | H | 7-Cl | H |
| W.701 | B₄ | CH₃ | CH₃ | H | H | 7-Cl | H |
| W.702 | B₄ | CH₂CH₃ | CH₃ | H | H | 7-Cl | H |
| W.703 | B₄ | F | CH₃ | H | H | 7-Cl | H |
| W.704 | B₄ | CN | CH₃ | H | H | 7-Cl | H |
| W.705 | B₄ | H | CH₂CH₃ | H | H | 7-Cl | H |
| W.706 | B₄ | CH₃ | CH₂CH₃ | H | H | 7-Cl | H |
| W.707 | B₄ | F | CH₂CH₃ | H | H | 7-Cl | H |
| W.708 | B₄ | CN | CH₂CH₃ | H | H | 7-Cl | H |
| W.709 | B₄ | H | H | F | H | 7-Cl | H |
| W.710 | B₄ | CH₃ | H | F | H | 7-Cl | H |
| W.711 | B₄ | F | H | F | H | 7-Cl | H |
| W.712 | B₄ | H | CH₃ | F | H | 7-Cl | H |
| W.713 | B₄ | CH₃ | CH₃ | F | H | 7-Cl | H |
| W.714 | B₄ | F | CH₃ | F | H | 7-Cl | H |
| W.715 | B₄ | H | H | F | F | 7-Cl | H |
| W.716 | B₄ | H | H | CH₃ | CH₃ | 7-Cl | H |

TABLE W-continued

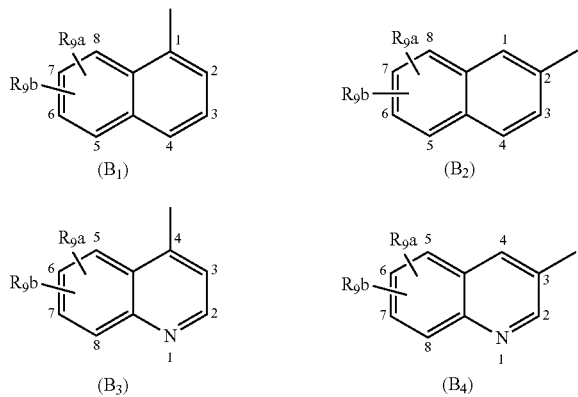

| Compound No. | B | $R_1$ | $R_2$ | $R_3$ | $R_4$ | $R_{9a}$ | $R_{9b}$ |
|---|---|---|---|---|---|---|---|
| W.717 | $B_4$ | F | H | $CH_3$ | $CH_3$ | 7-Cl | H |
| W.718 | $B_4$ | H | $CH_3$ | $CH_3$ | $CH_3$ | 7-Cl | H |
| W.719 | $B_4$ | $CH_3$ | $CH_3$ | $CH_3$ | $CH_3$ | 7-Cl | H |
| W.720 | $B_4$ | F | $CH_3$ | $CH_3$ | $CH_3$ | 7-Cl | H |
| W.721 | $B_4$ | H | H | H | H | 8-Cl | H |
| W.722 | $B_4$ | $CH_3$ | H | H | H | 8-Cl | H |
| W.723 | $B_4$ | $CH_2CH_3$ | H | H | H | 8-Cl | H |
| W.724 | $B_4$ | F | H | H | H | 8-Cl | H |
| W.725 | $B_4$ | CN | H | H | H | 8-Cl | H |
| W.726 | $B_4$ | H | $CH_3$ | H | H | 8-Cl | H |
| W.727 | $B_4$ | $CH_3$ | $CH_3$ | H | H | 8-Cl | H |
| W.728 | $B_4$ | $CH_2CH_3$ | $CH_3$ | H | H | 8-Cl | H |
| W.729 | $B_4$ | F | $CH_3$ | H | H | 8-Cl | H |
| W.730 | $B_4$ | CN | $CH_3$ | H | H | 8-Cl | H |
| W.731 | $B_4$ | H | $CH_2CH_3$ | H | H | 8-Cl | H |
| W.732 | $B_4$ | $CH_3$ | $CH_2CH_3$ | H | H | 8-Cl | H |
| W.733 | $B_4$ | F | $CH_2CH_3$ | H | H | 8-Cl | H |
| W.734 | $B_4$ | CN | $CH_2CH_3$ | H | H | 8-Cl | H |
| W.735 | $B_4$ | H | H | F | H | 8-Cl | H |
| W.736 | $B_4$ | $CH_3$ | H | F | H | 8-Cl | H |
| W.737 | $B_4$ | F | H | F | H | 8-Cl | H |
| W.738 | $B_4$ | H | $CH_3$ | F | H | 8-Cl | H |
| W.739 | $B_4$ | $CH_3$ | $CH_3$ | F | H | 8-Cl | H |
| W.740 | $B_4$ | F | $CH_3$ | F | H | 8-Cl | H |
| W.741 | $B_4$ | H | H | F | F | 8-Cl | H |
| W.742 | $B_4$ | H | H | $CH_3$ | $CH_3$ | 8-Cl | H |
| W.743 | $B_4$ | F | H | $CH_3$ | $CH_3$ | 8-Cl | H |
| W.744 | $B_4$ | H | $CH_3$ | $CH_3$ | $CH_3$ | 8-Cl | H |
| W.745 | $B_4$ | $CH_3$ | $CH_3$ | $CH_3$ | $CH_3$ | 8-Cl | H |
| W.746 | $B_4$ | F | $CH_3$ | $CH_3$ | $CH_3$ | 8-Cl | H |
| W.747 | $B_4$ | H | H | H | H | 2-Cl | 5-Cl |
| W.748 | $B_4$ | $CH_3$ | H | H | H | 2-Cl | 5-Cl |
| W.749 | $B_4$ | $CH_2CH_3$ | H | H | H | 2-Cl | 5-Cl |
| W.750 | $B_4$ | F | H | H | H | 2-Cl | 5-Cl |
| W.751 | $B_4$ | CN | H | H | H | 2-Cl | 5-Cl |
| W.752 | $B_4$ | H | $CH_3$ | H | H | 2-Cl | 5-Cl |
| W.753 | $B_4$ | $CH_3$ | $CH_3$ | H | H | 2-Cl | 5-Cl |
| W.754 | $B_4$ | $CH_2CH_3$ | $CH_3$ | H | H | 2-Cl | 5-Cl |
| W.755 | $B_4$ | F | $CH_3$ | H | H | 2-Cl | 5-Cl |
| W.756 | $B_4$ | CN | $CH_3$ | H | H | 2-Cl | 5-Cl |
| W.757 | $B_4$ | H | $CH_2CH_3$ | H | H | 2-Cl | 5-Cl |
| W.758 | $B_4$ | $CH_3$ | $CH_2CH_3$ | H | H | 2-Cl | 5-Cl |
| W.759 | $B_4$ | F | $CH_2CH_3$ | H | H | 2-Cl | 5-Cl |
| W.760 | $B_4$ | CN | $CH_2CH_3$ | H | H | 2-Cl | 5-Cl |
| W.761 | $B_4$ | H | H | F | H | 2-Cl | 5-Cl |
| W.762 | $B_4$ | $CH_3$ | H | F | H | 2-Cl | 5-Cl |
| W.763 | $B_4$ | F | H | F | H | 2-Cl | 5-Cl |
| W.764 | $B_4$ | H | $CH_3$ | F | H | 2-Cl | 5-Cl |
| W.765 | $B_4$ | $CH_3$ | $CH_3$ | F | H | 2-Cl | 5-Cl |
| W.766 | $B_4$ | F | $CH_3$ | F | H | 2-Cl | 5-Cl |
| W.767 | $B_4$ | H | H | F | F | 2-Cl | 5-Cl |
| W.768 | $B_4$ | H | H | $CH_3$ | $CH_3$ | 2-Cl | 5-Cl |
| W.769 | $B_4$ | F | H | $CH_3$ | $CH_3$ | 2-Cl | 5-Cl |
| W.770 | $B_4$ | H | $CH_3$ | $CH_3$ | $CH_3$ | 2-Cl | 5-Cl |
| W.771 | $B_4$ | $CH_3$ | $CH_3$ | $CH_3$ | $CH_3$ | 2-Cl | 5-Cl |
| W.772 | $B_4$ | F | $CH_3$ | $CH_3$ | $CH_3$ | 2-Cl | 6-Cl |
| W.773 | $B_4$ | H | H | H | H | 2-Cl | 6-Cl |

TABLE W-continued

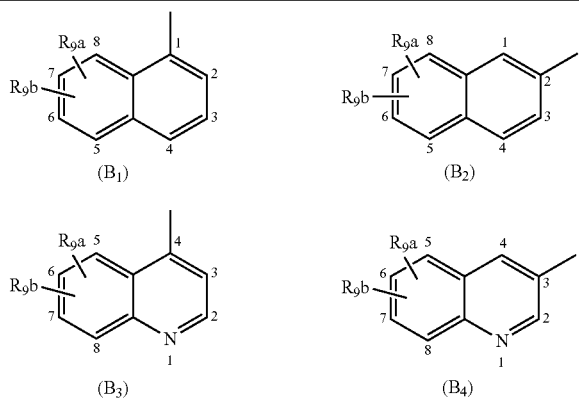

| Compound No. | B | $R_1$ | $R_2$ | $R_3$ | $R_4$ | $R_{9a}$ | $R_{9b}$ |
|---|---|---|---|---|---|---|---|
| W.774 | $B_4$ | $CH_3$ | H | H | H | 2-Cl | 6-Cl |
| W.775 | $B_4$ | $CH_2CH_3$ | H | H | H | 2-Cl | 6-Cl |
| W.776 | $B_4$ | F | H | H | H | 2-Cl | 6-Cl |
| W.777 | $B_4$ | CN | H | H | H | 2-Cl | 6-Cl |
| W.778 | $B_4$ | H | $CH_3$ | H | H | 2-Cl | 6-Cl |
| W.779 | $B_4$ | $CH_3$ | $CH_3$ | H | H | 2-Cl | 6-Cl |
| W.780 | $B_4$ | $CH_2CH_3$ | $CH_3$ | H | H | 2-Cl | 6-Cl |
| W.781 | $B_4$ | F | $CH_3$ | H | H | 2-Cl | 6-Cl |
| W.782 | $B_4$ | CN | $CH_3$ | H | H | 2-Cl | 6-Cl |
| W.783 | $B_4$ | H | $CH_2CH_3$ | H | H | 2-Cl | 6-Cl |
| W.784 | $B_4$ | $CH_3$ | $CH_2CH_3$ | H | H | 2-Cl | 6-Cl |
| W.785 | $B_4$ | F | $CH_2CH_3$ | H | H | 2-Cl | 6-Cl |
| W.786 | $B_4$ | CN | $CH_2CH_3$ | H | H | 2-Cl | 6-Cl |
| W.787 | $B_4$ | H | H | F | H | 2-Cl | 6-Cl |
| W.788 | $B_4$ | $CH_3$ | H | F | H | 2-Cl | 6-Cl |
| W.789 | $B_4$ | F | H | F | H | 2-Cl | 6-Cl |
| W.790 | $B_4$ | H | $CH_3$ | F | H | 2-Cl | 6-Cl |
| W.791 | $B_4$ | $CH_3$ | $CH_3$ | F | H | 2-Cl | 6-Cl |
| W.792 | $B_4$ | F | $CH_3$ | F | H | 2-Cl | 6-Cl |
| W.793 | $B_4$ | H | H | F | F | 2-Cl | 6-Cl |
| W.794 | $B_4$ | H | H | $CH_3$ | $CH_3$ | 2-Cl | 6-Cl |
| W.795 | $B_4$ | F | H | $CH_3$ | $CH_3$ | 2-Cl | 6-Cl |
| W.796 | $B_4$ | H | $CH_3$ | $CH_3$ | $CH_3$ | 2-Cl | 6-Cl |
| W.797 | $B_4$ | $CH_3$ | $CH_3$ | $CH_3$ | $CH_3$ | 2-Cl | 6-Cl |
| W.798 | $B_4$ | F | $CH_3$ | $CH_3$ | $CH_3$ | 2-Cl | 6-Cl |
| W.799 | $B_4$ | H | H | H | H | 2-Cl | 7-Cl |
| W.800 | $B_4$ | $CH_3$ | H | H | H | 2-Cl | 7-Cl |
| W.801 | $B_4$ | $CH_2CH_3$ | H | H | H | 2-Cl | 7-Cl |
| W.802 | $B_4$ | F | H | H | H | 2-Cl | 7-Cl |
| W.803 | $B_4$ | CN | H | H | H | 2-Cl | 7-Cl |
| W.804 | $B_4$ | H | $CH_3$ | H | H | 2-Cl | 7-Cl |
| W.805 | $B_4$ | $CH_3$ | $CH_3$ | H | H | 2-Cl | 7-Cl |
| W.806 | $B_4$ | $CH_2CH_3$ | $CH_3$ | H | H | 2-Cl | 7-Cl |
| W.807 | $B_4$ | F | $CH_3$ | H | H | 2-Cl | 7-Cl |
| W.808 | $B_4$ | CN | $CH_3$ | H | H | 2-Cl | 7-Cl |
| W.809 | $B_4$ | H | $CH_2CH_3$ | H | H | 2-Cl | 7-Cl |
| W.810 | $B_4$ | $CH_3$ | $CH_2CH_3$ | H | H | 2-Cl | 7-Cl |
| W.811 | $B_4$ | F | $CH_2CH_3$ | H | H | 2-Cl | 7-Cl |
| W.812 | $B_4$ | CN | $CH_2CH_3$ | H | H | 2-Cl | 7-Cl |
| W.813 | $B_4$ | H | H | F | H | 2-Cl | 7-Cl |
| W.814 | $B_4$ | $CH_3$ | H | F | H | 2-Cl | 7-Cl |
| W.815 | $B_4$ | F | H | F | H | 2-Cl | 7-Cl |
| W.816 | $B_4$ | H | $CH_3$ | F | H | 2-Cl | 7-Cl |
| W.817 | $B_4$ | $CH_3$ | $CH_3$ | F | H | 2-Cl | 7-Cl |
| W.818 | $B_4$ | F | $CH_3$ | F | H | 2-Cl | 7-Cl |
| W.819 | $B_4$ | H | H | F | F | 2-Cl | 7-Cl |
| W.820 | $B_4$ | H | H | $CH_3$ | $CH_3$ | 2-Cl | 7-Cl |
| W.821 | $B_4$ | F | H | $CH_3$ | $CH_3$ | 2-Cl | 7-Cl |
| W.822 | $B_4$ | H | $CH_3$ | $CH_3$ | $CH_3$ | 2-Cl | 7-Cl |
| W.823 | $B_4$ | $CH_3$ | $CH_3$ | $CH_3$ | $CH_3$ | 2-Cl | 7-Cl |
| W.824 | $B_4$ | F | $CH_3$ | $CH_3$ | $CH_3$ | 2-Cl | 7-Cl |
| W.825 | $B_4$ | H | H | H | H | 2-Cl | 8-Cl |
| W.826 | $B_4$ | $CH_3$ | H | H | H | 2-Cl | 8-Cl |
| W.827 | $B_4$ | $CH_2CH_3$ | H | H | H | 2-Cl | 8-Cl |
| W.828 | $B_4$ | F | H | H | H | 2-Cl | 8-Cl |
| W.829 | $B_4$ | CN | H | H | H | 2-Cl | 8-Cl |
| W.830 | $B_4$ | H | $CH_3$ | H | H | 2-Cl | 8-Cl |

TABLE W-continued

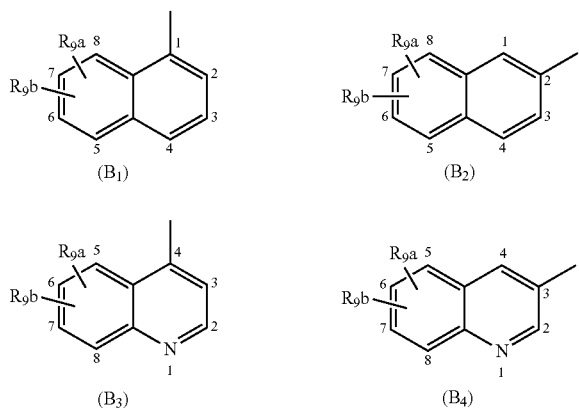

| Compound No. | B | $R_1$ | $R_2$ | $R_3$ | $R_4$ | $R_{9a}$ | $R_{9b}$ |
|---|---|---|---|---|---|---|---|
| W.831 | $B_4$ | $CH_3$ | $CH_3$ | H | H | 2-Cl | 8-Cl |
| W.832 | $B_4$ | $CH_2CH_3$ | $CH_3$ | H | H | 2-Cl | 8-Cl |
| W.833 | $B_4$ | F | $CH_3$ | H | H | 2-Cl | 8-Cl |
| W.834 | $B_4$ | CN | $CH_3$ | H | H | 2-Cl | 8-Cl |
| W.835 | $B_4$ | H | $CH_2CH_3$ | H | H | 2-Cl | 8-Cl |
| W.836 | $B_4$ | $CH_3$ | $CH_2CH_3$ | H | H | 2-Cl | 8-Cl |
| W.837 | $B_4$ | F | $CH_2CH_3$ | H | H | 2-Cl | 8-Cl |
| W.838 | $B_4$ | CN | $CH_2CH_3$ | H | H | 2-Cl | 8-Cl |
| W.839 | $B_4$ | H | H | F | H | 2-Cl | 8-Cl |
| W.840 | $B_4$ | $CH_3$ | H | F | H | 2-Cl | 8-Cl |
| W.841 | $B_4$ | F | H | F | H | 2-Cl | 8-Cl |
| W.842 | $B_4$ | H | $CH_3$ | F | H | 2-Cl | 8-Cl |
| 243 | $B_4$ | $CH_3$ | $CH_3$ | F | H | 2-Cl | 8-Cl |
| W.844 | $B_4$ | F | $CH_3$ | F | H | 2-Cl | 8-Cl |
| W.845 | $B_4$ | H | H | F | F | 2-Cl | 8-Cl |
| W.846 | $B_4$ | H | H | $CH_3$ | $CH_3$ | 2-Cl | 8-Cl |
| W.847 | $B_4$ | F | H | $CH_3$ | $CH_3$ | 2-Cl | 8-Cl |
| W.848 | $B_4$ | H | $CH_3$ | $CH_3$ | $CH_3$ | 2-Cl | 8-Cl |
| W.849 | $B_4$ | $CH_3$ | $CH_3$ | $CH_3$ | $CH_3$ | 2-Cl | 8-Cl |
| W.850 | $B_4$ | F | $CH_3$ | $CH_3$ | $CH_3$ | 2-Cl | 8-Cl |
| W.851 | $B_4$ | H | H | H | H | 6-p-Cl-phenyl | 2-Cl |
| W.852 | $B_4$ | $CH_3$ | H | H | H | 6-p-Cl-phenyl | 2-Cl |
| W.853 | $B_4$ | $CH_2CH_3$ | H | H | H | 6-p-Cl-phenyl | 2-Cl |
| W.254 | $B_4$ | F | H | H | H | 6-p-Cl-phenyl | 2-Cl |
| W.855 | $B_4$ | CN | H | H | H | 6-p-Cl-phenyl | 2-Cl |
| W.856 | $B_4$ | H | $CH_3$ | H | H | 6-p-Cl-phenyl | 2-Cl |
| W.857 | $B_4$ | $CH_3$ | $CH_3$ | H | H | 6-p-Cl-phenyl | 2-Cl |
| W.858 | $B_4$ | $CH_2CH_3$ | $CH_3$ | H | H | 6-p-Cl-phenyl | 2-Cl |
| W.859 | $B_4$ | F | $CH_3$ | H | H | 6-p-Cl-phenyl | 2-Cl |
| W.860 | $B_4$ | CN | $CH_3$ | H | H | 6-p-Cl-phenyl | 2-Cl |
| W.861 | $B_4$ | H | $CH_2CH_3$ | H | H | 6-p-Cl-phenyl | 2-Cl |
| W.862 | $B_4$ | $CH_3$ | $CH_2CH_3$ | H | H | 6-p-Cl-phenyl | 2-Cl |
| W.863 | $B_4$ | F | $CH_2CH_3$ | H | H | 6-p-Cl-phenyl | 2-Cl |
| W.864 | $B_4$ | CN | $CH_2CH_3$ | H | H | 6-p-Cl-phenyl | 2-Cl |
| W.865 | $B_4$ | H | H | F | H | 6-p-Cl-phenyl | 2-Cl |
| W.866 | $B_4$ | $CH_3$ | H | F | H | 6-p-Cl-phenyl | 2-Cl |
| W.867 | $B_4$ | F | H | F | H | 6-p-Cl-phenyl | 2-Cl |
| W.868 | $B_4$ | H | $CH_3$ | F | H | 6-p-Cl-phenyl | 2-Cl |
| W.869 | $B_4$ | $CH_3$ | $CH_3$ | F | H | 6-p-Cl-phenyl | 2-Cl |
| W.870 | $B_4$ | F | $CH_3$ | F | H | 6-p-Cl-phenyl | 2-Cl |
| W.871 | $B_4$ | H | H | F | F | 6-p-Cl-phenyl | 2-Cl |
| W.872 | $B_4$ | H | H | $CH_3$ | $CH_3$ | 6-p-Cl-phenyl | 2-Cl |

In Table W the group B stands for the group $B_1$, $B_2$, $B_3$ or $B_4$:

Table 9 provides 872 compounds of formula (IB), wherein A is

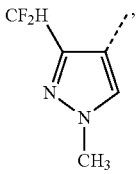

wherein the broken lines indicate the point of attachment of the group A to the amide group, and B, $R_1$, $R_2$, $R_3$, $R_4$, $R_{9a}$ and $R_{9b}$ are as defined in Table W. For example, compound 9.001 has the following structure:

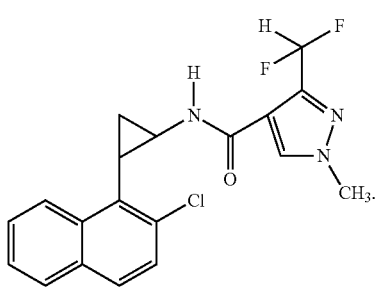

(9.001)

Table 10 provides 872 compounds of formula (IB) wherein A is

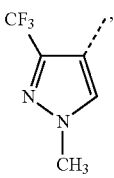

wherein the broken lines indicate the point of attachment of the group A to the amide group, and B, $R_1$, $R_2$, $R_3$, $R_4$, $R_{9a}$ and $R_{9b}$ are as defined in Table W.

Table 11 provides 872 compounds of formula (IB) wherein A is

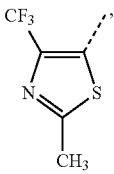

wherein the broken lines indicate the point of attachment of the group A to the amide group, and B, $R_1$, $R_2$, $R_3$, $R_4$, $R_{9a}$ and $R_{9b}$ are as defined in Table W.

Table 12 provides 872 compounds of formula (IB) wherein A is

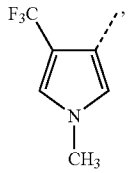

wherein the broken lines indicate the point of attachment of the group A to the amide group, and B, $R_1$, $R_2$, $R_3$, $R_4$, $R_{9a}$ and $R_{9b}$ are as defined in Table W.

Table 13 provides 872 compounds of formula (IB) wherein A is

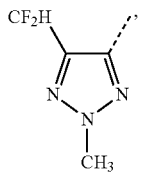

wherein the broken lines indicate the point of attachment of the group A to the amide group, and B, $R_1$, $R_2$, $R_3$, $R_4$, $R_{9a}$ and $R_{9b}$ are as defined in Table W.

Table 14 provides 872 compounds of formula (IB) wherein A is

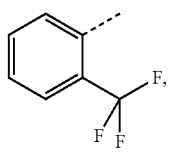

wherein the broken lines indicate the point of attachment of the group A to the amide group, and B, $R_1$, $R_2$, $R_3$, $R_4$, $R_{9a}$ and $R_{9b}$ are as defined in Table W.

Table 15 provides 872 compounds of formula (IB) wherein A is

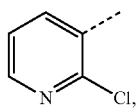

wherein the broken lines indicate the point of attachment of the group A to the amide group, and B, $R_1$, $R_2$, $R_3$, $R_4$, $R_{9a}$ and $R_{9b}$ are as defined in Table W.

Table 16 provides 872 compounds of formula (IB) wherein A is

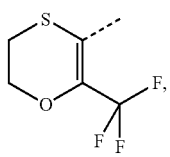

wherein the broken lines indicate the point of attachment of the group A to the amide group, and B, $R_1$, $R_2$, $R_3$, $R_4$, $R_{9a}$ and $R_{9b}$ are as defined in Table W.

Table 17: Compounds of Formula IIA

Illustrative of the compounds of formula (IIA) are the compounds listed in Table 17 below. Characterising data for these compounds are given in Table 18.

TABLE 17

(IIA)

| Cpd No. | R₁ | R₂ | R₃ | R₄ | R₉ₐ | R₉ᵦ | R₉c |
|---|---|---|---|---|---|---|---|
| Z1.001 | H | H | H | H | 4-Cl | H | H |
| Z1.002 | CH₃ | H | H | H | 4-Cl | H | H |
| Z1.003 | CH₂CH₃ | H | H | H | 4-Cl | H | H |
| Z1.004 | F | H | H | H | 4-Cl | H | H |
| Z1.005 | CN | H | H | H | 4-Cl | H | H |
| Z1.006 | H | CH₃ | H | H | 4-Cl | H | H |
| Z1.007 | CH₃ | CH₃ | H | H | 4-Cl | H | H |
| Z1.008 | CH₂CH₃ | CH₃ | H | H | 4-Cl | H | H |
| Z1.009 | F | CH₃ | H | H | 4-Cl | H | H |
| Z1.010 | CN | CH₃ | H | H | 4-Cl | H | H |
| Z1.011 | H | CH₂CH₃ | H | H | 4-Cl | H | H |
| Z1.012 | CH₃ | CH₂CH₃ | H | H | 4-Cl | H | H |
| Z1.013 | F | CH₂CH₃ | H | H | 4-Cl | H | H |
| Z1.014 | CN | CH₂CH₃ | H | H | 4-Cl | H | H |
| Z1.015 | H | H | F | H | 4-Cl | H | H |
| Z1.016 | CH₃ | H | F | H | 4-Cl | H | H |
| Z1.017 | F | H | F | H | 4-Cl | H | H |
| Z1.018 | H | CH₃ | F | H | 4-Cl | H | H |
| Z1.019 | CH₃ | CH₃ | F | H | 4-Cl | H | H |
| Z1.020 | F | CH₃ | F | H | 4-Cl | H | H |
| Z1.021 | H | H | F | F | 4-Cl | H | H |
| Z1.022 | CH₃ | H | F | F | 4-Cl | H | H |
| Z1.023 | F | H | F | F | 4-Cl | H | H |
| Z1.024 | H | CH₃ | F | F | 4-Cl | H | H |
| Z1.025 | CH₃ | CH₃ | F | F | 4-Cl | H | H |
| Z1.026 | F | CH₃ | F | F | 4-Cl | H | H |
| Z1.027 | H | H | H | H | 4-CF₃ | H | H |
| Z1.028 | CH₃ | H | H | H | 4-CF₃ | H | H |
| Z1.029 | CH₂CH₃ | H | H | H | 4-CF₃ | H | H |
| Z1.030 | F | H | H | H | 4-CF₃ | H | H |
| Z1.031 | CN | H | H | H | 4-CF₃ | H | H |
| Z1.032 | H | CH₃ | H | H | 4-CF₃ | H | H |
| Z1.033 | CH₃ | CH₃ | H | H | 4-CF₃ | H | H |
| Z1.034 | CH₂CH₃ | CH₃ | H | H | 4-CF₃ | H | H |
| Z1.035 | F | CH₃ | H | H | 4-CF₃ | H | H |
| Z1.036 | CN | CH₃ | H | H | 4-CF₃ | H | H |
| Z1.037 | H | CH₂CH₃ | H | H | 4-CF₃ | H | H |
| Z1.038 | CH₃ | CH₂CH₃ | H | H | 4-CF₃ | H | H |
| Z1.039 | F | CH₂CH₃ | H | H | 4-CF₃ | H | H |
| Z1.040 | CN | CH₂CH₃ | H | H | 4-CF₃ | H | H |
| Z1.041 | H | H | F | H | 4-CF₃ | H | H |
| Z1.042 | CH₃ | H | F | H | 4-CF₃ | H | H |
| Z1.043 | F | H | F | H | 4-CF₃ | H | H |
| Z1.044 | H | CH₃ | F | H | 4-CF₃ | H | H |
| Z1.045 | CH₃ | CH₃ | F | H | 4-CF₃ | H | H |
| Z1.046 | F | CH₃ | F | H | 4-CF₃ | H | H |
| Z1.047 | H | H | F | F | 4-CF₃ | H | H |
| Z1.048 | CH₃ | H | F | F | 4-CF₃ | H | H |
| Z1.049 | F | H | F | F | 4-CF₃ | H | H |
| Z1.050 | H | CH₃ | F | F | 4-CF₃ | H | H |
| Z1.051 | CH₃ | CH₃ | F | F | 4-CF₃ | H | H |
| Z1.052 | F | CH₃ | F | F | 4-CF₃ | H | H |
| Z1.053 | H | H | H | H | 4-OCF₃ | H | H |
| Z1.054 | CH₃ | H | H | H | 4-OCF₃ | H | H |
| Z1.055 | CH₂CH₃ | H | H | H | 4-OCF₃ | H | H |
| Z1.056 | F | H | H | H | 4-OCF₃ | H | H |
| Z1.057 | CN | H | H | H | 4-OCF₃ | H | H |
| Z1.058 | H | CH₃ | H | H | 4-OCF₃ | H | H |
| Z1.059 | CH₃ | CH₃ | H | H | 4-OCF₃ | H | H |
| Z1.060 | CH₂CH₃ | CH₃ | H | H | 4-OCF₃ | H | H |
| Z1.061 | F | CH₃ | H | H | 4-OCF₃ | H | H |
| Z1.062 | CN | CH₃ | H | H | 4-OCF₃ | H | H |
| Z1.063 | H | CH₂CH₃ | H | H | 4-OCF₃ | H | H |
| Z1.064 | CH₃ | CH₂CH₃ | H | H | 4-OCF₃ | H | H |
| Z1.065 | F | CH₂CH₃ | H | H | 4-OCF₃ | H | H |
| Z1.066 | CN | CH₂CH₃ | H | H | 4-OCF₃ | H | H |
| Z1.067 | H | H | F | H | 4-OCF₃ | H | H |

TABLE 17-continued (IIA)

| Cpd No. | R₁ | R₂ | R₃ | R₄ | R₉ₐ | R₉ᵦ | R₉c |
|---|---|---|---|---|---|---|---|
| Z1.068 | CH₃ | H | F | H | 4-OCF₃ | H | H |
| Z1.069 | F | H | F | H | 4-OCF₃ | H | H |
| Z1.070 | H | CH₃ | F | H | 4-OCF₃ | H | H |
| Z1.071 | CH₃ | CH₃ | F | H | 4-OCF₃ | H | H |
| Z1.072 | F | CH₃ | F | H | 4-OCF₃ | H | H |
| Z1.073 | H | H | F | F | 4-OCF₃ | H | H |
| Z1.074 | CH₃ | H | F | F | 4-OCF₃ | H | H |
| Z1.075 | F | H | F | F | 4-OCF₃ | H | H |
| Z1.076 | H | CH₃ | F | F | 4-OCF₃ | H | H |
| Z1.077 | CH₃ | CH₃ | F | F | 4-OCF₃ | H | H |
| Z1.078 | F | CH₃ | F | F | 4-OCF₃ | H | H |
| Z1.079 | H | H | H | H | 4-F | H | H |
| Z1.080 | F | H | H | H | 4-F | H | H |
| Z1.081 | H | CH₃ | H | H | 4-F | H | H |
| Z1.082 | F | CH₃ | H | H | 4-F | H | H |
| Z1.083 | H | CH₂CH₃ | H | H | 4-F | H | H |
| Z1.084 | H | H | F | H | 4-F | H | H |
| Z1.085 | F | H | F | H | 4-F | H | H |
| Z1.086 | H | CH₃ | F | H | 4-F | H | H |
| Z1.087 | F | CH₃ | F | H | 4-F | H | H |
| Z1.088 | H | H | F | F | 4-F | H | H |
| Z1.089 | F | H | F | F | 4-F | H | H |
| Z1.090 | F | CH₃ | F | F | 4-F | H | H |
| Z1.091 | H | H | H | H | 4-p-Cl-phenyl | H | H |
| Z1.092 | CH₃ | H | H | H | 4-p-Cl-phenyl | H | H |
| Z1.093 | CH₂CH₃ | H | H | H | 4-p-Cl-phenyl | H | H |
| Z1.094 | F | H | H | H | 4-p-Cl-phenyl | H | H |
| Z1.095 | CN | H | H | H | 4-p-Cl-phenyl | H | H |
| Z1.096 | H | CH₃ | H | H | 4-p-Cl-phenyl | H | H |
| Z1.097 | CH₃ | CH₃ | H | H | 4-p-Cl-phenyl | H | H |
| Z1.098 | CH₂CH₃ | CH₃ | H | H | 4-p-Cl-phenyl | H | H |
| Z1.099 | F | CH₃ | H | H | 4-p-Cl-phenyl | H | H |
| Z1.100 | CN | CH₃ | H | H | 4-p-Cl-phenyl | H | H |
| Z1.101 | H | CH₂CH₃ | H | H | 4-p-Cl-phenyl | H | H |
| Z1.102 | CH₃ | CH₂CH₃ | H | H | 4-p-Cl-phenyl | H | H |
| Z1.103 | F | CH₂CH₃ | H | H | 4-p-Cl-phenyl | H | H |
| Z1.104 | CN | CH₂CH₃ | H | H | 4-p-Cl-phenyl | H | H |
| Z1.105 | H | H | F | H | 4-p-Cl-phenyl | H | H |
| Z1.106 | CH₃ | H | F | H | 4-p-Cl-phenyl | H | H |
| Z1.107 | F | H | F | H | 4-p-Cl-phenyl | H | H |
| Z1.108 | H | CH₃ | F | H | 4-p-Cl-phenyl | H | H |
| Z1.109 | CH₃ | CH₃ | F | H | 4-p-Cl-phenyl | H | H |
| Z1.110 | F | CH₃ | F | H | 4-p-Cl-phenyl | H | H |
| Z1.111 | H | H | F | F | 4-p-Cl-phenyl | H | H |
| Z1.112 | CH₃ | H | F | F | 4-p-Cl-phenyl | H | H |
| Z1.113 | F | H | F | F | 4-p-Cl-phenyl | H | H |
| Z1.114 | H | CH₃ | F | F | 4-p-Cl-phenyl | H | H |
| Z1.115 | CH₃ | CH₃ | F | F | 4-p-Cl-phenyl | H | H |
| Z1.116 | F | CH₃ | F | F | 4-p-Cl-phenyl | H | H |
| Z1.117 | H | H | H | H | 4-C≡CC(CH₃)₃ | H | H |
| Z1.118 | CH₃ | H | H | H | 4-C≡CC(CH₃)₃ | H | H |
| Z1.119 | CH₂CH₃ | H | H | H | 4-C≡CC(CH₃)₃ | H | H |
| Z1.120 | F | H | H | H | 4-C≡CC(CH₃)₃ | H | H |
| Z1.121 | CN | H | H | H | 4-C≡CC(CH₃)₃ | H | H |
| Z1.122 | H | CH₃ | H | H | 4-C≡CC(CH₃)₃ | H | H |
| Z1.123 | CH₃ | CH₃ | H | H | 4-C≡CC(CH₃)₃ | H | H |
| Z1.124 | CH₂CH₃ | CH₃ | H | H | 4-C≡CC(CH₃)₃ | H | H |
| Z1.125 | F | CH₃ | H | H | 4-C≡CC(CH₃)₃ | H | H |
| Z1.126 | CN | CH₃ | H | H | 4-C≡CC(CH₃)₃ | H | H |
| Z1.127 | H | CH₂CH₃ | H | H | 4-C≡CC(CH₃)₃ | H | H |
| Z1.128 | CH₃ | CH₂CH₃ | H | H | 4-C≡CC(CH₃)₃ | H | H |
| Z1.129 | F | CH₂CH₃ | H | H | 4-C≡CC(CH₃)₃ | H | H |
| Z1.130 | CN | CH₂CH₃ | H | H | 4-C≡CC(CH₃)₃ | H | H |
| Z1.131 | H | H | F | H | 4-C≡CC(CH₃)₃ | H | H |
| Z1.132 | H | CH₃ | F | H | 4-C≡CC(CH₃)₃ | H | H |
| Z1.133 | CH₃ | CH₃ | F | H | 4-C≡CC(CH₃)₃ | H | H |
| Z1.134 | F | CH₃ | F | H | 4-C≡CC(CH₃)₃ | H | H |

TABLE 17-continued

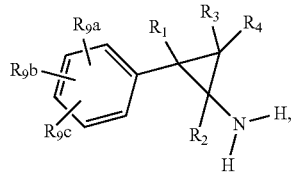

(IIA)

| Cpd No. | $R_1$ | $R_2$ | $R_3$ | $R_4$ | $R_{9a}$ | $R_{9b}$ | $R_{9c}$ |
|---|---|---|---|---|---|---|---|
| Z1.135 | H | H | F | F | 4-C≡CC(CH$_3$)$_3$ | H | H |
| Z1.136 | CH$_3$ | H | F | F | 4-C≡CC(CH$_3$)$_3$ | H | H |
| Z1.137 | F | H | F | F | 4-C≡CC(CH$_3$)$_3$ | H | H |
| Z1.138 | H | CH$_3$ | F | F | 4-C≡CC(CH$_3$)$_3$ | H | H |
| Z1.139 | CH$_3$ | CH$_3$ | F | F | 4-C≡CC(CH$_3$)$_3$ | H | H |
| Z1.140 | F | CH$_3$ | F | F | 4-C≡CC(CH$_3$)$_3$ | H | H |
| Z1.141 | H | H | H | H | 4-C≡CC(CH$_3$)$_3$ | H | H |
| Z1.142 | CH$_3$ | H | H | H | 4-C≡CC(CH$_3$)$_3$ | H | H |
| Z1.143 | H | H | H | H | 4-Cl | 2-Cl | H |
| Z1.144 | CH$_3$ | H | H | H | 4-Cl | 2-Cl | H |
| Z1.145 | CH$_2$CH$_3$ | H | H | H | 4-Cl | 2-Cl | H |
| Z1.146 | F | H | H | H | 4-Cl | 2-Cl | H |
| Z1.147 | CN | H | H | H | 4-Cl | 2-Cl | H |
| Z1.148 | H | CH$_3$ | H | H | 4-Cl | 2-Cl | H |
| Z1.149 | CH$_3$ | CH$_3$ | H | H | 4-Cl | 2-Cl | H |
| Z1.150 | CH$_2$CH$_3$ | CH$_3$ | H | H | 4-Cl | 2-Cl | H |
| Z1.151 | F | CH$_3$ | H | H | 4-Cl | 2-Cl | H |
| Z1.152 | CN | CH$_3$ | H | H | 4-Cl | 2-Cl | H |
| Z1.153 | H | CH$_2$CH$_3$ | H | H | 4-Cl | 2-Cl | H |
| Z1.154 | CH$_3$ | CH$_2$CH$_3$ | H | H | 4-Cl | 2-Cl | H |
| Z1.155 | F | CH$_2$CH$_3$ | H | H | 4-Cl | 2-Cl | H |
| Z1.156 | CN | CH$_2$CH$_3$ | H | H | 4-Cl | 2-Cl | H |
| Z1.157 | H | H | F | H | 4-Cl | 2-Cl | H |
| Z1.158 | CH$_3$ | H | F | H | 4-Cl | 2-Cl | H |
| Z1.159 | F | H | F | H | 4-Cl | 2-Cl | H |
| Z1.160 | H | CH$_3$ | F | H | 4-Cl | 2-Cl | H |
| Z1.161 | CH$_3$ | CH$_3$ | F | H | 4-Cl | 2-Cl | H |
| Z1.162 | F | CH$_3$ | F | H | 4-Cl | 2-Cl | H |
| Z1.163 | H | H | F | F | 4-Cl | 2-Cl | H |
| Z1.164 | CH$_3$ | H | F | F | 4-Cl | 2-Cl | H |
| Z1.165 | F | H | F | F | 4-Cl | 2-Cl | H |
| Z1.166 | H | CH$_3$ | F | F | 4-Cl | 2-Cl | H |
| Z1.167 | CH$_3$ | CH$_3$ | F | F | 4-Cl | 2-Cl | H |
| Z1.168 | F | CH$_3$ | F | F | 4-Cl | 2-Cl | H |
| Z1.169 | H | H | H | H | 4-F | 2-F | H |
| Z1.170 | CH$_3$ | H | H | H | 4-F | 2-F | H |
| Z1.171 | CH$_2$CH$_3$ | H | H | H | 4-F | 2-F | H |
| Z1.172 | F | H | H | H | 4-F | 2-F | H |
| Z1.173 | CN | H | H | H | 4-F | 2-F | H |
| Z1.174 | H | CH$_3$ | H | H | 4-F | 2-F | H |
| Z1.175 | CH$_3$ | CH$_3$ | H | H | 4-F | 2-F | H |
| Z1.176 | CH$_2$CH$_3$ | CH$_3$ | H | H | 4-F | 2-F | H |
| Z1.177 | F | CH$_3$ | H | H | 4-F | 2-F | H |
| Z1.178 | CN | CH$_3$ | H | H | 4-F | 2-F | H |
| Z1.179 | H | CH$_2$CH$_3$ | H | H | 4-F | 2-F | H |
| Z1.180 | CH$_3$ | CH$_2$CH$_3$ | H | H | 4-F | 2-F | H |
| Z1.181 | F | CH$_2$CH$_3$ | H | H | 4-F | 2-F | H |
| Z1.182 | CN | CH$_2$CH$_3$ | H | H | 4-F | 2-F | H |
| Z1.183 | H | H | F | H | 4-F | 2-F | H |
| Z1.184 | CH$_3$ | H | F | H | 4-F | 2-F | H |
| Z1.185 | F | H | F | H | 4-F | 2-F | H |
| Z1.186 | H | CH$_3$ | F | H | 4-F | 2-F | H |
| Z1.187 | CH$_3$ | CH$_3$ | F | H | 4-F | 2-F | H |
| Z1.188 | F | CH$_3$ | F | H | 4-F | 2-F | H |
| Z1.189 | H | H | F | F | 4-F | 2-F | H |
| Z1.190 | CH$_3$ | H | F | F | 4-F | 2-F | H |
| Z1.191 | F | H | F | F | 4-F | 2-F | H |
| Z1.192 | H | CH$_3$ | F | F | 4-F | 2-F | H |
| Z1.193 | CH$_3$ | CH$_3$ | F | F | 4-F | 2-F | H |
| Z1.194 | F | CH$_3$ | F | F | 4-F | 2-F | H |
| Z1.195 | H | H | H | H | 4-Cl | 2-F | H |
| Z1.196 | CH$_3$ | H | H | H | 4-Cl | 2-F | H |
| Z1.197 | CH$_2$CH$_3$ | H | H | H | 4-Cl | 2-F | H |
| Z1.198 | F | H | H | H | 4-Cl | 2-F | H |
| Z1.199 | CN | H | H | H | 4-Cl | 2-F | H |
| Z1.200 | H | CH$_3$ | H | H | 4-Cl | 2-F | H |
| Z1.201 | CH$_3$ | CH$_3$ | H | H | 4-Cl | 2-F | H |

TABLE 17-continued (IIA)

| Cpd No. | R₁ | R₂ | R₃ | R₄ | R₉ₐ | R₉ᵦ | R₉c |
|---|---|---|---|---|---|---|---|
| Z1.202 | CH₂CH₃ | CH₃ | H | H | 4-Cl | 2-F | H |
| Z1.203 | F | CH₃ | H | H | 4-Cl | 2-F | H |
| Z1.204 | CN | CH₃ | H | H | 4-Cl | 2-F | H |
| Z1.205 | H | CH₂CH₃ | H | H | 4-Cl | 2-F | H |
| Z1.206 | CH₃ | CH₂CH₃ | H | H | 4-Cl | 2-F | H |
| Z1.207 | F | CH₂CH₃ | H | H | 4-Cl | 2-F | H |
| Z1.208 | CN | CH₂CH₃ | H | H | 4-Cl | 2-F | H |
| Z1.209 | H | H | F | H | 4-Cl | 2-F | H |
| Z1.210 | CH₃ | H | F | H | 4-Cl | 2-F | H |
| Z1.211 | F | H | F | H | 4-Cl | 2-F | H |
| Z1.212 | H | CH₃ | F | H | 4-Cl | 2-F | H |
| Z1.213 | CH₃ | CH₃ | F | H | 4-Cl | 2-F | H |
| Z1.214 | F | CH₃ | F | H | 4-Cl | 2-F | H |
| Z1.215 | H | H | F | F | 4-Cl | 2-F | H |
| Z1.216 | CH₃ | H | F | F | 4-Cl | 2-F | H |
| Z1.217 | F | H | F | F | 4-Cl | 2-F | H |
| Z1.218 | H | CH₃ | F | F | 4-Cl | 2-F | H |
| Z1.219 | CH₃ | CH₃ | F | F | 4-Cl | 2-F | H |
| Z1.220 | F | CH₃ | F | F | 4-Cl | 2-F | H |
| Z1.221 | H | H | H | H | 4-F | 2-Cl | H |
| Z1.222 | H | H | H | H | 2-Cl | H | H |
| Z1.223 | CH₂CH₃ | H | H | H | 4-F | 2-Cl | H |
| Z1.224 | F | H | H | H | 4-F | 2-Cl | H |
| Z1.225 | CN | H | H | H | 4-F | 2-Cl | H |
| Z1.226 | H | CH₃ | H | H | 4-F | 2-Cl | H |
| Z1.227 | CH₃ | CH₃ | H | H | 4-F | 2-Cl | H |
| Z1.228 | CH₂CH₃ | CH₃ | H | H | 4-F | 2-Cl | H |
| Z1.229 | F | CH₃ | H | H | 4-F | 2-Cl | H |
| Z1.230 | CN | CH₃ | H | H | 4-F | 2-Cl | H |
| Z1.231 | H | CH₂CH₃ | H | H | 4-F | 2-Cl | H |
| Z1.232 | CH₃ | CH₂CH₃ | H | H | 4-F | 2-Cl | H |
| Z1.233 | F | CH₂CH₃ | H | H | 4-F | 2-Cl | H |
| Z1.234 | CN | CH₂CH₃ | H | H | 4-F | 2-Cl | H |
| Z1.235 | H | H | F | H | 4-F | 2-Cl | H |
| Z1.236 | CH₃ | H | F | H | 4-F | 2-Cl | H |
| Z1.237 | F | H | F | H | 4-F | 2-Cl | H |
| Z1.238 | H | CH₃ | F | H | 4-F | 2-Cl | H |
| Z1.239 | CH₃ | CH₃ | F | H | 4-F | 2-Cl | H |
| Z1.240 | F | CH₃ | F | H | 4-F | 2-Cl | H |
| Z1.241 | H | H | F | F | 4-F | 2-Cl | H |
| Z1.242 | CH₃ | H | F | F | 4-F | 2-Cl | H |
| Z1.243 | F | H | F | F | 4-F | 2-Cl | H |
| Z1.244 | H | CH₃ | F | F | 4-F | 2-Cl | H |
| Z1.245 | CH₃ | CH₃ | F | F | 4-F | 2-Cl | H |
| Z1.246 | F | CH₃ | F | F | 4-F | 2-Cl | H |
| Z1.247 | H | H | H | H | 4-p-Cl-phenyl | 2-Cl | H |
| Z1.248 | F | H | H | H | 4-p-Cl-phenyl | 2-Cl | H |
| Z1.249 | H | CH₃ | H | H | 4-p-Cl-phenyl | 2-Cl | H |
| Z1.250 | F | CH₃ | H | H | 4-p-Cl-phenyl | 2-Cl | H |
| Z1.251 | H | H | F | H | 4-p-Cl-phenyl | 2-Cl | H |
| Z1.252 | F | H | F | H | 4-p-Cl-phenyl | 2-Cl | H |
| Z1.253 | H | CH₃ | F | H | 4-p-Cl-phenyl | 2-Cl | H |
| Z1.254 | F | CH₃ | F | H | 4-p-Cl-phenyl | 2-Cl | H |
| Z1.255 | H | H | F | F | 4-p-Cl-phenyl | 2-Cl | H |
| Z1.256 | H | CH₃ | F | F | 4-p-Cl-phenyl | 2-Cl | H |
| Z1.257 | H | H | H | H | 4-Br | 2-Cl | H |
| Z1.258 | H | H | H | H | 4-Br | 2-Cl | 6-Cl |
| Z1.259 | H | H | H | H | 4-Cl | 2-Cl | 6-Cl |
| Z1.260 | H | H | H | H | 4-p-CF₃-phenyl | 2-Cl | 6-Cl |
| Z1.261 | H | H | H | H | 4-p-CF₃-phenyl | 2-Cl | H |
| Z1.262 | H | H | H | H | 4-(3',4'-Cl₂)-phenyl | 2-Cl | H |
| Z1.263 | H | H | H | H | 4-(3',4'-Cl₂)-phenyl | 2-Cl | 6-Cl |
| Z1.264 | H | H | H | H | 4-p-Cl-phenyl | 2-Cl | 6-Cl |
| Z1.265 | H | H | H | H | 4-(CH₃) | 2-Cl | 6-(CH₃) |
| Z1.266 | H | H | H | H | 4-(CH₃) | 2-CH₃ | 6-(CH₃) |
| Z1.267 | H | H | H | H | 4-C≡CC(CH₃)₃ | 2-Cl | H |
| Z1.268 | H | H | H | H | 4-C≡CC(CH₃)₃ | 2-Cl | 6-Cl |

TABLE 17-continued (IIA)

| Cpd No. | R₁ | R₂ | R₃ | R₄ | R₉ₐ | R₉ᵦ | R₉꜀ |
|---|---|---|---|---|---|---|---|
| Z1.269 | H | H | H | H | 4-C≡CCH(CH₂)₂ | 2-Cl | H |
| Z1.270 | H | H | H | H | 4-C≡CCH(CH₂)₂ | 2-Cl | 6-Cl |
| Z1.271 | H | H | H | H | 4-CH=N—OCH₃ | 2-Cl | H |
| Z1.272 | H | H | H | H | 4-CH=N—OCH₃ | 2-Cl | 6-Cl |
| Z1.273 | H | H | H | H | 4-C(CH₃)=N—OCH₃ | 2-Cl | H |
| Z1.274 | H | H | H | H | 4-C(CH₃)=N—OCH₃ | 2-Cl | 6-Cl |

Table 18: Characterising Data

Table 18 shows selected melting point and selected NMR data for compounds of Tables 1 to 17. CDCl₃ was used as the solvent for NMR measurements, unless otherwise stated. If a mixture of solvents was present, this is indicated as, for example: CDCl₃/d₆-DMSO). No attempt is made to list all characterising data in all cases.

In Table 18 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point b.p.=boiling point.
S=singlet br=broad
d=doublet dd=doublet of doublets
t=triplet q=quartet
m=multiplet ppm=parts per million

| Compound No. | 1H-NMR data: ppm (multiplicity/number of Hs) | MS [M + H]⁺ | m.p. (° C.) |
|---|---|---|---|
| 1.001 (cis) | 1.06-1.17 (m, 1H, CHH), 1.44 (q, 1H, CHH), 2.32-2.38 (q, 1H, CHAr), 3.23-3.29 (m, 1H, CHN), 3.73 (s, 3H, NCH₃), 6.08 (s, 1H, NH), 6.48-6.75 (t, 1H, CHF₂), 7.14-7.17 (d, 2H, Ar-H), 7.20-7.23 (d, 2H, Ar-H), 7.70 (s, 1H, Pyrazol-H) | 326/328 | 127 |
| 1.004 cis/trans = 7:3 | Cis isomer: 1.50δ (m; 1H): 1.92δ (ddd; 1H): 3.62δ (m; 1H): 3.85δ (s; 3H): 6.05δ (br-s; 1H): 6.60δ (t; 1H) 7.30δ-7.40δ (m; 4H): 7.80δ (s; 1H).<br>Trans isomer: 1.57δ (m; 1H): 1.67δ (ddd; 1H): 3.32δ (m; 1H): 6.70δ (br-s; 1H): 6.85δ (t; 1H): 7.30δ-7.40δ (m; 4H): 7.95δ (s; 1H). | — | — |
| 1.079 (cis) | 1.05δ (m; 1H): 1.42δ (m; 1H): 2.37δ (m; 1H): 3.25δ (m; 1H): 3.85δ (s; 3H): 6.00δ (br s; 1H): 6.57δ (t; 1H): 6.97δ-7.22δ (m; 4H): 7.77δ (s; 1H) | 310 | — |
| 1.143 (cis) | 1.15δ (m; 1H): 1.55δ (m; 1H): 2.42δ (m; 1H): 3.37δ (m; 1H): 3.85δ (s; 3H): 5.90δ (br s; 1H): 6.50δ (t; 1H): 7.42δ-7.10δ (m; 3H): 7.80δ (s; 1H) | 358/360/362 | — |
| 1.222 (cis) | 1.17δ (m; 1H): 1.50δ (m; 1H): 2.47δ (m; 1H): 3.37δ (m; 1H): 3.85δ (s; 3H): 5.90δ (br s; 1H): 6.45δ (t; 1H): 7.15δ-7.40δ (m; 4H): 7.77δ (s; 1H) | 326/328 | — |
| 2.079 (cis) | 1.05δ (m; 1H): 1.42δ (m; 1H): 2.40δ (m; 1H): 3.27δ (m; 1H): 3.90δ (s; 3H): 5.65δ (br s; 1H): 6.97δ-7.22δ (m; 4H): 7.80δ (s; 1H) | 328 | — |
| 2.143 (cs) | 1.15δ (m; 1H): 1.55δ (m; 1H): 2.40δ (m; 1H): 3.35δ (m; 1H): 3.90δ (s; 3H): 5.65δ (br s; 1H): 7.10δ-7.45δ (m; 3H): 7.82δ (s; 1H) | 376/378/380 | — |
| 2.222 (cis) | 1.15δ (m; 1H): 1.55δ (m; 1H): 2.45δ (m; 1H): 3.35δ (m; 1H): 3.87δ (s; 3H): 5.65δ (br s; 1H): 7.10δ-7.45δ (m; 4H): 7.80δ (s; 1H) | 344/346 | — |
| 6.004 (cis) | 1.60δ (m; 1H): 1.97δ (ddd; 1H): 3.67δ (m; 1H): 5.40δ (br-s; 1H): 7.10δ-7.65δ (m; 8H) | 358 | 204-206 |
| 6.079 (cis) | 1.10δ (m; 1H): 1.45δ (m; 1H): 2.40δ (m; 1H): 3.30δ (m; 1H): 5.40δ (br s; 1H): 6.97δ-7.60δ (m; 8H) | 324 | — |
| 6.143 (cis) | 1.25δ (m; 1H): 1.60δ (m; 1H): 2.54δ (m; 1H): 3.37δ (m; 1H): 5.35δ (br s; 1H): 7.10δ-7.60δ m; 7H): | 372/374/376 | — |

| Compound No. | 1H-NMR data: ppm (multiplicity/number of Hs) | MS [M + H]⁺ | m.p. (° C.) |
|---|---|---|---|
| 6.222 (cis) | 1.25δ (m; 1H): 1.60δ (m; 1H): 2.50δ (m; 1H): 3.47δ (m; 1H): 5.35δ (br s; 1H): 7.17δ-7.60δ (m; 8H) | 340/342 | — |
| Z1.004 cis/trans = 7:3 | cis isomer: 1.15δ (ddd; 1H): 1.60δ (ddd; 1H): 3.10δ (ddd; 1H): 7.30δ-7.45δ (m; 4H). trans isomer: 1.27δ (ddd; 1H): 1.40δ (ddd; 1H): 2.57δ (ddd; 1H): 7.10δ-7.30δ (m; 4H). | — | — |

FORMULATION EXAMPLES FOR COMPOUNDS OF FORMULA I

Example F-1.1 to F-1.2

Emulsifiable Concentrates

| Components | F-1.1 | F-1.2 |
|---|---|---|
| compound of Tables 1 to 16 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1 to 16 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 16 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 16 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 16 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 16 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |

-continued

| Components | F-6.1 | F-6.2 | F-6.3 |
|---|---|---|---|
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 16 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Podosohaera leucotricha*/Apple (Powdery Mildew on Apple)

5 week old apple seedlings cv. McIntosh are treated with the formulated test compound (0.02% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-2

Action Against *Venturia inaegualis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-3

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-4

Action Against *Botrytis cinerea*/Apple (*Botrytis* on Apple Fruits)

In an apple fruit cv. Golden Delicious 3 holes are drilled and each filled with 3011 droplets of the formulated test compound (0.02% active ingredient). Two hours after application 50 μl of a spore suspension of *B. cinerea* ($4 \times 10^5$ conidia/ml) are pipetted on the application sites. After an incubation period of 7 days at 22° C. in a growth chamber the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-5

Action Against *Botrytis cinerea*/Grape (*Botrytis* on Grapes)

5 week old grape seedlings cv. Gutedel are treated with the formulated test compound (0.02% active ingredient) in a spray chamber. Two days after application grape plants are inoculated by spraying a spore suspension ($1 \times 10^6$ conidia/ml) on the test plants. After an incubation period of 4 days at 21° C. and 95% r.h. in a greenhouse the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-7

Action Against *Pyrenophora teres*/Barley (Net Blotch on Barley)

1 week old barley plants cv. Express are treated with the formulated test compound (0.02% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation. Compounds 1.001, 1.004, 1.079, 1.143, 1.222, 2.079, 2.143. 2.222, 6.004, 6.079, 6.143 and 6.222 show good activity in this test (<20% infestation).

Example B-8

Action Against *Septoria tritici*/Wheat (*Septoria* Leaf Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.001, 1.004, 1.079, 1.143, 1.222, 2.079, 2.143. 2.222, 6.004, 6.079, 6.143 and 6.222 show good activity in this test (<20% infestation).

Example B-9

Action Against *Uncinula necator*/Grape (Powdery Mildew on Grape)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

Example B-10

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed. Compounds 1.001, 1.004, 1.079, 1.143, 1.222, 2.079, 2.143. 2.222, 6.004, 6.079, 6.143 and 6.222 show good activity in this test (<20% infestation).

What is claimed is:

1. A fungicidally active compound having formula I:

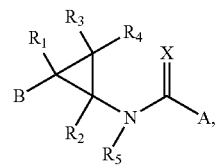

(I)

wherein
X is oxygen or sulfur;
$R_1$ is hydrogen, halogen or $C_1$-$C_6$alkyl;
$R_2$, $R_3$, $R_4$ and $R_5$ are each hydrogen;
A is $A_1$

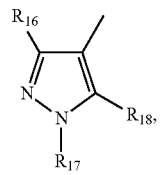

($A_1$)

in which
$R_{16}$ is $C_1$-$C_4$alkyl or $C_1$-$C_4$halogenalkyl;
$R_{17}$ is $C_1$-$C_4$alkyl; and
$R_{18}$ is hydrogen or halogen; and
B is $B_1$

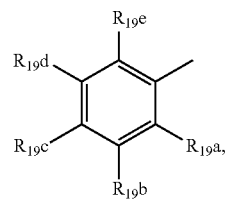

($B_1$)

in which
$R_{19b}$ and $R_{19d}$ are both hydrogen; and
$R_{19a}$, $R_{19c}$ and $R_{19e}$ are each independently hydrogen, halogen, cyano, $C_2$-$C_6$alkynyl, $C_1$-$C_6$halogenalkyl, $C_1$-$C_6$halogenalkoxy or phenyl, which is substituted halogen, provided that at least one of $R_{19a}$, $R_{19c}$ and $R_{19e}$ is not hydrogen; and
tautomers/isomers/enantiomers of the fungicidally active compound.

2. A compound according to claim 1, wherein X is oxygen.
3. A compound according to claim 1, wherein
$R_{19a}$ and $R_{19e}$ are each independently hydrogen; and
$R_{19c}$ is a chloro group.
4. A compound according to claim 1, wherein $R_1$ is hydrogen.
5. A compound according to claim 3, wherein $R_1$ is hydrogen.
6. A fungicidally active composition for controlling and protecting plants against phytopathogenic microorganisms, said fungicidally active composition comprising the fungicidally active compound of claim 1 and an inert carrier.

7. A fungicidally active composition according to claim 6, further comprising at least one additional compound selected from fertilizers, micronutrient donors, herbicides, insecticides, fungicides, bactericides, nematicides, or molluscicides.

8. A fungicidally active composition for controlling and protecting plants against phytopathogenic microorganisms, said fungicidally active composition comprising the fungicidally active compound of claim 2 and an inert carrier.

9. A method of controlling or preventing infestation of useful plants by phytopathogenic microorganisms, wherein the fungicidally active compound of claim 1 or a composition comprising the fungicidally active compound as an active ingredient is applied to the plants, to parts thereof or a locus thereof.

* * * * *